US006803233B2

(12) United States Patent
Lynch et al.

(10) Patent No.: US 6,803,233 B2
(45) Date of Patent: Oct. 12, 2004

(54) MODEL FOR ALZHEIMER'S DISEASE AND OTHER NEURODEGENERATIVE DISEASES

(75) Inventors: Gary Lynch, Irvine, CA (US); Xiaoning Bi, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/917,789

(22) Filed: Jul. 31, 2001

(65) Prior Publication Data

US 2002/0048746 A1 Apr. 25, 2002

Related U.S. Application Data

(60) Provisional application No. 60/222,060, filed on Jul. 31, 2000, and provisional application No. 60/283,352, filed on Apr. 13, 2001.

(51) Int. Cl.[7] .............................. C12N 5/02; C12N 5/06; C12N 5/10
(52) U.S. Cl. ........................ 435/325; 435/347; 435/352; 435/353; 435/354
(58) Field of Search ................................. 435/325, 347, 435/352, 353, 354, 320.1, 368; 434/4, 405, 7.2; 800/6, 12, 18; 536/23.2; C12N 5/02, 5/06, 5/10

(56) References Cited

U.S. PATENT DOCUMENTS

| | | | |
|---|---|---|---|
| 5,135,916 A | 8/1992 | Sims et al. ................. 514/21 |
| 5,328,909 A | 7/1994 | Ando et al. ............... 514/256 |
| 5,336,783 A | 8/1994 | Omura et al. ............. 548/561 |
| 5,340,922 A | 8/1994 | Nixon et al. ............... 530/350 |
| 5,395,958 A | 3/1995 | Ando et al. ............... 560/124 |
| 5,416,117 A | 5/1995 | Ando et al. ............... 514/604 |
| 5,422,359 A | 6/1995 | Ando et al. ............... 514/365 |
| 5,424,325 A | 6/1995 | Ando et al. ............... 514/357 |
| 5,444,042 A | 8/1995 | Bartus et al. ................ 514/2 |
| 5,461,146 A | 10/1995 | Lewis et al. .............. 540/545 |
| 5,492,812 A | 2/1996 | Vooheis ...................... 435/7.1 |
| 5,498,616 A | 3/1996 | Mallamo et al. .......... 514/300 |
| 5,498,728 A | 3/1996 | Sohda et al. ............... 548/493 |
| 5,506,243 A | 4/1996 | Ando et al. ............... 514/345 |
| 5,541,290 A | 7/1996 | Harbeson et al. ......... 530/330 |
| 5,550,108 A | 8/1996 | Sims et al. ................ 514/21 |
| 5,554,767 A | 9/1996 | Wang et al. ............... 548/496 |
| 5,621,101 A | 4/1997 | Lewis et al. .............. 540/545 |
| 5,622,967 A | 4/1997 | Dolle et al. ............... 514/312 |
| 5,622,981 A | 4/1997 | Eveleth et al. ............ 514/380 |
| 5,629,165 A | 5/1997 | Nixon et al. ............... 435/7.21 |
| 5,635,178 A | 6/1997 | Sims et al. ............... 424/145.1 |
| 5,639,783 A | 6/1997 | Ando et al. ............... 514/456 |
| 5,654,146 A | 8/1997 | Braxton et al. .............. 435/6 |
| 5,658,906 A | 8/1997 | Mallamo et al. .......... 514/243 |
| 5,661,150 A | 8/1997 | Shirasaki et al. .......... 514/252 |
| 5,663,294 A | 9/1997 | Colman et al. ............ 530/326 |
| 5,679,680 A | 10/1997 | Wang et al. ............... 514/249 |
| 5,686,269 A | * 11/1997 | Nixon ......................... 435/7.1 |
| 5,691,368 A | 11/1997 | Peet et al. ................. 514/376 |
| 5,693,617 A | 12/1997 | Stein et al. ................. 514/18 |
| 5,714,471 A | 2/1998 | Rowe et al. ............... 514/19 |
| 5,716,980 A | 2/1998 | Sohda et al. ............... 514/419 |
| 5,747,517 A | * 5/1998 | Panetta et al. ............. 514/369 |
| 5,849,691 A | * 12/1998 | Majer et al. ................ 514/9 |
| 5,858,982 A | * 1/1999 | Tung et al. ................. 514/19 |
| 5,981,208 A | 11/1999 | Tamburini et al. ......... 435/23 |
| 6,177,472 B1 | 1/2001 | Wilson et al. ............. 514/646 |
| 6,251,928 B1 | * 6/2001 | Panetta et al. ............. 514/369 |
| 6,288,089 B1 | 9/2001 | Zawada et al. ............. 514/341 |
| 6,447,988 B2 | 9/2002 | Lynch et al. |
| 2001/0007854 A1 | 7/2001 | Lynch et al. ............... 514/6 |
| 2002/0061515 A1 | 5/2002 | Lynch et al. |
| 2002/0094958 A1 | * 7/2002 | Bahr .......................... 514/18 |

FOREIGN PATENT DOCUMENTS

| | | |
|---|---|---|
| EP | 1 026 251 A2 | 8/2000 |
| WO | WO 96/30395 A2 | 10/1996 |
| WO | WO 96/40737 A1 | 12/1996 |
| WO | WO 99/34781 A1 | 7/1999 |
| WO | WO 00/21550 A2 | 4/2000 |
| WO | WO 00/21550 * | 4/2000 |
| WO | WO 00/21575 A2 | 4/2000 |
| WO | WO 01/53340 A2 | 7/2001 |
| WO | WO 02/10768 A2 | 2/2002 |
| WO | WO 02/010768 A3 | 2/2002 |
| WO | WO 02/26107 A2 | 4/2002 |

OTHER PUBLICATIONS

Kenessey et al. (1997) "Degradation of Tau by Lysosomal Enzyme Cathepsin D: Implication for Alzheimer Neurofibrillary Degeneration." Journal of Neurochemistry 69: 2026–2038.*

(List continued on next page.)

Primary Examiner—Gary Kunz
Assistant Examiner—Christopher James Nichols
(74) Attorney, Agent, or Firm—Sterne, Kessler Goldstein & Fox P.L.L.C.

(57) ABSTRACT

The present invention provides a model for studying the development of, and/or pathologies associated with neurodegenerative diseases, and agents that can alter such development and/or pathologies. The model of the invention is especially useful as an Alzheimer's disease model. The model of the invention provides brain cells and a method for increasing neurodegenerative disease characteristics in such cells, especially, induction of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases by selectively increasing the concentration of cathepsin D to an effective level, and/or by lowering the concentration of cholesterol in such cells. The model also provides a method of reversing such effects, by inhibiting cysteine protease and mitogen activated kinase activity, and especially, by inhibiting calpain, and/or MAP kinase.

218 Claims, 31 Drawing Sheets

OTHER PUBLICATIONS

Figure 1A:
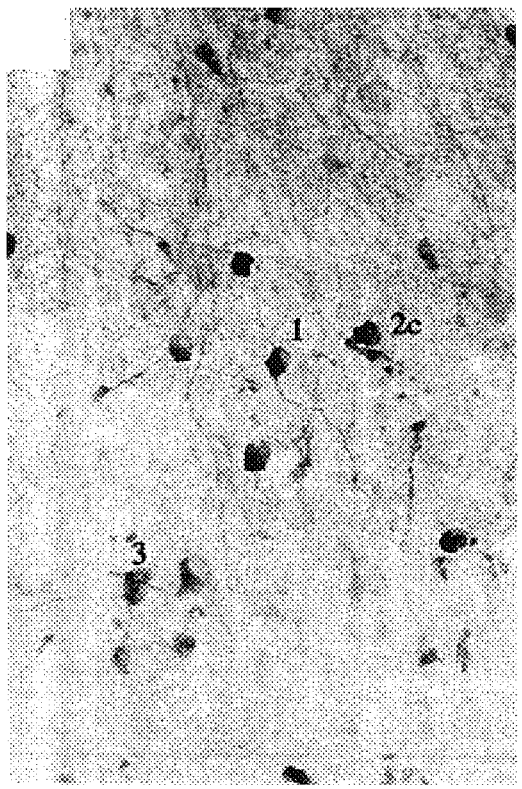
Figure 1B:
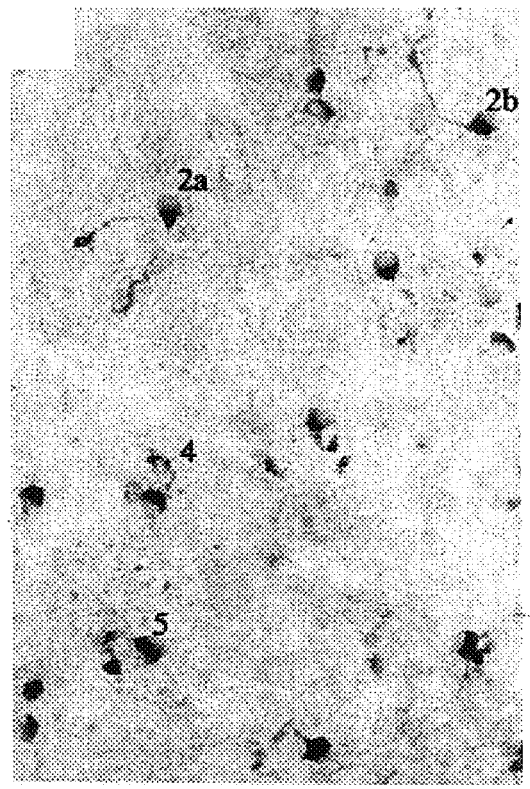
Figure 1C:
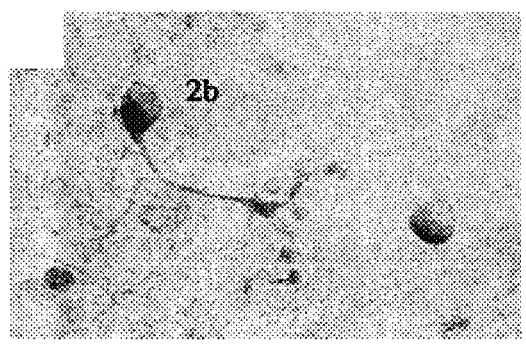
Figure 1D:
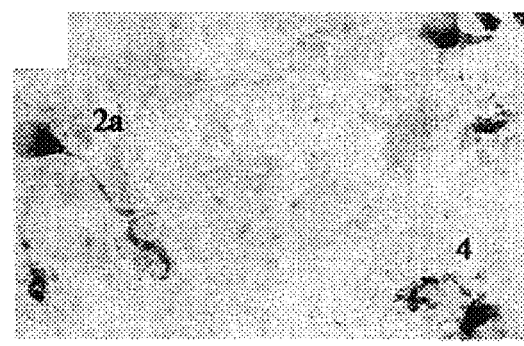

Dyment et al. (1997) "Genetics of multiple sclerosis." Human Molecular Genetics 6(10): 1693–1698.*

Kirkitadze et al. (2002) "Paradigm Shifts in Alzheimer's disease and other neurodegenerative disorders: The emerging role of oliogomeric assemblies." Journal of Neuroscience Research 69: 567–577.*

Monani et al. "Animal models of spinal muscular atrophy." Human Molecular Genetics 9(16): 2451–2457.*

Orr and Zoghbi (2001) "SCA1 molecular genetics: a history of a 13 year collaboration against glutamines." Human Molecular Genetics 10(20): 2307–2311.*

Bi et al. (Aug. 1999) "Lysosomal protease inhibitors induce meganeurites and tangle–like structures in entorinohippocampal regions vulnerable to Alzheimer's disease." Experimental Neurology 158: 312–327.*

Bi et al. (Mar. 21, 2000) "Novel Cathepsin D Inhibitors Block the formation of Hyperphosphorylated Tau fragments in Hippocampus." Journal of.Neurochemistry 74(4): 1469–1477.*

Goldsby et al. KUBY Immunology 4th Ed. (pp. 617).*

Bi, X., et al., "Lysosomal Protease Inhibitors Induce Meganeurites and Tangle–like Structures in Entorhinohippocampal Regions Vulnerable to Alzheimer's Disease," *Exp. Neurol.* 158:312–327, Academic Press (Aug. 1999).

Bi, X., et al., "Novel Cathepsin D Inhibitors Block the Formation of Hyperphosphorylated Tau Fragments in Hippocampus," *J. Neurochem.* 74:1469–1477, Lippincott Williams & Wilkens (Apr. 2000).

Bi, X., et al., "Rapid induction of intraneural neurofibrillary tangles in apolipoprotein E–deficient mice," *Proc. Natl. Acad. Sci. USA* 98:8832–8837, National Academy Press (Jul. 2001).

Coogan, A.N., et al., "The P38 mitogen–activated protein kinase inhibitor SB203580 antagonizes the inhibitory effects of interleukin–1β on long–term potentiation in the rat dentate gyrus in vitro," *Neuroscience* 93:57–69, Elsevier Science, Ltd. (Jun. 1999).

Jarvik, G.P., et al., "Interactions of apolipoprotein E genotype, total cholesterol level, age, and sex in prediction of Alzheimer's disease: A case–control study," *Neurology* 45:1092–1096, Lippincott, Williams & Wilkins (1995).

Ahlijanian, M.K., et al., "Hyperphosphorylated tau and neurofilament and cytoskeletal disruptions in mice overexpressing human p25, an activator of cdk5," *Proc. Natl. Acad. Sci. USA* 97:2910–2915, National Academy Press (Mar. 2000).

Akiyama, H., et al., "Inflammation and Alzheimer's disease," *Neurobiol. Aging* 21:383–421, Elsevier Science, Inc. (May/Jun. 2000).

Bahr, B.A., et al., "Induction of β–Amyloid–Containing Polypeptides in Hippocampus: Evidence for a Concomitant Loss of Synaptic Proteins and Interactions with an Excitotoxin," *Exp. Neurol.* 129:81–94, Academic Press, Inc. (1994).

Bednarski, E., and Lynch, G., "Cytosolic Proteolysis of τ by Cathepsin D in Hippocampus Following Suppression of Cathepsins B and L," *J. Neurochem.* 67:1846–1855, Lippincott–Raven Publishers (1996).

Bednarski, E., et al., "Suppression of Cathepsins B and L Causes a Proliferation of Lysosomes and the Formation of Meganeurites in Hippocampus," *J. Neurosci.* 17:4006–4021, Society for Neuroscience (1997).

Bednarski, E., and Lynch, G., "Selective suppression of cathepsin L results from elevations in lysosomal pH and is followed by proteolysis of tau protein," *Neuroreport* 9:2089–2094, Rapid Science, Ltd. (1998).

Bi, X., et al., "Lysosomal Protease Inhibitors Induce Meganeurites and Tangle–like Structures in Entorhinohippocampal Regions Vulnerable to Alzheimer's Disease," *Exp. Neurol.* 158:312–327, Academic Press (Aug. 1999).

Bi, X., et al., "Novel Cathepsin D Inhibitors Block the Formation of Hyperphosphorylated Tau Fragments in Hippocampus," *J. Neurochem.* 74:1469–1477, Lippincott Williams & Wilkens, Inc. (Apr. 2000).

Biernat, J., et al., "The switch of tau protein to an Alzheimer–like state includes the phosphorylation of two serine–proline motifs upstream of the microtubule binding region," *EMBO J.* 11:1593–1597, Oxford University Press (1992).

Bodovitz, S., and Klein, W.L., "Cholesterol Modulates α–Secretase Cleavage of Amyloid Precursor Protein," *J. Biol. Chem.* 271:4436–4440, American Society for Biochemistry and Molecular Biology, Inc. (1996).

Brown, M.S., and Goldstein, J.L., "Lipoprotein Metabolism in the Macrophage: Implications for Cholesterol Deposition in Atherosclerosis," *Ann. Review Biochem.* 52:223–261, Annual Reviews, Inc. (1983).

Chin, J.Y., et al., "Microtubule–Affinity Regulating Kinase (MARK) Is Tightly Associated with Neurofibrillary Tangles in Alzheimer Brain: A Fluorescence Resonance Energy Transfer Study," *J. Neuropathol. Exp. Neurol.* 59:966–971, American Association of Neuropathologists, Inc. (Nov. 2000).

Eikelenboom, P., et al., "Inflammation and Alzhemer's Disease: Relationships between Pathogenic Mechanisms and Clinical Expession," *Exp. Neurol.* 154:89–98, Academic Press (1998).

Heffernan, J.M., et al., "Temporal Cortex Synaptophysin mRNA Is Reduced in Alzheimer's Disease and Is Negatively Correlated with the Severity of Dementia," *Exp. Neurol.* 150:235–239, Academic Press (1998).

Heinonen, O., et al., "Loss of synaptophysin–like immunoreactivity in the hippocampal formation is an early phenomenon in Alzheimer's disease," *Neurosci.* 64:375–384, Elsevier Science, Ltd. (1995).

Hoffman, K.B., et al., "β–Amyloid increases cathepsin D levels in hippocampus," *Neurosci. Lett.* 250:75–78, Elsevier Science Ireland, Ltd. (1998).

Howland, D.S., et al., "Modulation of Secreted β–Amyloid Precursor Protein and Amyloid β–Peptide in Brain by Cholesterol," *J. Biol. Chem.* 273:16576–16582, The American Society for Biochemistry and Molecular Biology, Inc. (1998).

Huang, D.Y., et al., "ApoE3 binding to tau tandem repeat I is abolished by tau serine$_{262}$ phosphorylation," *Neurosci. Lett.* 192:209–212, Elsevier Science Ireland, Ltd. (1995).

Jicha, G.A., et al., "cAMP–Dependent Protein Kinase Phosphorylations on Tau in Alzheimer's Disease," *J. Neurosci.* 19:7486–7494, Society for Neuroscience (Sep. 1999).

Jick, H., et al., "Statins and the risk of dementia," *The Lancet* 356:1627–1631, The Lancet (Nov. 2000).

Manser, E., et al., "A brain serine/threonine protein kinase activated by Cdc42 and Rac1," *Nature* 367:40–46, Macmillan Magazines, Ltd. (1994).

Mercken, M., et al., "Differential sensitivity to proteolysis by brain calpain of adult human tau, fetal human tau and PHF–tau," *FEBS Lett.* 368:10–14, Elsevier Science B.V. (1995).

Millard, E.E., et al., "Niemann–Pick Type C1 (NPC1) Overexpression Alters Cellular Cholesterol Homeostasis," *J. Biol. Chem.* 275:38445–38451, The American Society for Biochemistry and Molecular Biology, Inc. (Dec. 2000).

Miller, C.C.J., et al., "Alzheimer's paired helical filaments share epitopes with neurofilament side arms," *EMBO J.* 5:269–276, IRL Press, Ltd. (1986).

Nakanishi, H., et al., "Age–Related Changes in Activities and Localizations of Cathepsins D, E, B, and L in the Rat Brain Tissues," *Exp. Neurol.* 126:119–128, Academic Press, Inc. (1994).

Nathan, B.P., et al., "Apolipoprotein E3– and E4–induced differences in neurite outgrowth are associated with differences in the subcellular localization of apolipoprotein E," *Society for Neurosci. Abstracts 20*:1033, Abstract No. 421.5, Society for Neuroscience (1994).

Patrick, G.N., et al., "Conversion of p35 to p25 deregulates Cdk5 activity and promotes neurodegeneration," *Nature* 402:615–622, Macmillan Magazines, Ltd. (Dec. 1999).

Pei, J.–J., et al., "Distribution of Active Glycogen Synthase Kinase 3 β (GSK–3β) in Brains Staged for Alzheimer Disease Neurofibrillary Changes," *J. Neuropathol. Exp. Neurol.* 58:1010–1019, American Association of Neuropathologists, Inc. (Sep. 1999).

Petersen, R.C., et al., "Apolipoprotein E Status as a Predictor of the Development of Alzheimer's Disease in Memory–Impaired Individuals," *JAMA* 273:1274–1278, American Medical Association (1995).

Refolo, L.M., et al., "Hypercholesterolemia Accelerates the Alzheimer's Amyloid Pathology in a Transgenic Mouse Model," *Neurobiol. Dis.* 7:321–331, Academic Press (Aug. 2000).

Rogers, J., et al., "Inflammation and Alzheimer's Disease Pathogenesis," *Neurobiol. Aging 17*:681–686, Elsevier Science, Inc. (1996).

Sawamura, N., et al., "Site–specific Phosphorylation of Tau Accompanied by Activation of Mitogen–activated Protein Kinase (MAPK) in Brains of Niemann–Pick Type C Mice," *J. Biol. Chem.* 276:10314–10319, The American Society for Biochemistry and Molecular Biology, Inc. (Mar. 2001).

Sternberger, L.A., and Sternberger, N.H., "Monoclonal antibodies distinguish phosphorylated an nonphosphorylated forms of neurofilaments in situ," *Proc. Natl. Acad. Sci. USA* 80:6126–6130, National Academy Press (1983).

Sternberger, N.H., et al., "Aberrant neurofilament phosphorylation in Alzheimer disease," *Proc. Natl. Acad. Sci. USA* 82:4274–4276, National Academy Press (1985).

Strittmatter, W.J., et al., "Hypothesis: Microtubule Instability and Paired Helical Filament Formation in the Alzheimer Disease Brain Are Related to Apolipoprotein E Genotype," *Exp. Neurol.* 125:163–171, Academic Press, Inc. (1994).

Teter, B., et al., "Role of apolipoprotein E and estrogen in mossy fiber sprouting in hippocampal slice cultures," *Neurosci. 91*:1009–1016, Elsevier Science, Ltd. (Jul. 1999).

von Bergen, M., et al., "Assembly of τ protein into Alzheimer paired helical filaments depends on a local sequence motif ( $^{306}$VQIVYK$^{311}$) forming β structure," *Proc. Natl. Acad. Sci. USA* 97:5129–5134, National Academy Press (May 2000).

Wolozin, B.L., et al., "A Neuronal Antigen in the Brains of Alzheimer Patients," *Science 232*:648–650, American Association for the Advancement of Science (1986).

Wolozin, B., et al., "Decreased Prevalence of Alzheimer Disease Associated With 3–Hydroxy–3–Methylglutaryl Coenzyme A Reductase Inhibitors," *Arch. Neruol.* 57:1439–1443, American Medical Association (Oct. 2000).

\* cited by examiner

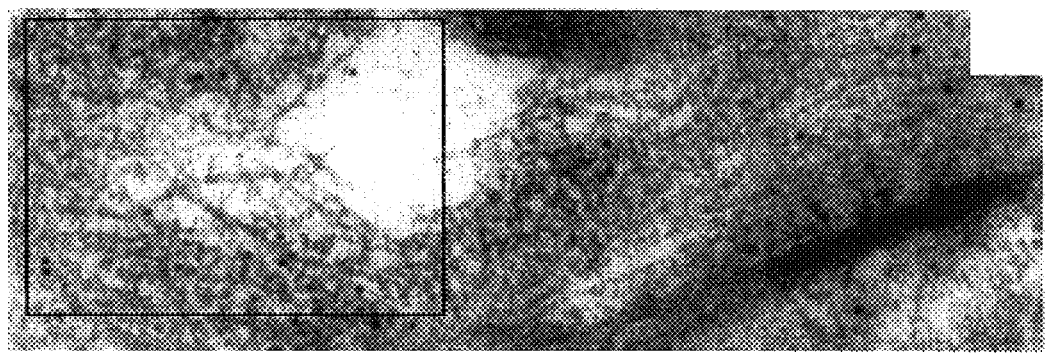
FIG.4A
 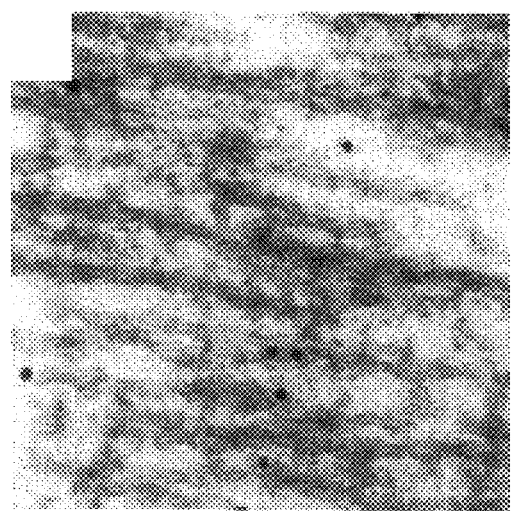
FIG.4B         FIG.4C

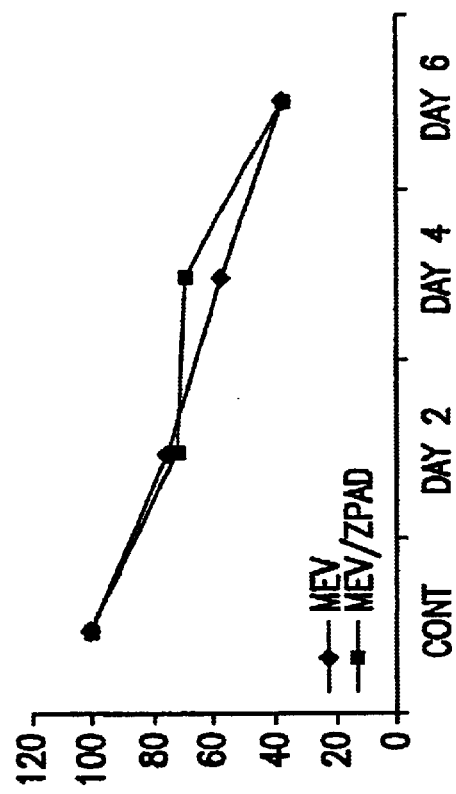
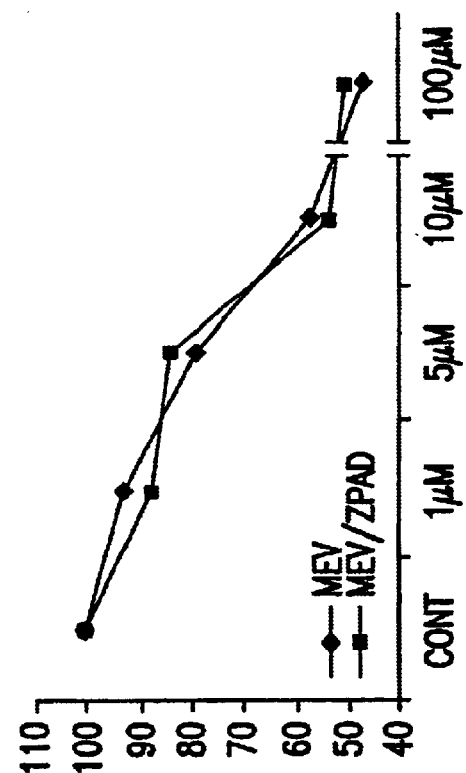
FIG.14A
FIG.14B

MODEL FOR ALZHEIMER'S DISEASE AND OTHER NEURODEGENERATIVE DISEASES

CROSS REFERENCE TO RELATED APPLICATIONS

This application claims the benefit of U.S. Provisional Application No. 60/283,352, filed Apr. 13, 2001, and the benefit of U.S. Provisional Application No. 60/222,060, filed Jul. 31, 2000, the contents of each of which are incorporated herein by reference.

STATEMENT REGARDING FEDERALLY-SPONSORED RESEARCH AND DEVELOPMENT

This invention was made with Government support under Grant No. 455365-30110, awarded by the National Institute on Aging. The Government has certain rights in this invention.

FIELD OF THE INVENTION

The invention is in the field of models for medical diseases. Specifically, the invention is in the field of neurodegenerative disease models, and especially, Alzheimer's disease models.

BACKGROUND OF THE INVENTION

As human life span has significantly expanded over the last century, Alzheimer's disease and other neurodegenerative diseases will have a growing impact on the quality of life for a large proportion of the population. For example, Alzheimer's disease is a leading cause of dementia in the elderly, affecting 5–10% of the population over the age of 65 years. See *A Guide to Understanding Alzheimer's disease and Related Disorders*, edited by Jorm, New York University Press, New York (1987). Alzheimer's disease often presents with a subtle onset of memory loss followed by a slow progressive dementia over several years. The prevalence of Alzheimer's disease and other dementias doubles every five years beyond the age of 65. See 1997 *Progress Report on Alzheimer's disease, National Institute on Aging/National Institute of Health*. Alzheimer's disease now affects 12 million people around the world, and it is projected to increase to 22 million by 2025 and to 45 million by 2050. See *Alzheimer's Association Press Release*, Jul. 18, 2000.

The complexity of the brain's architecture and chemistry, and the complexity of these neurodegenerative brain diseases, especially Alzheimer's disease, has hampered the development of a model that mimics many of the changes seen in the human brain. Such a model is needed in order to identify drugs or other agents that might be useful in treating, preventing or reversing the effects of such diseases.

Alzheimer's disease is histopathologically characterized by the loss of particular groups of neurons and the appearance of two principal lesions within the brain, termed senile plaques and neurofibrillary tangles. See Brion et al., *J. Neurochem.* 60:1372–1382 (1993). Senile plaques occur in the extracellular space. A major component of senile plaques is beta-amyloid (A-beta), a naturally secreted but insoluble peptide formed by cleavage of amyloid precursor protein (APP). A-beta is a fragment close to the carboxyterminal domain of APP.

Neurofibrillary tangles are intraneuronal accumulations of filamentous material in the form of loops, coils or tangled masses. They are most abundantly present in parts of the brain associated with memory functions, such as the hippocampus and adjacent parts of the temporal lobe. See Robbins Pathologic Basis of Disease, Cotran et al., $6^{th}$ ed. (1999). Neurofibrillary tangles are commonly found in cortical neurons, especially in the entorhinal cortex, as well as in other locations such as pyramidal cells of the hippocampus, the amygdala, the basal forebrain, and the raphe nuclei.

Neurofibrillary tangles can also be found during normal aging of the brain, however, they are found in a significantly higher density in the brain of Alzheimer's disease patients, and in the brains of patients with other neurodegenerative diseases, such as progressive supranuclear palsy, postencephaltic Parkinson disease, Pick's disease, amylotrophic lateral sclerosis, etc. *Robbins Pathologic Basis of Disease*, Cotran et al., 6th ed. (1999), p.1330. Previous studies suggest that, among other things, neurofibrillary tangles may significantly contribute to the cognitive decline associated with the disease and also directly to neuronal cell death.

Ultrastructurally, neurofibrillary tangles are composed predominantly of paired helical filaments ("PHF"). A major component of PHF is an abnormally phosphorylated form of a protein called tau and its fragments. *Robbins Pathologic Basis of Disease*, Cotran et al., 6th ed., W. B. Saunders Company (1999), p.1300.

The tau protein (also referred to as "native tau") is a microtubule-associated phosphoprotein that stabilizes the cytoskeleton and contributes to determining neuronal shape. See Kosik & Caceres, *Cell Sci. Suppl.* 14:69–74 (1991). Tau has an apparent molecular weight of about 55 kDa. The protease cathepsin D cleaves tau protein at neutral (cytoplasmic) pH resulting in tau fragments—one of which has a molecular weight of approximately 29 kDa (referred to by some authors as "tau fragment"). See, e.g., Bednarski & Lynch, *J. Neurochem.* 67:1846–1855 (1996); Bednarski & Lynch, *NeuroReport* 9:2089–2094 (1998). Both the tau protein and 29 kDa tau fragment can be phosphorylated. In a normal brain, the tau protein and tau fragment typically exist in an unphosphorylated, or dephosphorylated state. However, in neurofibrillary tangles, both tau protein and tau fragment can be found in an abnormally phosphorylated state, a hyperphosphorylated state. The 29 kDa tau fragment is a major component of neurofibrillary tangles. Hyperphosphorylation impairs tau protein's ability to interact with microtubules.

Bednarski E, and Lynch G, *J Neurochem* 67:1846–55 (1996) cultured hippocampal slices with an inhibitor [N-CBZ-L-phenylalanyl-L-alanine-diazomethyl ketone (ZPAD)] of cathepsins B and L. The authors reported that this resulted in the degradation of high molecular weight isoforms of tau protein and the production of a 29-kDa tau fragment (tau 29).

Bednarski E, and Lynch G, *Neuroreport* 9:2089–2094 (1998) reported that incubating cultured hippocampal slices with chloroquine or with ZPAD resulted in increases in enzymatically active cathepsin D and the delayed appearance of a 29 kDa fragment of the tau protein. The authors proposed that inactivation of cathepsin L leads to induction of cathepsin D which leads to aberrant tau proteolysis and that such a pathway is likely to play an important role in brain aging.

In addition to the build-up of A-beta and of neurofibrillary tangles, increasing evidence has pointed to a link between lipid metabolism and Alzheimer's disease. Epidemiological studies found that patients with increased plasma cholesterol levels and cardiovascular diseases have an increased risk of Alzheimer's disease (Jick, H., et al., *Lancet* 356:627–631 (2000)). Also, long-term therapy with the 3-hydroxy-3-methylglutaryl coenzyme A reductase inhibitors appears to decrease the prevalence of Alzheimer's disease (Jick, H., et al., *Lancet* 356:627–631 (2000); Wolozin, B., et al., *Arch. Neurol.* 57:1439–1443 (2000)).

Consistent with a link to lipid metabolism, in vitro experiments have shown that cholesterol affects the generation and aggregation of beta amyloid (A-beta) (Bodovitz, S., and Klein, W. L., *J. Biol. Chem.* 271:4436–4440 (1996); Xu, H., et al., *Proc. Natl. Acad. Sci. U S A* 94:3748–3752 (1997); Howland, D. S., et al., *J. Biol. Chem.* 273:16576–16582 (1998) ). Transgenic mice fed a high cholesterol diet also developed increased amounts of A-beta deposition (Refolo, L. M., et al., *Neurobiol. Dis.* 7:321–331 (2000)).

ApoE-mediated transport of cholesterol into lysosomes is a critical step for cells to utilize these sterols, which is of particular importance for mature neurons that mainly rely on extracellular cholesterol (Brown, M. S., and Goldstein, J. L., *Annu. Rev. Biochem.* 52:223–261 (1983)). Once in the lysosome, cholesterol and other lipids dissociate from ApoE before being utilized by the cell (Brown, M. S., and Goldstein, J. L., *Annu. Rev. Biochem.* 52:223–261 (1983)).

Changes in cholesterol levels may be involved in certain neurodegenerative diseases. For example, accumulation of insoluble A-beta1–42 has been found in Niemann-Pick type C (NPC) mutant cells (Yamazaki, T., et al., *J. Biol. Chem.* (2000)(epub ahead of print)). These cells exhibit many pathologic characteristics, one of which is impaired intracellular transport of cholesterol (Millard, E. E., et al., *J. Biol. Chem.* 275:38445–38451 (2000)). Also, the ApoE4 isoform is a known risk factor for late-onset Alzheimer's disease.

Inhibition of cholesterol synthesis enhanced the phosphorylation of tau in dissociated cell cultures [ref. in (Sawamura, N., et al., *J. Biol. Chem.* 57:1439–1443 (2001))]. Likewise, hyperphosphorylation of tau has been demonstrated in cell cultures prepared from NPC mutant mice (Sawamura, N., et al., *J. Biol. Chem.* 57:1439–1443 (2001)). Gradually developing disturbances in lysosomes, which affect the sorting/trafficking of cholesterol from lysosomes and late endosomes, may, therefore, be contributors to the pathologies associated with neurodegenerative diseases and Alzheimer's disease.

There has been considerable research into mechanisms underlying neurodegenerative diseases, including Alzheimer's disease. Many transgenic animal models of Alzheimer's disease have been developed and used in an attempt to study the mechanisms of Alzheimer's disease as well as to screen compounds that may ameliorate the conditions of Alzheimer's disease. However, many in vivo or in vitro models lack some of the important features of Alzheimer's disease, such as neurofibrillary tangles. Thus, there is an ongoing need to develop a model, especially one useful in vivo or in vitro, that mimics the pathology of neurodegenerative diseases including Alzheimer's disease and new ways to investigate and combat such conditions. The present invention meets these and other needs.

BRIEF SUMMARY OF THE INVENTION

The present invention provides a model for Alzheimer's disease and other neurodegenerative diseases. The model of the invention provides brain cells, or brain tissue containing the same, and a method for increasing or decreasing characteristics and changes indicative of neurodegenerative diseases in such cells, especially, the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases and/or any other characteristic or change indicative of neurodegenerative diseases in such cells.

The model of the invention has identified new targets for therapeutic intervention, and new classes of compounds for the treatment of neurodegenerative diseases, and especially, Alzheimer's disease. For example, the model of the invention has identified the inhibition of tau proteolysis as a new target for therapeutic intervention. As shown herein, cysteine protease inhibitors, and specifically, calpain inhibitors, are capable of inhibiting tau proteolysis and thus the formation of tau fragments. Such inhibitors prevent the formation of neurofibrillary tangles (the formation of which have been induced, according to the model of the invention, by conditions that raise the amount and/or activity of cathepsin D and/or conditions that lower the amount or concentration of cholesterol in the brain tissue).

Accordingly, in one aspect, the invention provides a model of neurodegenerative disease development, such model being a method of increasing the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases, in a suitable brain cell(s), or brain tissue preparation containing the same, the method comprising (1) inducing lysosomal dysfunction and selectively increasing cathepsin D, or, selectively lowering cholesterol, in the brain cell, to levels sufficient to effect the desired changes and (2) culturing the brain cell of part (1) for a period of time sufficient to effect such changes, such changes including the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in such cell relative to the levels found in control cells. In a further embodiment, cathepsin D is selectively increased and also cholesterol is selectively lowered in the brain cells.

In another aspect, the invention provides a method comprising: (a) exposing brain cells, or brain tissue preparation containing the same, to a condition, or contacting brain cells, or brain tissue containing the same, with a compound that inhibits or suppresses lysosomal function, increases cathepsin D, or decreases cholesterol, to a level effective to induce characteristics or indicia of a brain afflicted with a neurodegenerative disease in the cells by the continued exposure thereto; and (b) maintaining the cells for a period of time sufficient to induce such properties or indicia, wherein such properties or indicia include the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases. In a further embodiment, cathepsin D is selectively increased and also cholesterol is selectively decreased in the brain cells, or brain tissue containing the same.

In yet another aspect, the invention provides brain cells, or brain tissue containing the same, that have been exposed to conditions that inhibit or suppress lysosomal function, increase cathepsin D, or, that selectively decrease cholesterol, to a level effective to increase the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in such brain cells, or brain tissue preparations containing the same, compared to such levels in a control. In a further embodiment, the brain cells, or brain tissue containing the same, have been prepared from medium in which both cathepsin D is selectively increased and cholesterol is selectively decreased.

In yet another aspect, the invention provides brain cells, or brain tissue containing the same, that contain (in the media or in the cell), or that have been treated with, a compound that inhibits or suppresses lysosomal function, increases cathepsin D, or that lowers cholesterol in such brain cells, or brain tissue containing the same, to a level effective to increase the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in such brain cells, or brain tissue containing the same, compared to such levels in a control. In a further embodiment, both cathepsin D has been selectively increased and cholesterol levels have been selectively decreased in the cells as a result of such compound. In a preferred embodiment, such compound or its precursor was exogenously administered.

In yet another aspect, the invention provides a screening method comprising: (a) contacting brain cells, or brain tissue containing the same, with a cathepsin D-increasing compound that increases cathepsin D in the brain cells, or with an agent capable of decreasing cholesterol, wherein the change in cathepsin D or cholesterol is sufficient to increase the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in the brain cells, or brain tissue containing the same; (b) contacting the brain cells with an agent; and (c) determining whether the agent modulates the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in the brain cells, as compared to brain cells that are not treated with the agent. In a further embodiment, both cathepsin D is selectively increased and cholesterol is selectively decreased in the brain cells, or brain tissue containing the same, prior to contact with such agent.

In yet another aspect, the invention provides a method of decreasing neurofibrillary tangles, phosphorylated tau and/or tau fragments, or of preventing the formation of the same, in any suitable brain cell, or brain tissue containing the same, that contains, or has been induced to form, such neurofibrillary tangles, phosphorylated tau and/or tau fragments in such brain cell, the method comprising (1) selectively inhibiting the activity of cysteine proteases, and especially of calpain, in the brain cell and (2) culturing the brain cell containing the selectively inhibited protease from part (1) for a period of time sufficient to reduce the amount of neurofibrillary tangles, phosphorylated tau and/or tau fragments in such cell.

In yet another aspect, the invention provides a method comprising (a) exposing the brain cells, or brain tissue containing the same, to a condition, or contacting the brain cells, or brain tissue containing the same, with a compound, that inhibits the activity of cysteine proteases, or at least of a cysteine protease, and especially calpain, to a level effective to result in a reduction or lessening in the properties or indicia of a brain afflicted with a neurodegenerative disease by the continued exposure to, contact with, or incubation therein, and (b) maintaining such exposure or contact or incubation for a period of time sufficient to reduce such properties or indicia, wherein such properties or indicia include increased amounts of neurofibrillary tangles, phosphorylated tau and/or tau fragments.

In yet another aspect, the invention provides brain cells, or brain tissue containing the same, that have been exposed to a compound or conditions in which cysteine proteases, and especially calpain, in such cells are selectively inhibited, and that lack, or contain a lower amount of neurofibrillary tangles, phosphorylated tau and/or tau fragments as a result of such inhibition.

In yet another aspect, the invention provides brain cells, or brain tissue containing the same, that contain (in the media or in the cell), or that have been treated with, a compound that selectively inhibits cysteine proteases, and especially calpain, in such cells, such brain cells, or brain tissue containing the same, lacking, or containing, a lower amount of neurofibrillary tangles, phosphorylated tau and/or tau fragments as a result of such inhibition.

In yet another aspect, the invention provides a screening method comprising: (a) contacting brain cells, or brain tissue containing the same, with a compound that effectively inhibits the activity of cysteine proteases, and especially calpain, in the brain cells, or brain tissue containing the same, wherein the inhibition of such cysteine proteases, and especially, the inhibition of calpain, decreases, or prevents an increase in, the amount of neurofibrillary tangles, phosphorylated tau and/or tau fragments in the brain cells, or brain tissue containing the same; (b) contacting the brain cells, or brain tissue containing the same, with an further agent; and (c) determining whether the agent of part (b) modulates the amount of neurofibrillary tangles, phosphorylated tau and/or tau fragments in the brain cells, or brain tissue containing the same, treated with the agent compared to the brain cells, or brain tissue containing the same, that are not treated with the agent.

In yet another aspect, the invention provides a method of decreasing the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases or of preventing the formation of the same, in any suitable brain cell, or brain tissue containing the same, that contains, or has been induced to form such neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in such brain cell, the method comprising (1) selectively inhibiting the activity of a mitogen activated kinase, and especially of MAP kinase, in the brain cell and (2) culturing the brain cell containing the selectively inhibited kinase from part (1) for a period of time sufficient to reduce the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in such cell.

In yet another aspect, the invention provides a method comprising (a) exposing the brain cells, or brain tissue containing the same, to a condition, or contacting the brain cells, or brain tissue containing the same, with a compound, that inhibits the activity of a mitogen activated kinase, and especially MAP kinase, to a level effective to reduce the properties or indicia of a brain afflicted with a neurodegenerative disease by the continued exposure to, contact with, or incubation therein, and (b) maintaining such exposure or contact or incubation for a period of time sufficient to reduce such properties or indicia, wherein such properties or indicia include one or more of neurofibrillary tangles, phosphorylated tau, and/or tau fragments, the production of cytokines, the release of cytokines, microglia reactions, microglia activations, inflammation and/or conversion of p35 to p25 and/or the levels and activities of protein kinases.

In yet another aspect, the invention provides brain cells, or brain tissue containing the same, that have been exposed to a compound or conditions in which a mitogen activated kinase, and especially MAP kinase, in such cells are selectively inhibited, and that lack, or contain a lower amount of, neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases as a result of such inhibition.

In yet another aspect, the invention provides brain cells, or brain tissue containing the same, that contain (in the media or in the cell), or that have been treated with, a compound that selectively inhibits a mitogen activated kinase, and especially MAP kinase, in such cells, such brain cells, or brain tissue containing the same, lacking, or containing, a lower amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases as a result of such inhibition.

In yet another aspect, the invention provides a screening method comprising: (a) contacting brain cells, or brain tissue containing the same, with a compound that effectively inhibits the activity of a mitogen activated kinase, and especially MAP kinase, in the brain cells, or brain tissue containing the same, wherein the inhibition of such a mitogen activated kinase, and especially, the inhibition of MAP kinases, decreases, or prevents an increase in, the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in the brain cells, or brain tissue containing the same; (b) contacting the brain cells, or brain tissue containing the same, with an further agent; and (c) determining whether the agent of part (b) modulates the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in the brain cells, or brain tissue containing the same, treated with the agent compared to the brain cells, or brain tissue containing the same, that are not treated with the agent.

In preferred embodiments of the above models, methods and brain cells, or brain tissue containing the same, "wild-type" brain cells from rats or mice, or brain tissue containing the same, apoE-deficient brain cells, or brain tissue containing the same, or apoE4-containing brain cells, or brain tissue containing the same, are used.

In yet another aspect, the invention provides a method for the treatment or prevention of neurodegenerative diseases that are characterized by tau proteolysis, an accumulation of tau fragments, or paired helical filaments, or neurofibrillary tangles, such method comprising the administration of an inhibitor of tau proteolysis to a patient in need of such treatment or prevention.

BRIEF DESCRIPTION OF THE DRAWINGS/FIGURES

FIGS. 1A–D illustrate morphology of subicular neurons immunopositive for phosphorylated tau in cultured slices prepared from apoE-knockout mice. The slices were treated with ZPAD for six days followed by six-day washout. Panels A and B. Micrographs showing the variety of routinely encountered structures 1. A shrunken neuron with a dense, intracellular accumulation of phosphorylated tau 2. Neurons with immunopositive processes that appear distended (2a) or fragmented (2b, 2c) at varying distances from the cell body. 3, Cells with fibril-filled processes that have separated, or are about to separate, from the soma. 4 & 5, Neuronal remnants in which the membrane and cytoplasm are lost but labeled fibrils remain. Panels C and D. Higher magnification images of cells in panel B. The extended and distorted appearance of the terminal portion of the labeled process is evident for cell 2b. A similar effect accompanied by kinking of the neuronal process can be seen for cell 2a. A remnant neuron marked by heavy stained fibrils is present in the lower right of the micrograph in panel D.

Figure 2A:
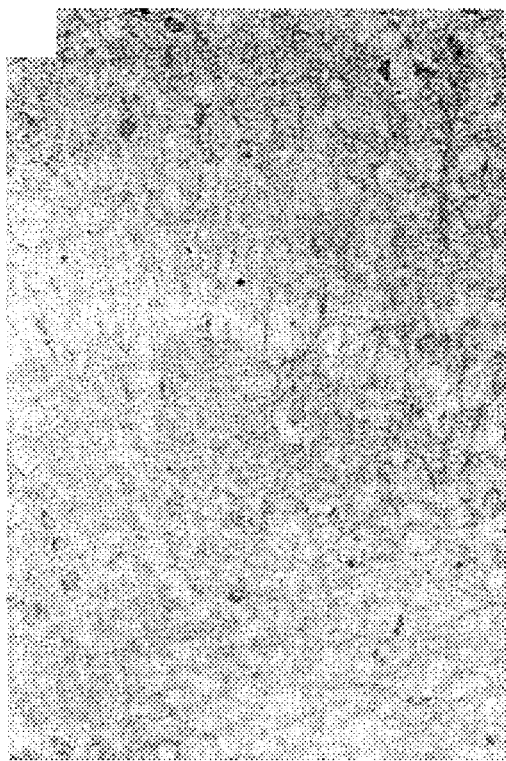
Figure 2B:
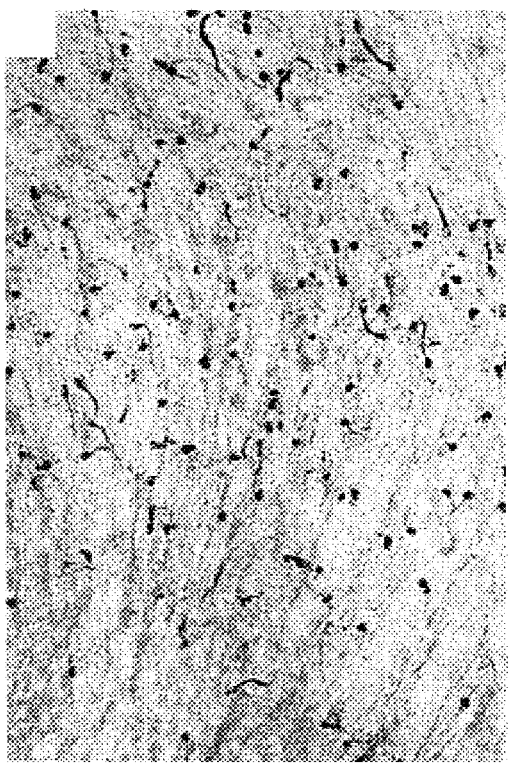

FIGS. 2A and 2B illustrate induction of tangle-like structures in subfield CA1/subiculum in mouse hippocampal cultures by ZPAD-treatment. Hippocampal slice cultures incubated with ZPAD (B) or vehicle (A) for 6 days were stained with monoclonal antibody. "AT8," that recognizes hyperphosphorylated tau proteins and neurofibrillary tangles in human tissue. Numerous immunopositive neurons are present in ZPAD treated slices, while few if any are found in control tissue (A).

Figure 3A:
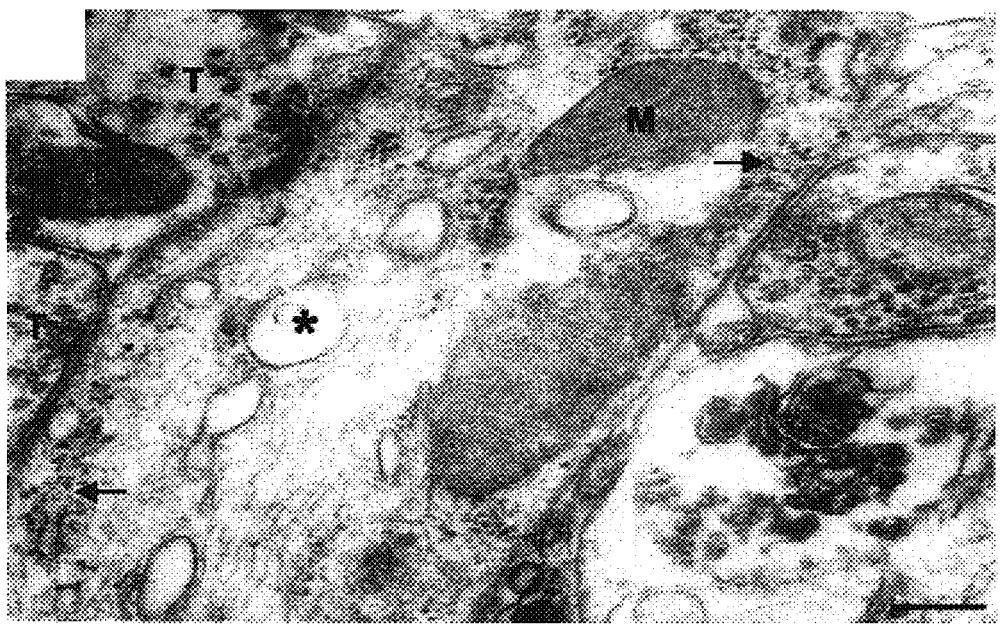
Figure 3B:
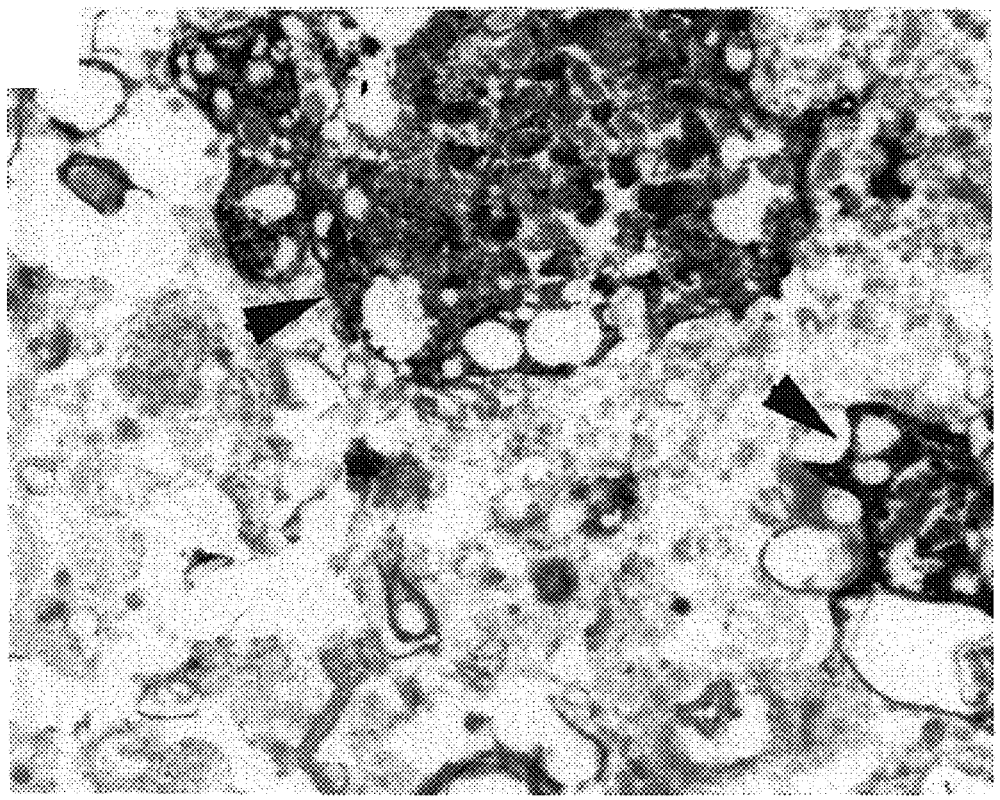

FIGS. 3A and 3B illustrate ultrastructure of tangle-like formations using electron microscopic immunogold techniques. FIG. 3A shows a dendritic branch with accumulated organelles resembled smooth ER (arrows), rough ER (asterisks), or mitochondria (M). distorted microtubules were found passing through the abnormal inclusions. Despite these obvious pathologies, plasma membranes and synaptic apparatus were still distinguishable. Secondary lysosomes with variable sizes were also frequently encountered in ZPAD treated tissues (FIG. 3B).

FIGS. 4A–C-illustrate immunogold analysis and shows that AT8-immunoreactivity (AT8-ir) was found mainly over structures composed of distorted filaments located throughout dendrites and cell bodies. Enlarged images showed that filaments were often paired and twisted with axial periodicity (FIGS. 4A, B). Distorted filaments were found running across each other or waving around, characteristics similar to early-stage neurofibrillary tangles in Alzheimer's disease (FIG. 4C).

FIGS. 5(A and B). Levels of cathepsin D immunoreactivity in apoE-deficient and wild-type (WT) mice. Hippocampal slices prepared from C57BL/6J and C57BL/6J-apoE$^{tm1Unc}$ (apoE-deficient) mice at postnatal day 10 and cultured for 12–14 days were incubated with ZPAD or vehicle (Con) for 6 days. Immunoblots probed with anti-cathepsin D antisera revealed three major bands with apparent molecular weights of ~55 kDa, ~50 kDa, and ~38 kDa in cultured hippocampal slices, corresponding to the inactive proenzyme, the active single chain, and the active heavy chain, respectively (A). ZPAD-treatment increased the first two isoforms in wild-type tissue, and all three isoforms in the apoE-deficient slices. Note also that the increase in cathepsin D proteins is exaggerated in the knockout compared to the wild-type mice: 145+43%, 150+29% and 84+26% vs. 65+29%, 42+22% and 3.0+5.7% (B). Standard paired t-tests (2-tails) were used for the indicated statistical comparison.

Figure 6A:
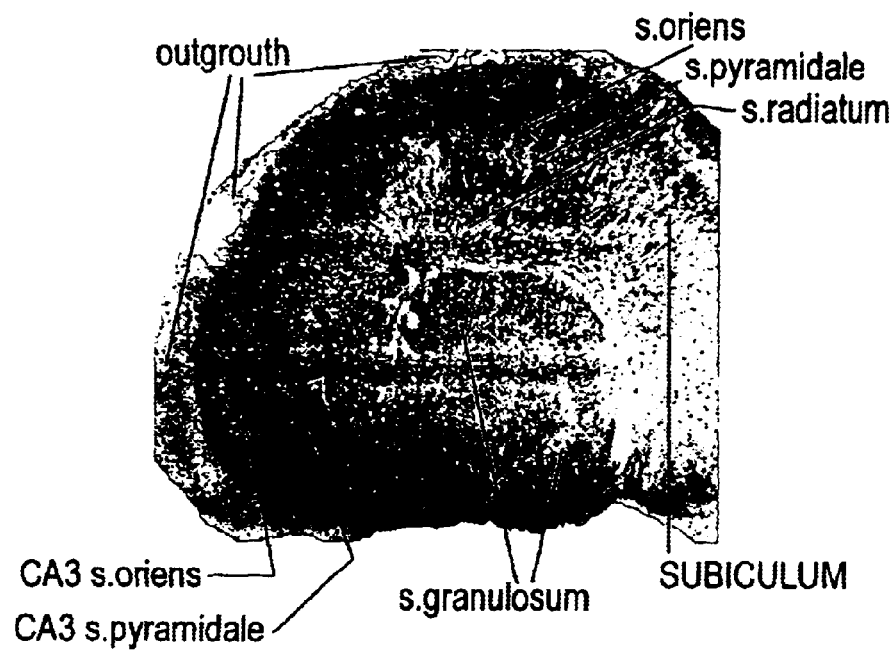
Figure 6B:
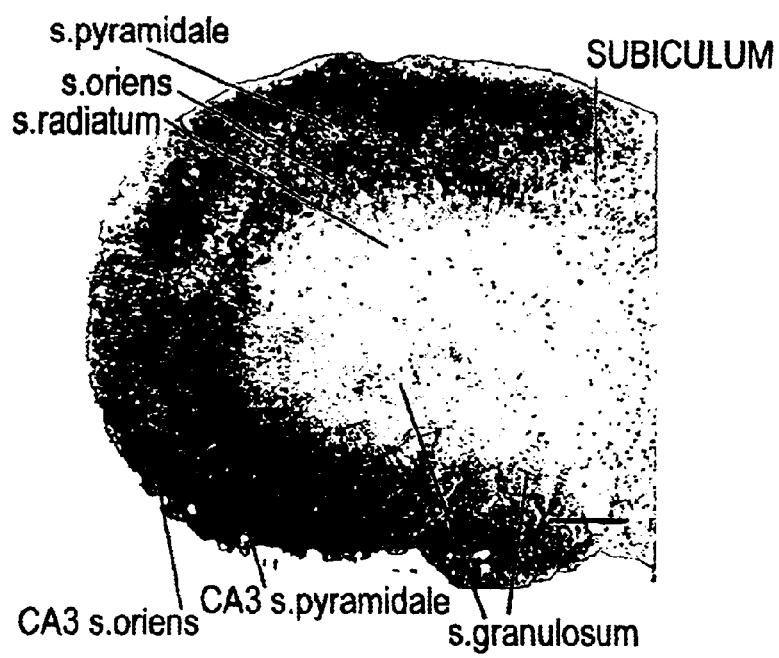

FIG. 6. Induction of tangle-like structures in cultured hippocampal slices prepared from apoE-knockout mice. Slices were incubated with vehicle (A) or 'ZPAD', an inhibitor of cathepsins B and L (B), for 6 days and then processed for immunocytochemistry using a monoclonal antibody "AT8" that recognizes hyperphosphorylated tau proteins, tau fragments, and neurofibrillary tangles in human tissue. Immunopositive elements are found in the outgrowth regions of the control slice from an apoE −/− mouse but not within the hippocampus itself. In contrast, the ZPAD-treated slice has numerous, densely labeled cells in the stratum oriens of hippocampal field CA1 and in the subiculum. Note that the densely packed neurons in the s. pyramidale of field CA3 and in the s. granulosum of the dentate gyrus are not stained (4×objective; scale bar=200 μm).

Figure 7:
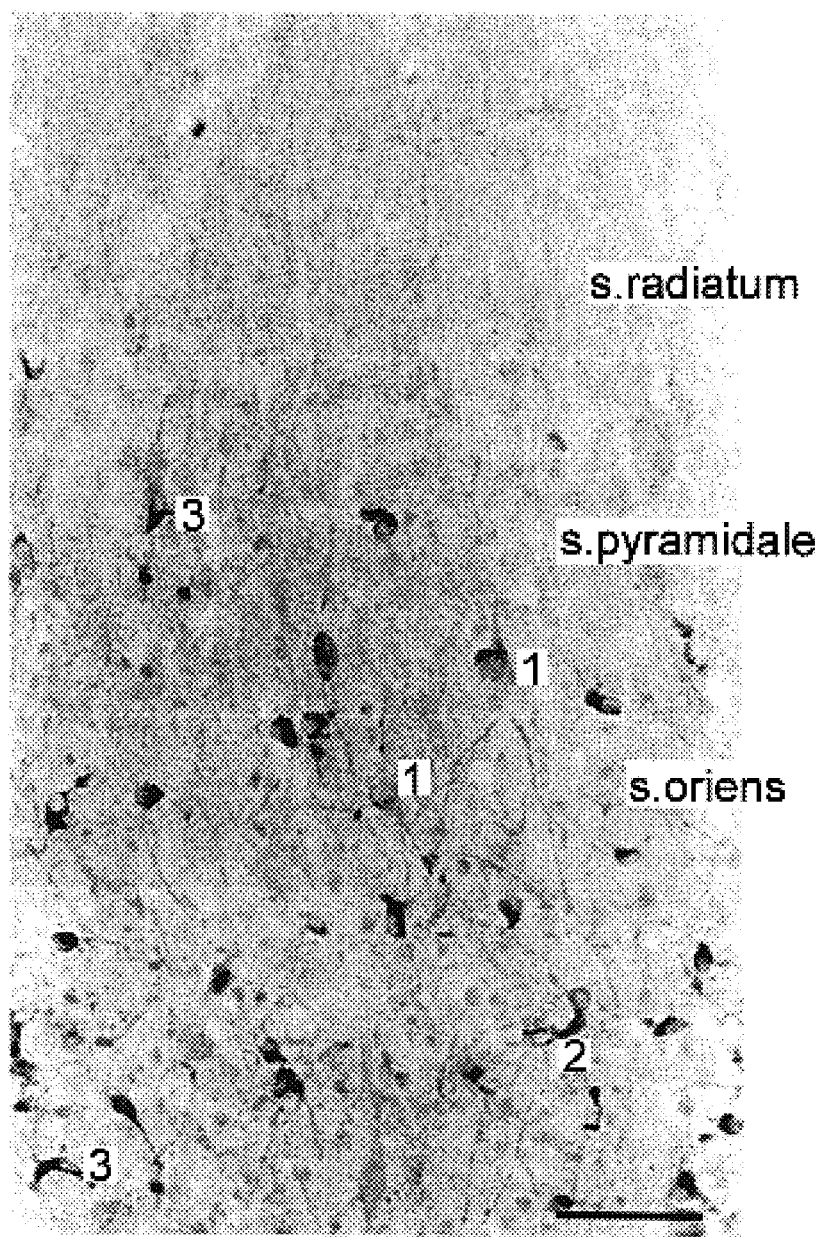

FIG. 7. Types and distribution of phosphorylated tau-immunoreactive neurons in the CA1 region following six days of ZPAD. Shown is a vertical section that extends across most of the basal (s. oriens), and the inner third of the apical (s. radiatum), dendritic fields in field CA1 of a cultured slice that had been exposed to ZPAD for six days. The majority of the AT8 immunopositive cells were found in the basal dendritic field. The cell bodies (s. pyramidale) and apical dendrites of the pyramidal cells, by far the most numerous population of neurons in the section, were with few exceptions, unlabeled. One of these immuno-negative neurons is outlined with small circle. The stained elements were not homogeneous. The cells marked with a "1" appear to be intact neurons with immunopositive processes and dense deposits accumulating within the cell body. The labeled neuron marked as "2" had swollen and distorted dendrites. The elements marked by a "3" appeared to be remnants of neurons. (25×objective, scale bar=50 μm).

Figure 8:
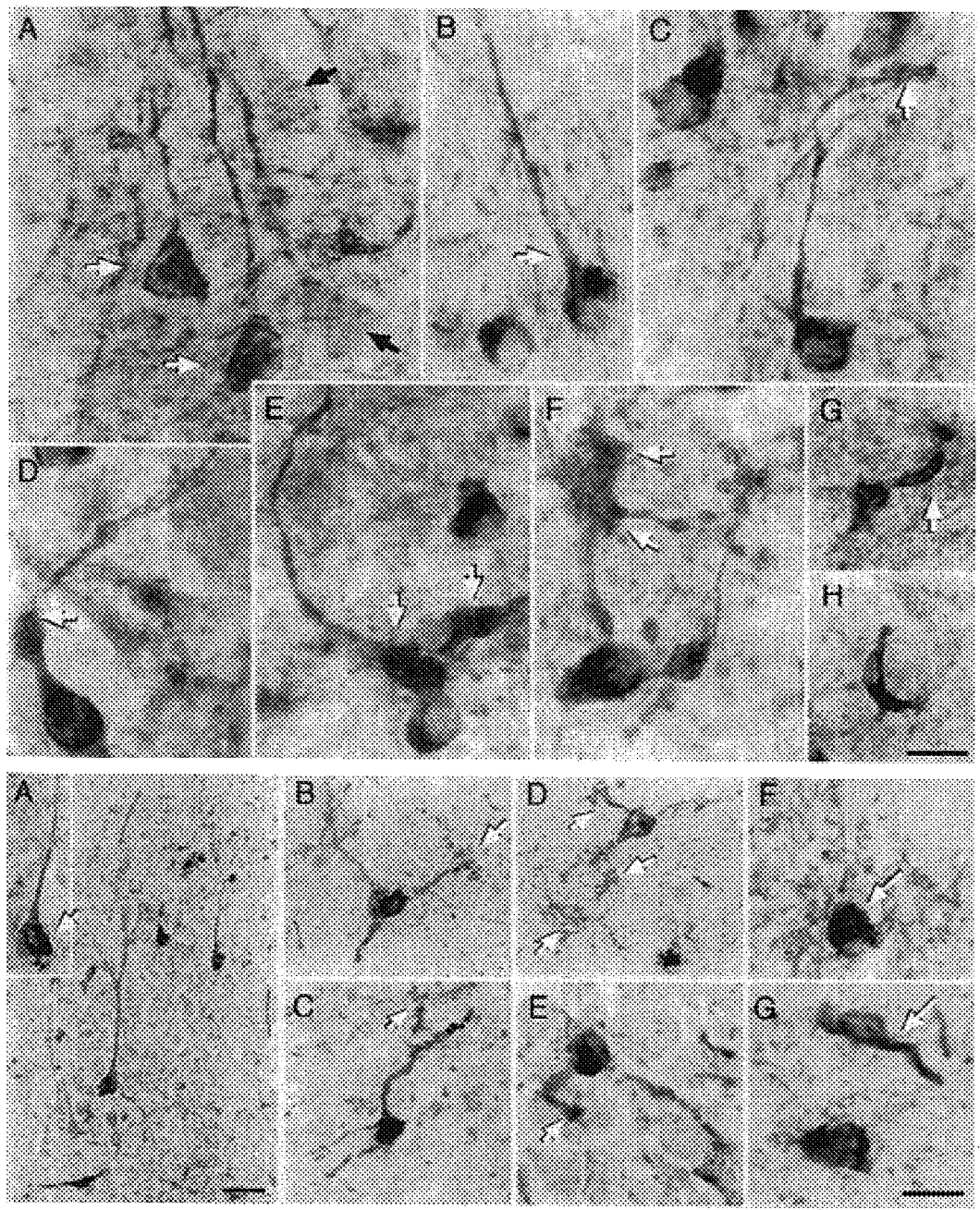

FIG. 8. Morphology of neurons that are stained by an antibody that recognizes neurofibrillary tangles. Upper panel. Immunopositive neurons in cultured slices prepared from apoE −/− mice. The micrographs are ordered according to a proposed sequence of pathological steps. [A] Two neurons in the subiculum with immunopositive cell bodies and primary dendritic branches (white arrows). Note that other neurons in the field are unlabeled (black arrows). [B] Neuron with a dense deposit (cap) in one pole of its cell body. [C] Neuron with pathological swelling (arrow) of a distal dendrite. [D, E] Cells with pathological dendritic expansions proximal to the cell body. [F] Exploded process attached to a dendrite containing fibrous material. Note that the dense 'cap' of immunopositive material covers most of the cell body. [G, H] Dense caps that do not appear to be associated with somata; i.e., are likely the remnants of neurons. (100×objective, scale bar=12.5 μm in A, 10 μm in B, 8 μm in C, 15 μm in D,H; 11 μm in E,G; and 17 μm in F). Lower panel. Immunopositive neurons in the hippocampus from a human brain classified as being in the early stages of Alzheimer's disease. The micrographs are again arranged according to a proposed sequence of pathologies. [A] Apparently intact pyramidal neuron with a dense cap and a labeled apical dendrite. [B, C] Neurons with dendritic swellings. [D, E]. Dendritic expansions proximal to the cell body. [F, G] Immunopositive caps that do not appear to be attached to intact neurons. (20 and 40×objectives; scale bar=50 μm in A; scale bar=45 μm in B, D; 30 μm in C, 18 μm in E, 20 μm in F, and 12.5 μm in G).

Figure 9A:
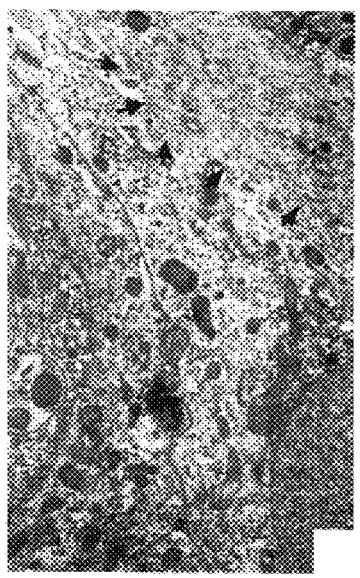
Figure 9B:
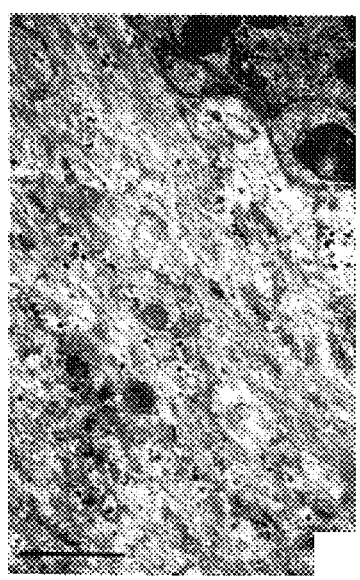
Figure 9C:
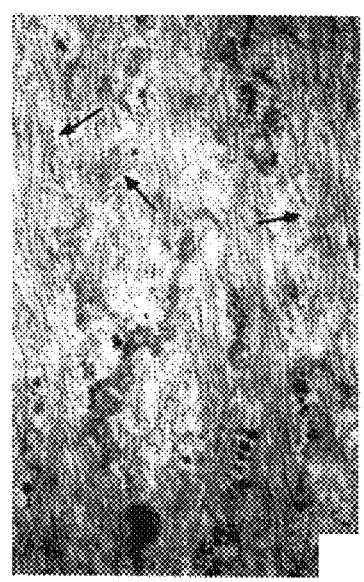

FIG. 9. Electron micrographs of CA1 neurons from apoE −/− slices that were incubated with ZPAD for six days. [A]. Survey micrograph showing the primary dendrite emerging from the cell body. Filamentous material (arrows) occupies more than half of the cross-section of the dendrite. [B]. Higher power image showing the filaments that occupy the pathological region marked in panel A. [C]. Micrograph from another dendrite showing that the filaments form bundles that criss-cross each other (arrows). (scale bar=2 μm in A, 0.75 μm in B, 0.4 μm in C).

Figure 10A:
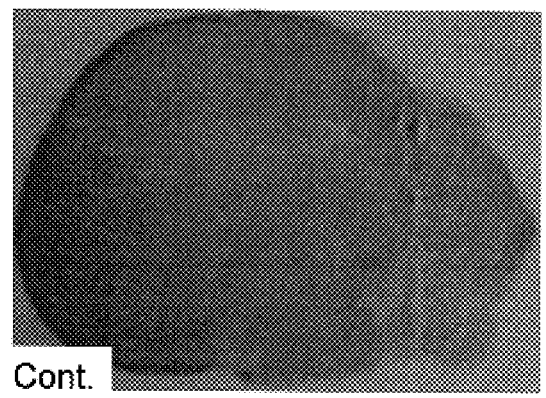
Figure 10B:
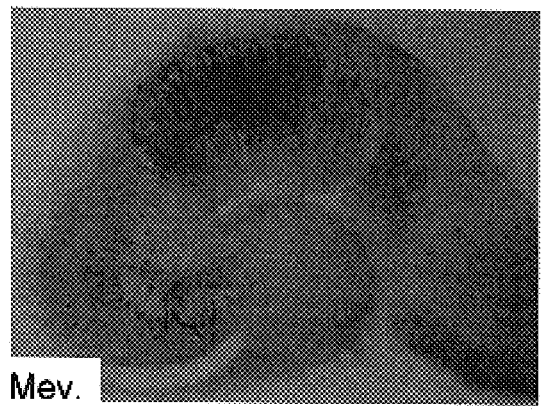
Figure 10C:
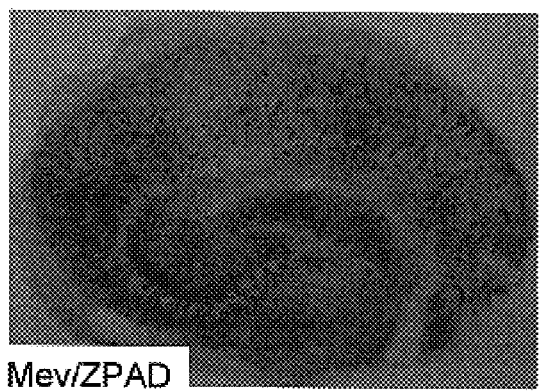
Figure 11A:
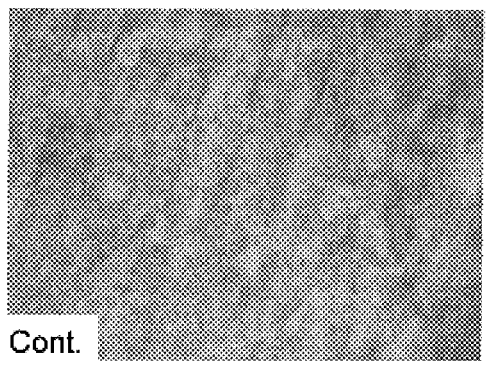
Figure 11B:
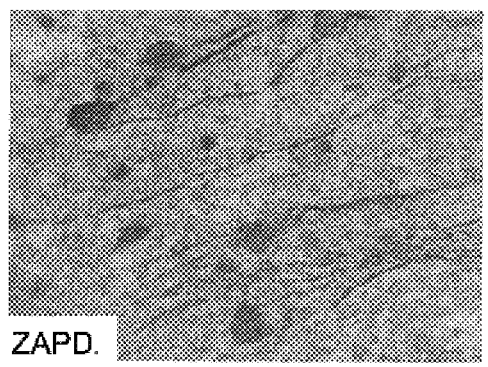
Figure 11C:
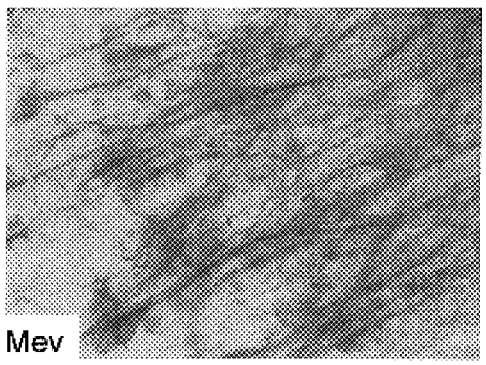
Figure 11D:
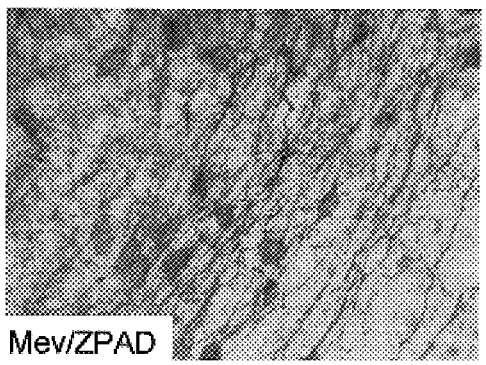

FIG. 10. Tangle-like structures are increased in cultured hippocampal slices by combined lysosomal dysfunction and disturbance in lipid metabolism. Hippocampal slices were prepared from 12 day old rat pups, cultured in vitro for 10 days, and incubated with vehicle only (Cont), and/or a cholesterol metabolism inhibitor mevastatin (Mev), and/or a cathepsin B and L inhibitor (ZPAD) plus mevastatin (Mev/ZPAD). Cultured slices were stained with anti-phosphorylated tau antibody AT8.

FIG. 11. High magnification micrographs of cultured hippocampal slices that were treated with vehicle (Cont), ZPAD, mevastatin (Mev), or mevastatin plus ZPAD (Mev/ZPAD).

Figure 12A:
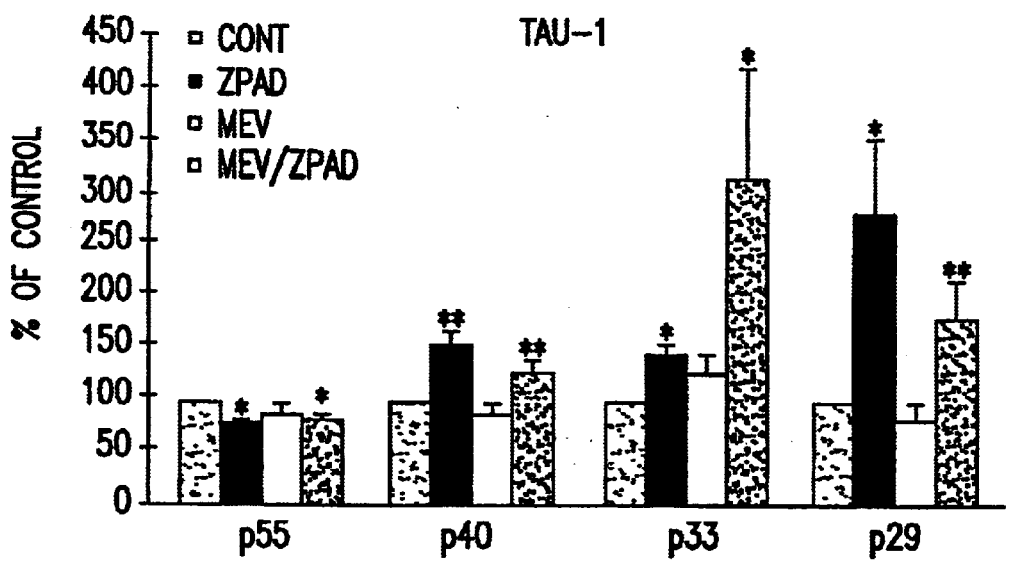
Figure 12B:
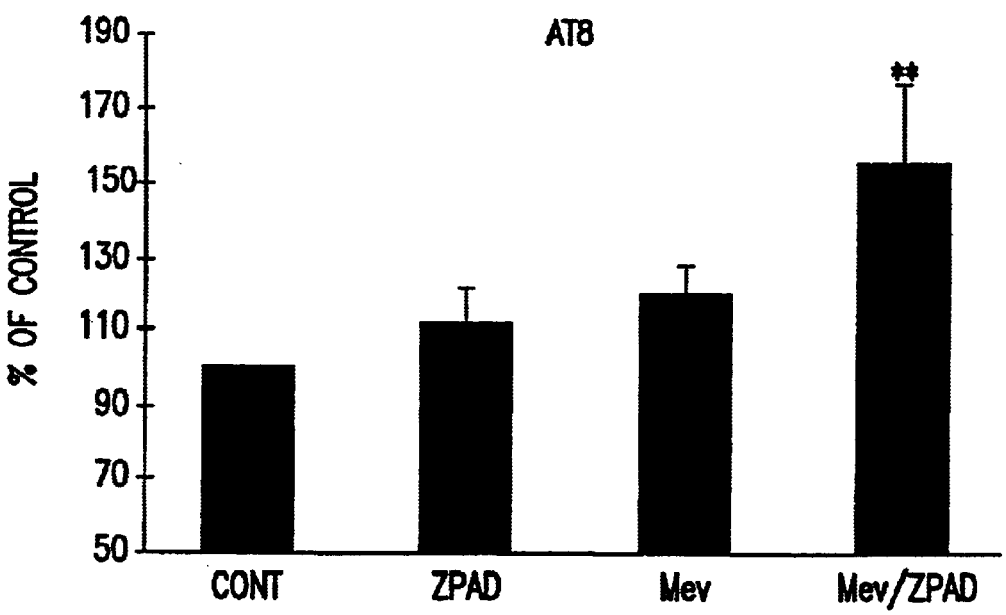

FIG. 12. Generation of phosphorylated tau fragments by mevastatin and ZPAD treatment. Hippocampal slices were prepared from 12 day old rat pups, cultured in vitro for 10 days, and incubated with vehicle only (Cont), and/or a cathepsin B and L inhibitor (ZPAD), and/or a cholesterol metabolism inhibitor mevastatin (Mev), and/or mevastatin plus ZPAD (Mev/ZPAD). Panel A shows the production of tau-1 breakdown products after the indicted treatments and panel B shows the production of phosphorylatec tau-1 after the indicated treatments.

Figure 13:
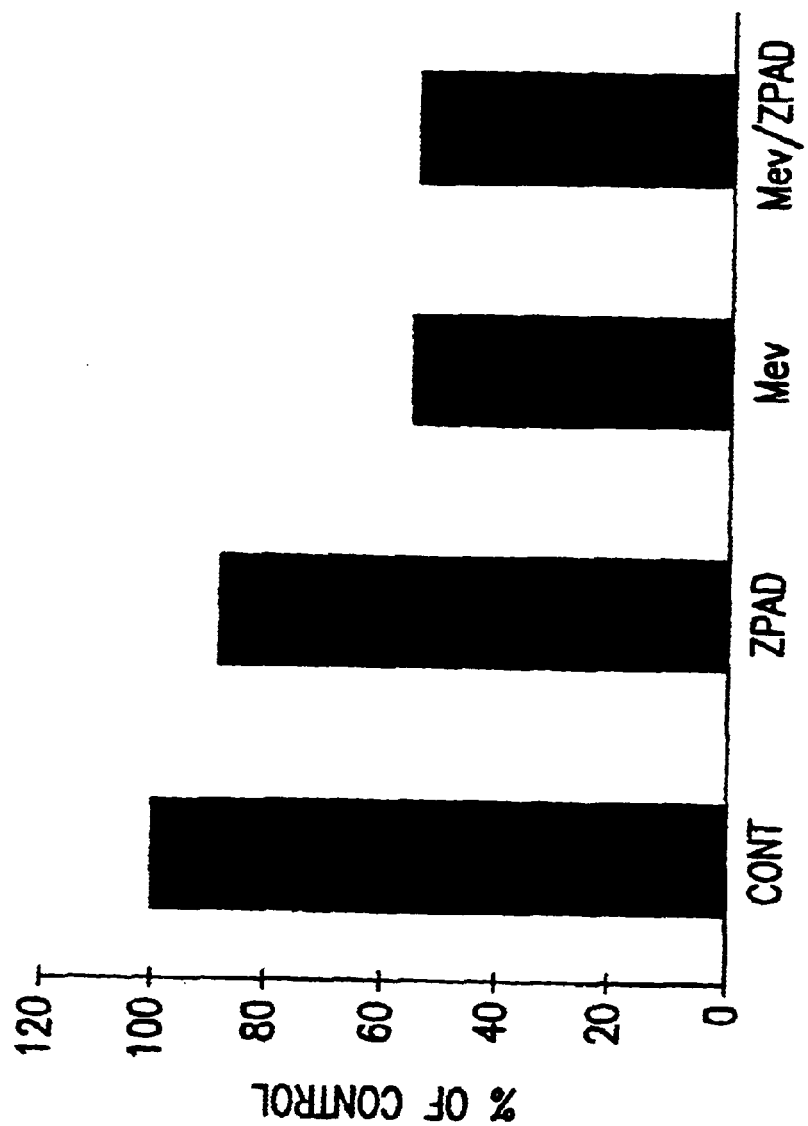

FIG. 13. Level of cdk5 regulatory unit p35 is reduced by mevastatin treatment. Hippocampal slices cultured in vitro for 12 days were treated with vehicle only (control), ZPAD, mevastatin (Mev), or mevastatin plus ZPAD (Mev/ZPAD) for 6 days, and Western blots were stained with anti-p35 antisera. Shown are analytical data from two separate experiments.

FIGS. 14A and 14B illustrate the dose response and time course of p35 following mevastatin(♦) or mevastatin plus ZPAD (■) treatment. For the dose curve experiments, slices were subjected to mevastatin for 6 days at 0 μM, 1 μM, 5 μM, 10 μM, and 100 μM concentrations (A). For the time course experiments, hippocampal cultures were incubated with 10 μM mevastatin for 0, 2, 4, and 6 days. In the mevastatin plus ZPAD treatment, ZPAD was used at 20 μM (B).

Figure 15:
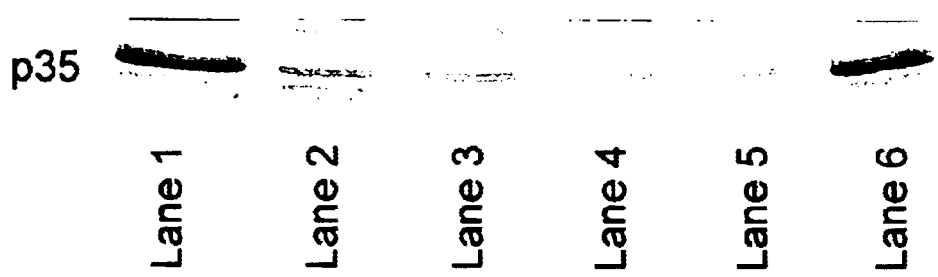

FIG. 15. Down regulation of p35 by mevastatin is blocked by the application of mevalonate. Hippocampal slices were incubated with vehicle alone/control (lane 1), mevastatin (lane 2), mevastatin plus ZPAD (lane 3), mevastatin plus EA1 (lane 4), mevastatin plus cholesterol (lane 5), or mevastatin plus mevalonate (lane 6).

Figure 16:
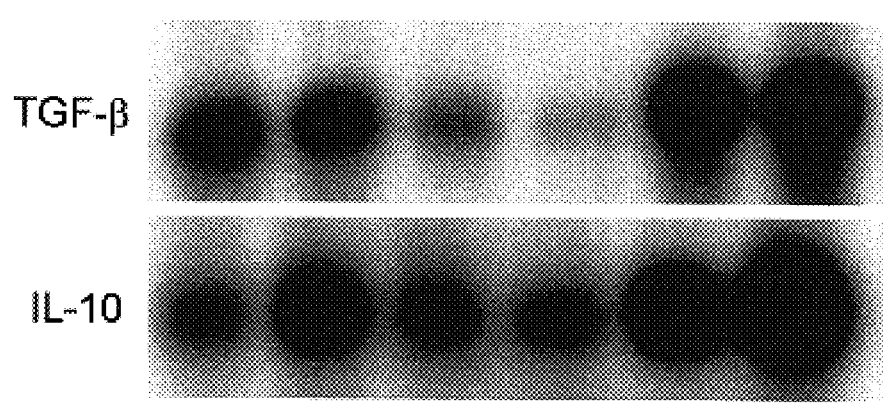

FIG. 16. Messenger RNA levels of TGF-beta and IL-10 are increased by lysosomal dysfunction and interruption of cholesterol synthesis. Messenger RNAs were extracted from cultured hippocampal slices that had been incubated with vehicle (Cont), ZPAD (20 μM), PD98059-a mitogen-activated protein kinase inhibitor (PD98), PD98059 plus ZPAD (PD98/ZPAD), mevastatin (Mev, 20 μM), or mevastatin plus ZPAD (Mev/ZPAD), respectively (each contained 12 slices) and measured by RT-PCR/northern blot techniques using a kit from Ambion Inc. Shown are representatives from three experiments.

Figure 17:
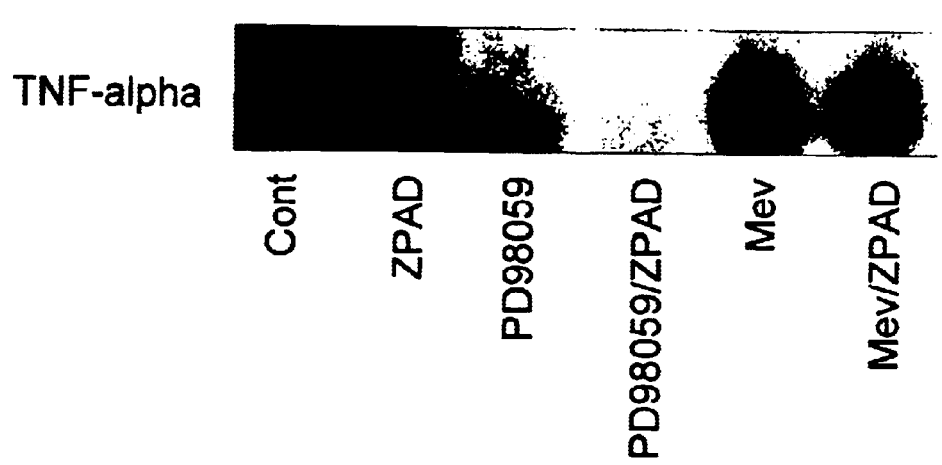
Figure 18A:
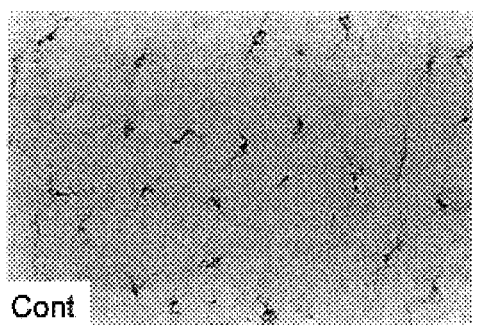
Figure 18B:
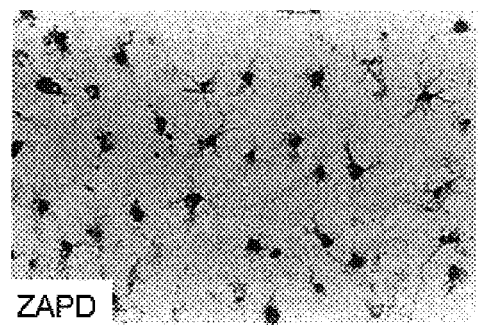
Figure 18C:
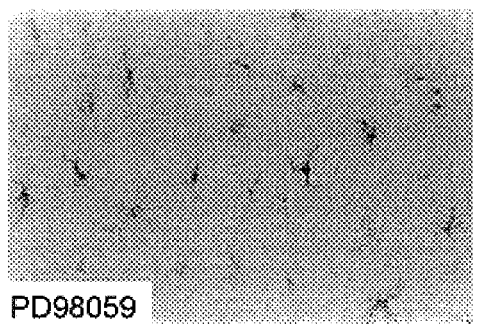
Figure 18D:
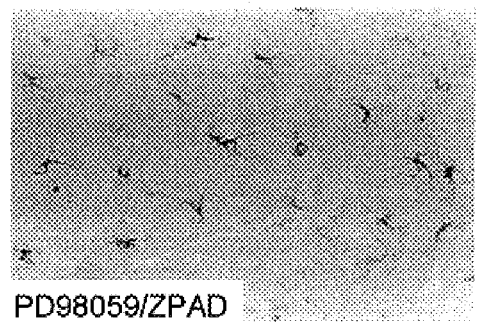
Figure 19A:
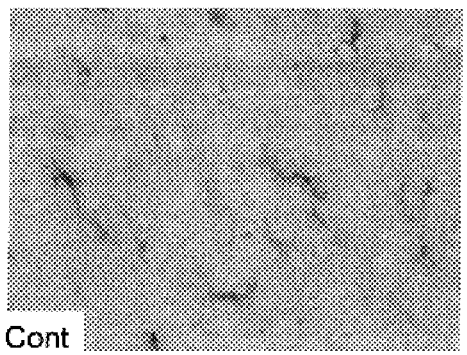
Figure 19B:
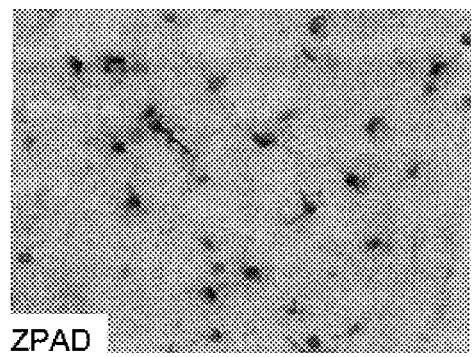
Figure 19C:
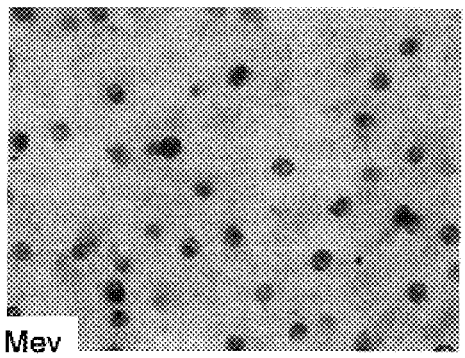
Figure 19D:
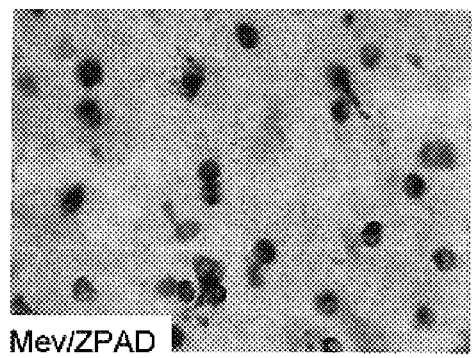

FIG. 17. Messenger RNA levels of TNF-alpha are increased by interruption of cholesterol synthesis. Messenger RNAs were extracted from cultured hippocampal slices that had been incubated with vehicle alone (Cont), ZPAD (20 µM), PD98059 (PD98, 50 µM), PD98059 plus ZPAD (PD98/ZPAD), mevastatin (Mev, 20 µM), or mevastatin plus ZPAD (Mev/ZPAD), respectively (each contained 12 slices) and measured by RT-PCR/northern blot techniques using a kit from Ambion Inc.

FIG. 18. Activation of MAPK is involved in lysosomal dysfunction induced microglial reaction. Brain tissue was cultured for 12 days and treated with vehicle alone (control), ZPAD (20 µM), PD98059 (50 µM) or PD98059 and ZPAD (PD98059/ZPAD) for 6 days. Cultured explants were then sliced and stained by using monoclonal antibody ED-1 which recognizes reactive microglia, a classical marker of inflammation. Note that incubation with ZPAD triggered significant reaction of microglia, and this reaction was completely blocked by co-application of PD98059. Inhibition of MAPK by itself did not induce evident change in microglia.

FIG. 19. Inhibition of cholesterol synthesis causes activation and transformation of microglia. Rat brain tissues were cultured for 10 days and incubated with vehicle (Cont), ZPAD (20 µM), mevastatin (Mev, 20 µM), or mevastatin plus ZPAD (Mev/ZPAD) for 6 days. Cultured brain explants were then sliced and stained by using monoclonal antibody ED-1.

Figure 20:
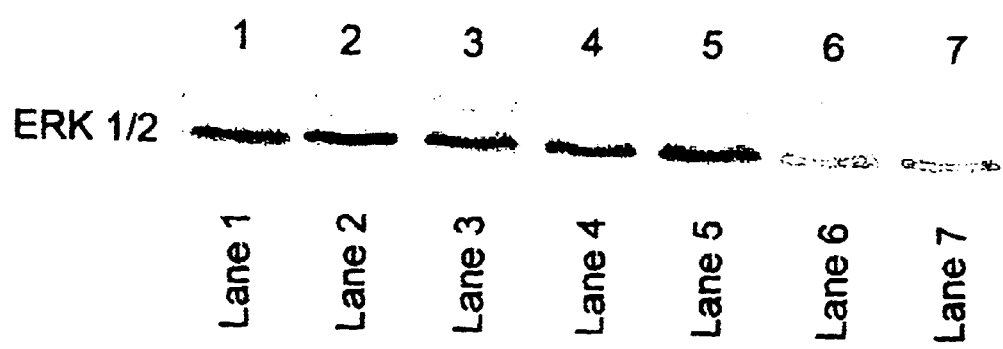

FIG. 20. MAPK (ERK1/2) activation by ZPAD and mevastatin treatment. Hippocampal slices were cultured for 10 days and incubated with vehicle (lane 1), ZPAD (lane 2), mevastatin (lane 3), PD98059 (lane 4), mevastatin plus ZPAD (lane 5), mevastatin plus PD98059 (lane 6) and mevastatin plus ZPAD and PD98059 (lane 7) for 6 days and processed for immunoblot with anti-active MAPK (Sigma, 1:10,000).

Figure 21A:
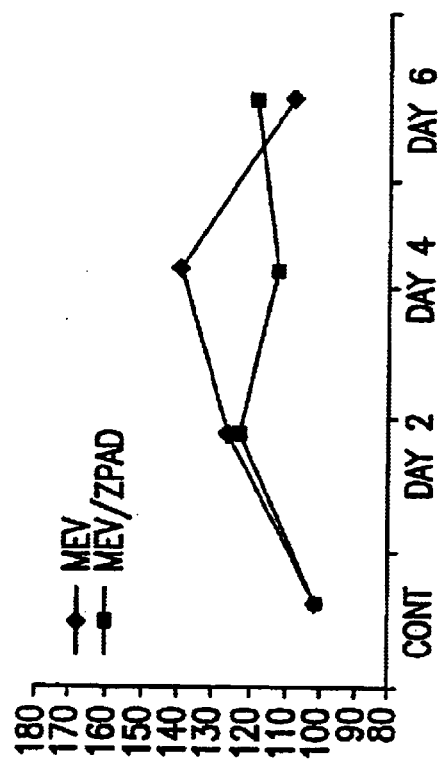
Figure 21B:
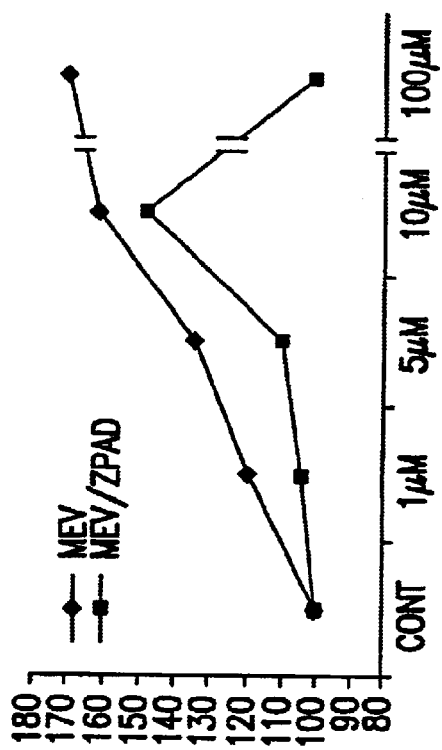

FIGS. 21A and 21B. Dose response and time course of MAPK following mevastatin treatment. Cultured hippocampal slices were treated with mevastatin (♦) or mevastatin plus ZPAD (■). For the dose curve experiments, slices were subjected to mevastatin for 6 days at 0 µM, 1 µM, 5 µM, 10 µM, and 100 µM concentrations (A). For the time course experiments, hippocampal cultures were incubated with 10 µM mevastatin for 0, 2, 4, and 6 days (B).

Figure 22:
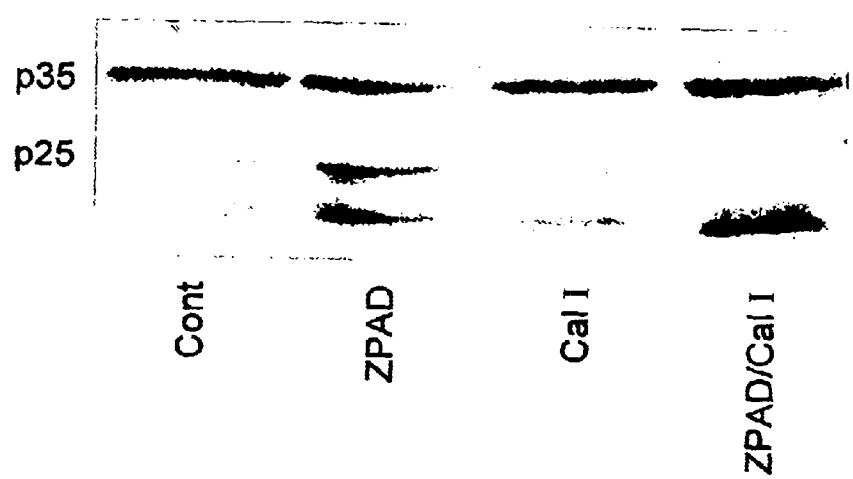

FIG. 22 illustrates that experimentally-induced lysosomal dysfunction induced the conversion of p35 to p25, and that such conversion was blocked by calpain inhibitors. Hippocampal slices prepared from rats at postnatal 10 day and cultured for 12–14 days were incubated with vehicle alone (Cont), ZPAD, a cysteine protease inhibitor (Cal I) or ZPAD plus a cysteine protease inhibitor (ZPAD/Cal I) for 6 days. Immunoblotting carried out using antisera that recognizes the C-terminal domain of p35 showed that the CDK5 binding protein p35 was present in cultured hippocampal slices. Trace amount of p25, the truncated form of p35 that lacks the N-terminal domain, was also detected. A six day treatment of the brain cells, or brain tissue containing the same, with ZPAD resulted in a significant decrease in the amount of p35 polypeptide and a paralleled increase in the truncated form p25. Such conversions of p35 to p25 were significantly inhibited in the presence of calpain inhibitor I.

Figure 23:
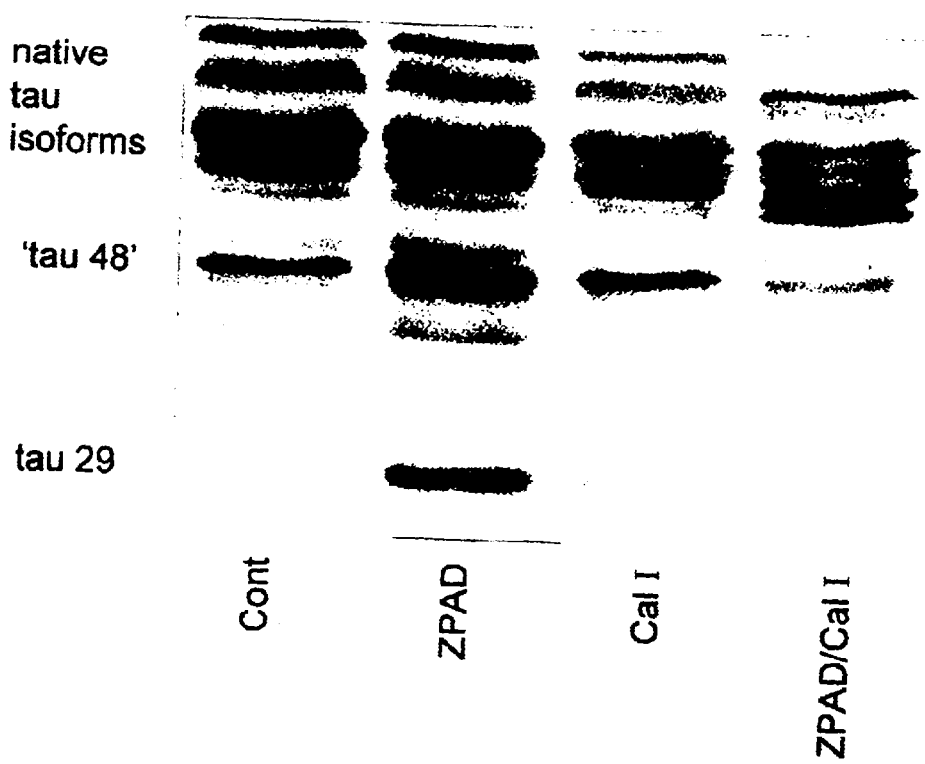

FIG. 23 illustrates that tau fragmentation events triggered by experimentally induced lysosomal dysfunction were blocked by calpain inhibitors. Immunoblots stained with the anti-non-phosphorylated antibody (tau 1), revealed that 6-day treatment with vehicle alone (Cont), ZPAD, a cysteine protease inhibitor (Cal I) or ZPAD plus a cysteine protease inhibitor (ZPAD/Cal I) induced a cleavage of native tau proteins and the generation of tau fragments that migrated at approximately 40 kDa and 29 kDa (tau 29). Previous studies have shown that cathepsin D is a protease whose activation leads to the cleavage of tau and the generation of tau 29. Incubation of cathepsin D inhibitors remarkably reduced the production of tau 29 induced by ZPAD treatment, but the cathepsin D inhibitors failed to block the increase in the 40 kDa fragments. Such results suggested that another protease may be activated by the ZPAD treatment. Previous study had suggested that calpain was able to cleave tau and generate tau fragments of different length. To test whether calpain is involved in ZPAD-induced tau cleavage, levels of tau fragmentation were compared between slices incubated with and without calpain inhibitors. Results obtained from 16 slices of 2 separated experiments showed that ZPAD-induced tau 29 and tau 40 were almost completely blocked by calpain inhibitor I.

Figure 24A:
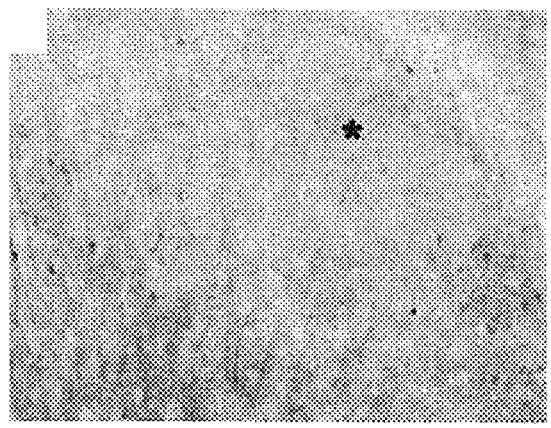
Figure 24B:
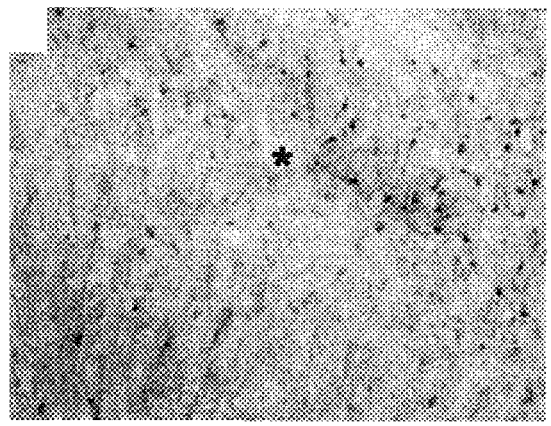
Figure 24C:
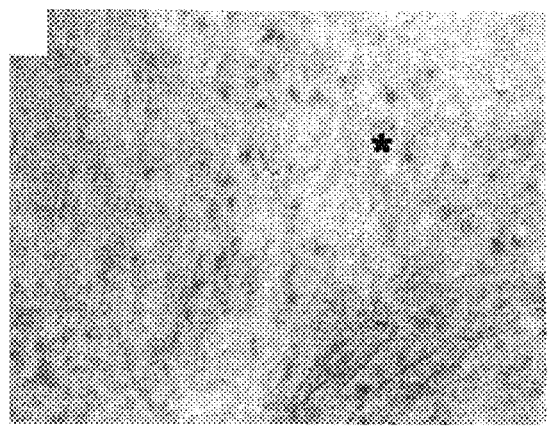

FIG. 24 illustrates that the induction of tangle-like structures by ZPAD-treatment was blocked by calpain inhibitors. Hippocampal slices were incubated with vehicle alone (A), ZPAD (B) or ZPAD plus calpan inhibitor I (C) for 6 days. Incubation of hippocampal slices with ZPAD induced numerous tangles, in particular, in the border of subiculum and CA1 region. However, when ZPAD was applied in the presence of calpain inhibitor I, the number of tangles was significantly reduced.

Figure 25A:
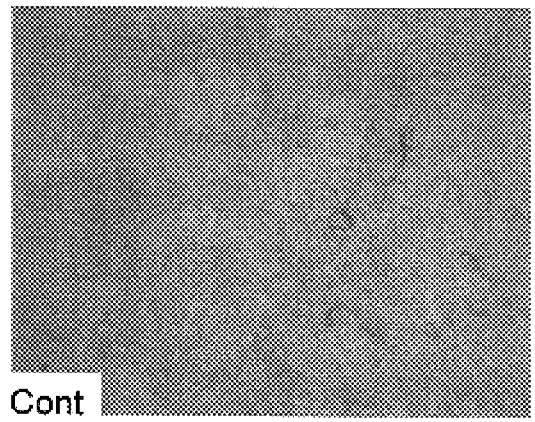
Figure 25B:
Figure 25C:
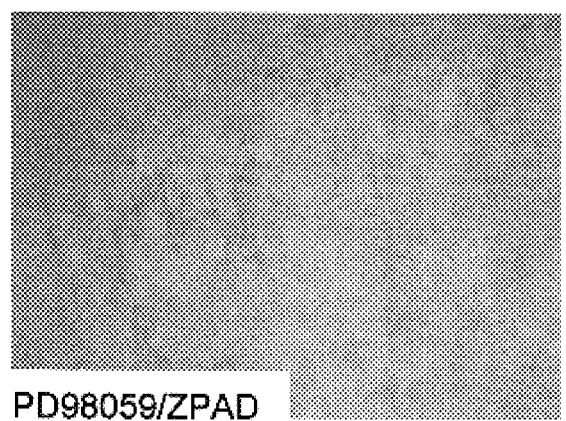

FIG. 25 illustrates that the induction of tangle-like structures by ZPAD treatment was blocked by mitogen activated kinase inhibitors. Hippocampal slices were incubated with vehicle alone (A), ZPAD (B) or ZPAD plus a mitogen activate kinase inhibitor (PD98059) (B) for 6 days. Incubation of hippocampal slices with ZPAD induced numerous tangles, in particular, in the border of subiculum and CA1 region. However, when ZPAD was applied in the presence of a mitogen activated kinase inhibitor, the number of tangles was significantly reduced.

Figure 26:
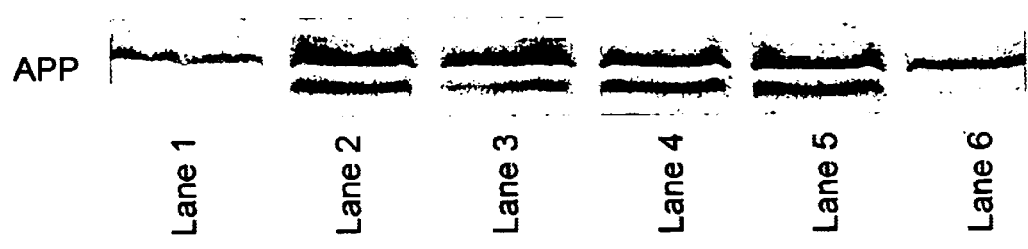

FIG. 26. Modulation of biological processing of amyloid precursor protein by mevastatin treatment is blocked by mevalonate. Hippocampal slices were incubated with vehicle alone/control (lane 1), mevastatin (lane 2), mevastatin plus ZPAD (lane 3), mevastatin plus EA1 (lane 4), mevastatin plus cholesterol (lane 5), or mevastatin plus mevalonate (lane 6).

Figure 27:
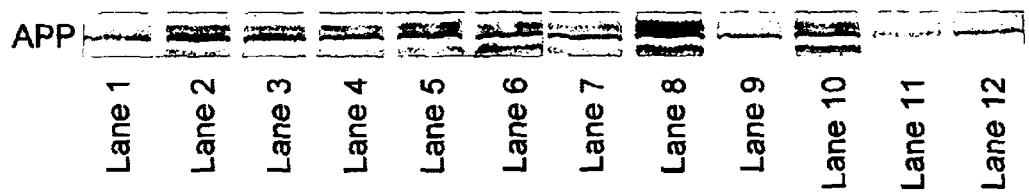

FIG. 27. Effects of mevastatin on APP were partially blocked by MAPKK inhibitor PD98059 but not by inhibitor SB203580 of MAPK p38. Hippocampal slices were incubated with vehicle alone/control (lane 1), mevastatin (lane 2), mevastatin plus ZPAD (lane 3), mevastatin plus PD98059 (lanes 4 and 5), mevastatin plus EA1 (lanes 6 and 7), mevastatin plus cholesterol (lane 8), mevastatin plus mevalonate (lanes 9 and 12), mevastatin plus SB203580 (lane 10), or mevastatin plus γ-secretase inhibitor (lane 11).

Figure 28:
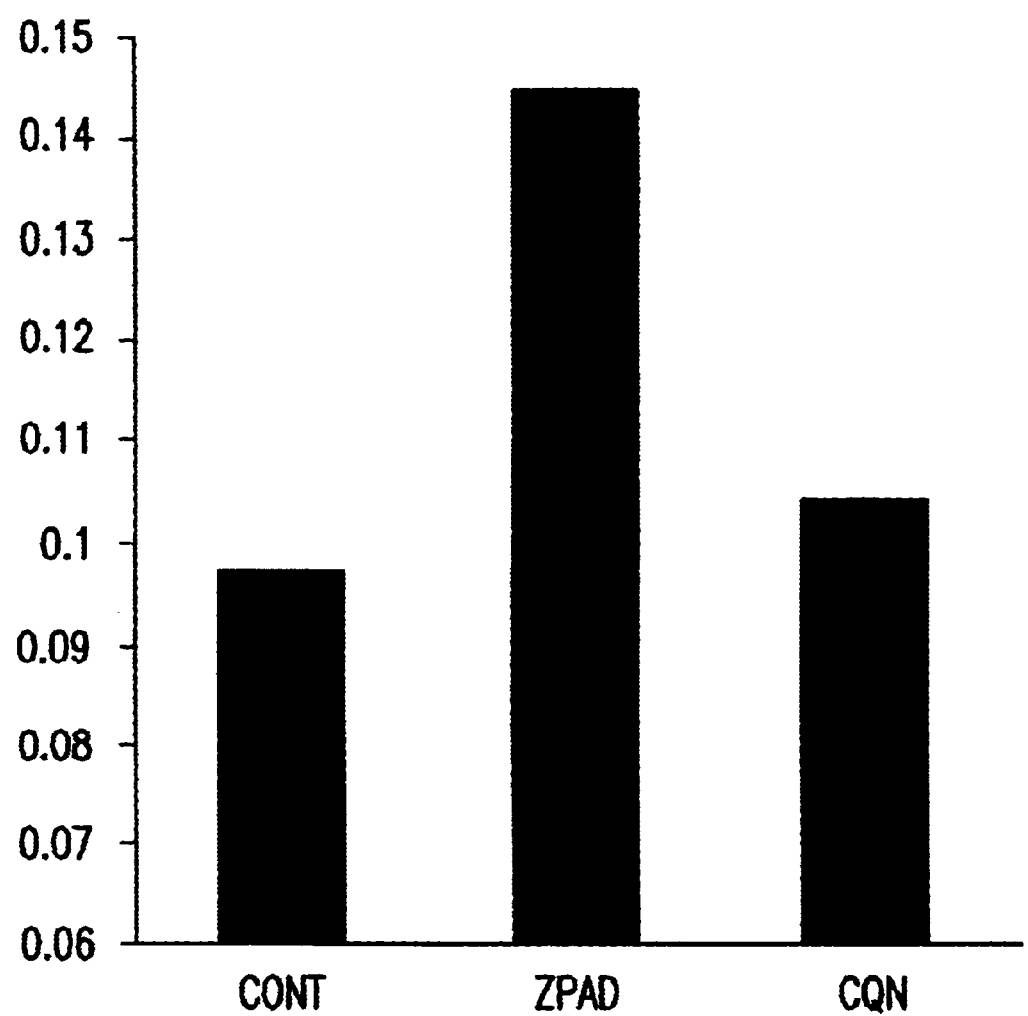
Figure 29A:
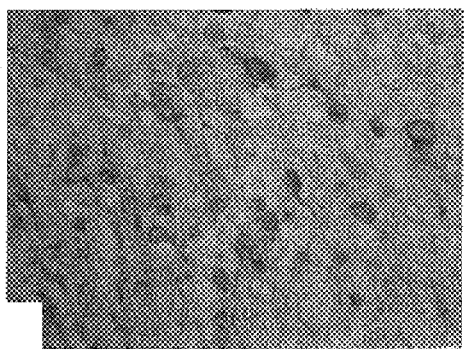
Figure 29B:
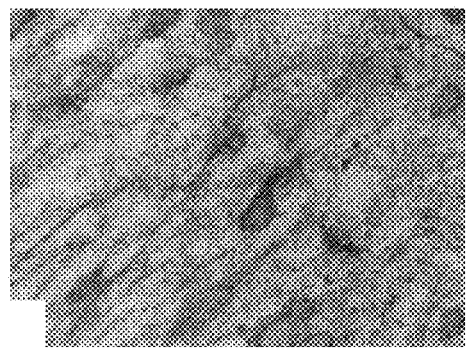
Figure 29C:
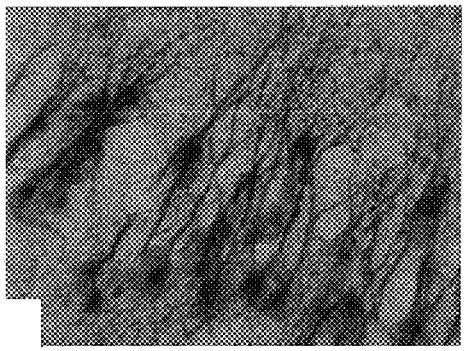
Figure 29D:
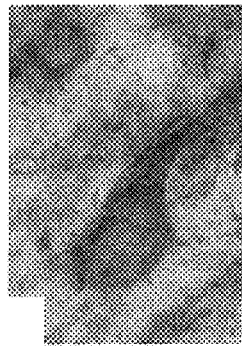
Figure 29E:
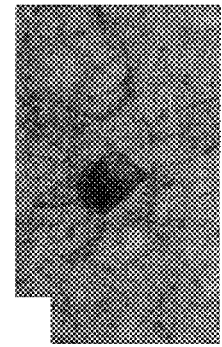

FIG. 28 shows the activation of caspase 3 by lysosomal dysfunction. Hippocampal slices were cultured for 12 days and incubated with vehicle alone (CONT), ZPAD, or chloroquine (CQN; a lysosomal inhibitor) for 6 days. Cultures were then homogenized, and subjected to an ELISA assay to detect the activity of caspase 3, an apoptotic protease. ZPAD treatment caused a marked increase in the activity of caspase 3.

FIG. 29. Induction of tangle-like structures by pravastatin treatment. Shown are images taken form pravastain-treated hippocampal slices from the subiculum (A), CA1 field (B), and CA3 field (C). Also shown are higher magnification micrographs of neurons from the CA1 field (D and E).

Figure 30A:
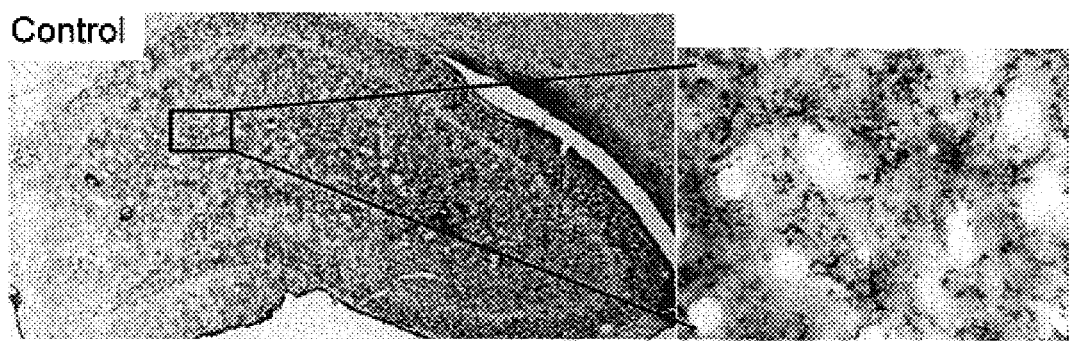
Figure 30B:
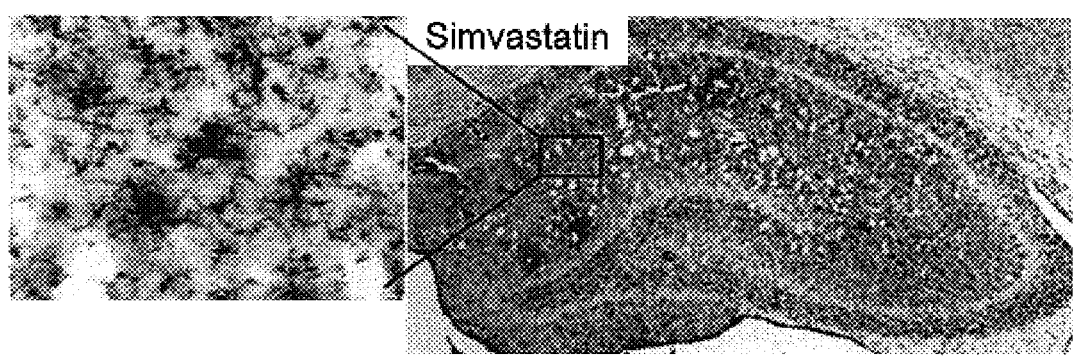

FIG. 30. Induction of microglial reactions by mevastatin and simvastatin treatments. Shown are images of hippocampal areas from one control animal and an animal treated with simvastatin. CD11b immunostaining is moderate in control tissue, while it is generally dense in simvastation treated hippocampus. Higher magnification images show that the density of microglia is higher in simvasatin treated tissue than that in the control tissue.

DEFINITIONS

As used herein, the following terms have the meanings ascribed to them unless specified otherwise.

The term "activation" when used to refer to microglial may refer to a transformation of the microglial, for example, from a silent/quiet (slim cell body with ramified thin process) state to an active/macrophage-like (rounded cell body without process) state. Additionally, the term may refer to an enhanced ability to express and secrete cytokines.

"Alzheimer's disease" specifically refers to a condition associated with: 1) the formation of neuritic plaques comprising amyloid beta protein and/or neurofibrillary tangles comprising tau proteins (primarily located in the hippocampus and cerebral cortex) and, 2) an impairment in both cognitive and non-cognitive functions, for example, impairment in learning and memory, emotion, and coordination. "Alzheimer's disease" as used herein includes all kinds of Alzheimer's disease, including, e.g., early onset family type Alzheimer's disease and late onset sporadic Alzheimer's disease.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., a carbon that is bound to a hydrogen, a carboxyl group, an amino group, and an R group. Examples of amino acid analogs include homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes (A, T, G, C, U, etc.).

"Antibody" refers to a polypeptide substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., Fab' and F(ab)'2 fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, $CH_1$, $CH_2$ and $CH_3$, but does not include the heavy chain variable region. Antibodies that specifically bind to neurofibrillary tangles, phosphorylated tau and/or tau fragments can be prepared using any suitable methods known in the art. See, e.g., Coligan, Current Protocols in Immunology (1991); Harlow & Lane, supra; Goding, Monoclonal Antibodies: Principles and Practice (2d ed. 1986); and Kohler & Milstein, Nature 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275–1281 (1989); Ward et al., Nature 341:544–546 (1989)). Specific polyclonal antisera and monoclonal antibodies will usually bind with a $K_d$ of at least about 0.1 mM, more usually at least about 1 $\mu$M, preferably at least about 0.1 $\mu$M or better, and most preferably, 0.01 $\mu$M or better.

An "anti-phosphorylated tau protein (or anti-phosphorylated tau fragment) antibody" is an antibody or antibody fragment that specifically binds a phosphorylated form of tau protein or its fragment (and not to the unphosphorylated form). In particular anti-phosphorylated fragment antibodies recognize tau fragments that have a molecular weight of about 15–35 kDa, for example, 25–30 kDa. Preferably, antibody that specifically binds to a fragment of tau, such as, for example, tau 29, and especially preferably to a tau fragment having a molecular weight of about 33 kDa is used in embodiments of the invention.

An "anti-neurofibrillary tangle antibody" is an antibody or antibody fragment that specifically binds to any component of the neurofibrillary tangle, e.g., phosphorylated tau and/or tau fragment.

The terms "Apolipoprotein E" and "apoE" refer to a protein that is about 299 amino acids in length and has a molecular weight of about 34,000 Daltons, and plays a major role in lipid transport and metabolism. Specifically, apoE functions as a cholesterol transport protein within the periphery. ApoE is produced in abundance in brain and apoE-containing lipoproteins are the principal lipoproteins in the Cerebro-Spinal Fluid (CSF). In the periphery, apoE expression is dramatically up-regulated in response to peripheral nerve injury. A similar role for apoE in the central nervous system (CNS) has been described whereby apoE distributes cholesterol and phospholipids to neurons after injury. In normal rodent brain apoE is primarily localized to glial cells, whereas in normal human brain apoE has been demonstrated in glia and neurons. After brain injury, intraneuronal apoE is markedly increased in both rodent and human brain. ApoE acts as a ligand for receptors on neurons. The terms "apolipoprotein E" and "apoE" are generically used to refer to either apolipoprotein E protein or gene, and also the terms can refer to any homologs from rat, mouse, rabbit, guinea pig, etc., and their variants.

In humans, three common isoforms of apoE (i.e., apoE2, apoE3, and apoE4) are encoded by the different alleles 2, 3, and 4. The three different apoE isoforms differ only by a single amino acid: apoE2 (cys112, cys158), apoE3 (cys112, arg158) and apoE4 (arg112, arg158). In vitro studies indicate that the three apoE isoforms have differences. Especially, there is a difference in the ability of apoE3 and apoE4 to stimulate neurite outgrowth, bind to amyloid protein, bind to cytoskeletal proteins such as tau and microtubule associated proteins and protect against oxidative stress. In general the apoE4 isoform has a detrimental effect when compared to the apoE3 isoform. For example, in vitro experiments showed that apoE and apoE3 were able to bind to microtubules and form stable complexes with the microtubule associated proteins tau and MAP2c while apoE4 was lacking this ability (Strimmatter et al., *Exp. Neurol.* 125:163–171 (1994)). Current evidence has also identified the apoE4 allele as a major risk factor for sporadic and familial late-onset Alzheimer's disease as well as poor clinical outcome after certain forms of brain injury including that due to head trauma and spontaneous intracerebral hemorrhage. By contrast, possession of an apoE2 has been shown to protect against, or delay the onset of, Alzheimer's disease.

The terms "apolipoprotein E4" or "apoE4" refer to apolipoprotein E4 or polymorphic variants, alleles, interspecies homologs, or conservatively modified variants thereof. The terms "apolipoprotein E4" and "apoE4" are generically used to refer to either apolipoprotein E4 protein or gene, as appropriate to the context. Preferably, apoE4 is from a mammal, e.g., rat, mouse, human, rabbit, guinea pig, etc., and their variants. The nucleotide and amino acid sequences of apoE4 is well-known in the art. For example, the human apoE4 gene is known and has the Genbank accession number of M10065.

"Apolipoprotein E4 containing brain cells, or brain tissue containing the same," or "apoE4 -containing brain cells, or brain tissue containing the same," refer to brain cells, or brain tissue containing the same, that can express apolipoprotein E4 proteins and/or contain the apoE4 gene, as will be determined from the context. Typically, apoE4-containing brain cells, or brain tissue containing the same, are derived from a transgenic animal that comprises an exogenous apoE gene, e.g., a human apoE4 gene, polymorphic variants, alleles, interspecies homologs, or conservatively modified thereof, which encode an apoE4 protein. The methods for producing these transgenic animals are well-known in the art and described in, e.g., U.S. Pat. No. 6,046,381.

"Brain cells" refers to cells and/or tissue containing the same. Brain cells can be derived from any brain. For example, for use in the methods of the invention, brain cells, or brain tissue containing the same, can be those in or from a normal animal, an apoE-deficient animal, or an apoE4-containing animal. Preferably, brain cells, or brain tissue containing the same, are derived from a mammal, such as a rat, mouse, guinea pig, rabbit, etc. or transgenic animals with modulated levels of neurofibrillary tangles, and/or tau proteins, and/or amyloid, and/or amyloid precursor proteins, and/or Cathepsin D levels, and/or cysteine protease levels, and/or mitogen activated kinases, and/or lysosomal enzyme levels, and/or cholesterol levels and/or altered cholesterol metabolism, synthesis, storage, etc. The pathology modeling and drug testing brain cell embodiments of the invention can be carried out in animal models in vivo or in vitro. When provided in an embodiment in which the cells are cultured in vitro, unless otherwise indicated, the brain cells, or brain tissue containing the same, can be provided in any in vitro form capable of culture, for example, brain tissue that contains cells, or brain sections such as slices that contain cells, dissociated cells, cells bound to a solid support or in suspension, etc.

"BLAST" and "BLAST 2.0" are programs that are used, with the parameters described herein, to determine percent sequence identity for the nucleic acids and proteins of the invention. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands. The BLAST algorithm also performs a statistical analysis of the similarity between two sequences (see, e.g., Karlin & Altschul, *Proc. Nat'l. Acad. Sci. USA* 90:5873–5787 (1993) ). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Calpain is a cysteine protease found in brain cells. There are two major isoforms of calpain in the brain, μ-calpain (also known as calpain I) and m-calpain (also known as calpain II). The two calpains differ in their calcium requirements but have similar substrate specificities. Calpain activity can be assayed by following the cleavage of α-spectrin as described in WO 00/21550.

Cathepsin D is a lysosomal protease which is found in the brain, along with other lysosomal proteases, such as cathepsin B and cathepsin L. The activities of these proteases change in the brain with aging. For example, the activity of cathepsin L decreases by up to 90% during brain aging, while the levels and activity of cathepsin D increase. See Nakanishi et al., *Exp. Neurol.* 126:119–128 (1994). Moreover, the activities of these cathepsin proteases are inter-related. For example, it was previously reported that inhibition of cathepsin B and L increases procathepsin D and its maturation into the active two-chain form (composed of heavy and light chain) within lysosomes. See Bednarski & Lynch, *Neuroreport* 9:2089–2094 (1998); Hoffman et al., *Neurosci. Lett.* 250:75–78 (1998). "Cathepsin D" typically exists in three forms: the inactive proenzyme having an apparent molecular weight of about 55 kDa; the active single chain having an apparent molecular weight of about 50 kDa; and the active double chain form that consists of a heavy chain having an apparent molecular weight of about 38 kDa and a light chain of about 14 kDa.

"cholesterol-lowering agent" is a compound or other substance that, at effective levels, depresses the levels of cholesterol in the brain cells of the invention. The agent may inhibit the activity or amount of HMG-CoA reductase (an enzyme involved in cholesterol synthesis in cells) and/or other entities involved in cholesterol synthesis, degradation, storage, and/or transport.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide of interest is implicit in each described sequence. As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants and alleles of the invention.

The following groups each contain amino acids that are conservative substitutions for one another:

1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L), Valine (V); and
8) Phenylalanine (F), Tyrosine (Y), Tryptophan (W). (see, e.g., Creighton, Proteins (1984) for a discussion of amino acid properties).

"comparison window", as used herein, includes reference to a segment of any one of the number of contiguous amino acid or nucleotide positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)). A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively.

The term "control" refers the non-treated condition or substance. For example, when examining the effect of a compound on its ability to increase cathepsin D in brain cells, "control" brain cells could be brain cells that have not been treated with that compound, or brain cells assayed at the beginning of the experiment (time=zero) before any compound-induced changes thereto, as will be clear from the context. In another example, as will be clear from the context, in some embodiments directed to apoE-deficient brain cells or apoE4-containing brain cells, the term "control" brain cells can also refer to normal brain cells (comprising a wild-type or endogenous apolipoprotein E gene) which have been treated with a compound that increases an effective concentration of cathepsin D in the brain cells.

The term "deficient" refers to a decreased or lower amount of the indicated substance. For example, apolipoprotein E "deficient" brain cells, or apoE "deficient" brain cells refer to brain cells that contain less endogenous apolipoprotein E as compared to brain cells having wild-type apolipoprotein E genes (for example, normal brain cells) measured or cultured under similar conditions. The term deficient may also refer to a variant that has an altered function, for example, brain cells that are "deficient" in apoE may contain a variant of apoE that has an altered function, e.g., in lipid transport, as compared to wild-type apoE-such altered function not being able to substitute for the unaltered function.

By neuronal "degeneration" is meant that one or more characteristics as described herein as being indicative of a decline of brain functioning have appeared, are present or accumulated over time in the brain cells, especially changes in neuronal tau protein levels or structure (tau phosphorylation, tau proteolysis, tau fragments, etc) as compared to such characteristics in normal neurons.

"Disorder" and "disease" refer to any disorder, disease, condition, syndrome or combination of manifestations or symptoms recognized or diagnosed as a disorder. If modified by reference to a particular disease or by reference to one or more or a set of manifestations or symptoms, that usage of "disorder" or "disease" refers to any such disorder, disease, condition, syndrome or combination of such manifestations or symptoms recognized or diagnosed as a such disorder.

The term "effective," as in an "effective concentration of cathepsin D" or an "effective concentration of cholesterol" refers to either an amount or an activity of the indicated substance or condition that is sufficient to achieve the indicated purpose. For a first example, an effective concentration of cathepsin D to induce neurofibrillary tangles and/or tau fragmentation, etc. refers to an amount of cathepsin D or a level or enzymatic activity of cathepsin D that is sufficient to increase the level of neurofibrillary tangles, and/or tau fragmentation within a desired period of time. In a second example, decreasing an effective concentration of cholesterol to induce neurofibrillary tangles and/or tau fragments refers to an amount of cholesterol or a level or activity of agents which synthesize, store, and or transport cholesterol that is sufficient to increase the level of neurofibrillary tangles and/or tau fragments within a desired period of time.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, preferably 75%, 80%, 85%, 90%, or 95% identity or higher over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length. In most preferred embodiments, the sequences are substantially identical over the entire length of, e.g., the coding region. For sequence comparison, typically one sequence acts as a reference sequence, to which test sequences are compared. When using a sequence comparison algorithm, test and reference sequences are entered into a computer, subsequent coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "immunoassay" is an assay that uses an antibody to specifically bind an antigen. The immunoassay is characterized by the use of specific binding properties of a particular antibody to isolate, target, and/or quantify the antigen."

By "inducing" a characteristic in a brain cell is meant that the characteristic appears in the cell, or levels (or the enzymatic activity) of such characteristic are increased in the cell, after treatment with the desired agent. By "enhancing" a characteristic in a brain cell is meant that the levels (or the enzymatic activity) of the indicated characteristic are increased in the cell after treatment with the desired agent.

By "lysosomal function" is meant any activity, enzymatic or non-enzymatic, that is a property of the lysosomes, including vesicle trafficking to or from lysosomes, the endocytic pathway, heterophagy or autophagy, and including the expression and activity of enzymes that are localized in the lysosomes. By "inhibiting or suppressing a lysosomal function" is meant lowering or decreasing one or more such activities from the level or amount of such activity found in the non-inhibited or non-suppressed state, including inhibiting or suppressing vesicle trafficking to or from lysosomes, and including inhibiting or suppressing the expression or activity of a lysosomal enzyme. Such inhibition or suppression can be acute or chronic. Examples of lysosomal enzymes that can be inhibited or suppressed include a lysosomal acid hydrolase, lysosomal protease, lysosomal nuclease, lysosomal lipase, amylase and a cathepsin. Cathepsin B, cathepsin H or cathepsin L can be assayed using methods known in the art, for example, as described by Barrett, A. J. et al., *Meth. Enzymol.* 80:535 (1981), Academic Press, New York, incorporated herein by reference.

"Lysosomal dysfunction" means an abnormal lysosomal morphology, chemistry or activity, which is detrimental to lysosomes or cells. Examples of lysosomal dysfunctions include a detrimental change, either increased or decreased, in the normal activity of the endocytic pathway, a detrimental change in lysosomal morphology, a detrimental change in the intra-lysosomal pH, and/or the activity(ies) of lysosomal enzyme(s).

"Neurodegenerative diseases" includes almost all disease in central nervous system accompanied by neuronal degeneration including, for example, age-related neurodegenerative diseases, Alzheimer's disease, frontotemporal dementias, frontotemporal dementia and Parkinsonism, Huntingon's Disease, ischemia, Pick's disease, Progressive supranuclear palsy pathology, Parkinson's Disease, senile dementia, stroke, etc.

"Neurofibrillary tangles" refer to intraneuronal accumulations of filamentous material in the form of loops, coils or tangled masses. Neurofibrillary tangles seen in brain cells are sometimes referred to herein as "tangle-like structures."

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated.

The term "pharmaceutically effective amount" refers to an amount sufficient to alleviate, in any degree or manner, one or more of the manifestations or symptoms recognized or diagnosed as associated with the modifying disorder, the modifying manifestations, or the modifying symptom.

The term "phosphorylated tau" includes all forms of tau that have been phosphorylated, including hyperphosphorylated tau and "abnormally" phosphorylated tau. Hyperphosphorylated tau is phosphorylated at both Ser/Thr-Pro and non-Ser/Thr-Pro as compared to tau in normal tau. In general phosphorylated tau is rare in mature brain tissues, although there are phosphorylated forms in developing immature tissues. Thus, phosphorylation of tau in mature tissue by itself is already abnormal, and such forms of tau are also referred to as "hyperphosphorylated" tau or as "abnormally" phosphorylated tau. Moreover, some sites are typically only found phosphorylated in the phosphorylated form in tau that is in neurofibrillary tangles, such as Ser 202 (as exemplified herein below as a marker), Ser 396 and Ser 404.

Therefore, tau proteins phosphorylated at multiple sites, in particular at those sites found in human neurofibrillary tangles, are also included in the term hyperphosphorylated tau, or abnormally phosphorylated tau.

The terms "polypeptide," "peptide" and "protein" are used interchangeably herein to refer to a polymer of amino acid residues. The terms apply to amino acid polymers in which one or more amino acid residues is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoprotein.

The terms "reduces," "reduced," or "reducing," when used to refer to one or more symptomologies of a disease, refers to any observable or measurable lessening of that characteristic when the method or composition of the present invention is compared to prior art methods or compositions.

The term "reaction" when used to refer to microglial may refer to a transformation of the microglial, for example, from a silent/quiet (slim cell body with ramified thin process) state to an active/macrophage-like (rounded cell body without process) state. Additionally, the term may refer to an enhanced ability to express and secrete cytokines.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The term "selectively" increased or "selectively" decreased means that the activity or amount of the substance that is being "selectively" increased or decreased is increased or decreased, respectively, relative to the activity or amount of such substance prior to an indicated treatment or relative to that of a control, or other substance (if named).

The phrases "specifically binds to" or "specifically immunoreactive with," when referring to a binding moiety refers to a binding reaction which is determinative of the presence of a target antigen in the presence of a heterogeneous population of proteins and other biologics. Binding moeities include any material capable of resolving the presence of tau proteins and/or neurofibrillary tangles, such as antibody, dyes, silver, other contrast agents etc. Thus, under designated assay conditions, the specified binding moieties bind preferentially to a particular target antigen and do not bind in a significant amount to other components present in a test sample. Specific binding to a target antigen under such conditions may require a binding moiety that is selected for its specificity for a particular target antigen. A variety of immunoassay formats may be used to select antibodies that are specifically immunoreactive with a particular protein. For example, solid-phase ELISA immunoassays are routinely used to select monoclonal antibodies that are specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity. Typically, a specific or selective reaction will be at least twice background signal or noise and more typically more than 10 to 100 times background. Specific binding between an antibody or other binding agent and an antigen preferably has a binding affinity of at least $10^6$ $M^{-1}$. Preferred binding agents bind with affinities of at least about $10^7$ $M^{-1}$, and preferably $10^8$ $M^{-1}$ to $10^9$ $M^{-1}$ or $10^{10}$ $M^{-1}$.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C. Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

Two nucleic acid sequences that encode polypeptides are considered to be "substantially related" if the polypeptide encoded by the first nucleic acid is immunologically cross reactive with polyclonal antibodies raised against the polypeptide encoded by the second nucleic acid. Two nucleic acid sequences that encode polypeptides are considered to be "substantially identical" if nucleic acid encoding the first sequence hybridizes to the complement of nucleic acid that encodes the other molecule under stringent conditions, as described below. Yet another indication that two nucleic acid sequences are substantially identical is that the same primers can be used to amplify the sequences. Generally, two polypeptides are "substantially identical" if they share an amino acid sequence identity of at least 85% or differ in sequence only by conservative substitutions.

"Transgenic animal" refers to a non-human animal that comprises an exogenous nucleic acid sequence present as an extrachromosomal element or stably integrated in all or a portion of its cells, especially in germ cells.

DETAILED DESCRIPTION OF THE INVENTION

I. Characteristics of the Neurodegenerative Disease Brain Cells of the Invention, or Brain Tissue Containing the Same The present invention provides a novel method for triggering brain cells, or brain tissue containing the same, to induce the characteristics of a brain cell or tissue from a brain that is afflicted with a neurodegenerative disease. The present invention also provides novel methods for inhibiting or preventing the development of such characteristics of such neurodegenerative disease in the brain cells.

The model of the present invention is based on, in part, the discovery that experimental lysosomal dysfunction, decreases in cholesterol concentration, and especially a combination of both, rapidly induce the formation of one or more brain cell characteristics that are indicative of a decline of neuron functioning and are associated with, and especially in combination, definitive for, neurodegenerative diseases and especially age-related neurodegenerative diseases such as Alzheimer's disease. According to the invention, exposing a brain cell to conditions that increase the concentration of cathepsin D ("cathepsin D-increasing compound"), or exposing a brain cell to conditions that decrease the concentration of cholesterol ("cholesterol decreasing compound"), or both, surprisingly trigger the hyperphosphorylation of the protein tau and tau fragments, the production of neurofibrillary tangles, the production of tau fragments, increases in cytokine activity and levels, microglia activation, and induction of brain inflammatory reactions and other indicia or characteristics of neurodegenerative diseases. Such effects are even more surprisingly enhanced when apoE-deficient or apoE4-containing brain cells, or brain tissue containing the same, are use in the model. Such exposure can come from altering the environmental conditions to which the brain cell is exposed, or, preferably by contacting or treating brain cells, or brain tissue containing the same, with a compound capable of inducing such effective levels of cathepsin D and/or of decreasing the concentration of cholesterol Brain cells, or tissue containing the same, maintained under conditions in which cathepsin D is selectively induced, and/or cholesterol is selectively decreased, are characterized by the de novo appearance and/or accumulation of, one or more characteristics of neurodegenerative diseases in the cells. The accumulation of such characteristics is relative to the levels present in the cells at the start of the treatment or exposure to the indicated condition, and/or relative to the levels present in similar cells not contained with, or otherwise maintained in the absence of, the cathepsin D-increasing compound and/or compounds capable of selectively decreasing cholesterol. Such characteristics include:

(1) the formation of neurofibrillary tangles, (2) the hyperphosphorylation of tau, (3) the fragmentation of tau, that is, tau proteolysis and especially, increased amounts of the 15–35 kDa forms of tau ("tau fragments"), (4) increased production and/or release of brain-produced pro-inflammatory cytokines especially TGF-beta (tumor growth factor beta or TGF1), TGF-alpha, IL1 (interleukin-1), IL1-alpha (interleukin-1alpha), IL1-beta (interleukin-1beta), IL6 (interleukin-6), IL10 (interleukin-10), TNF (tumor necrosis factor), TNF-alpha (tumor necrosis factor alpha) and LPS (lipopolysaccharide), and most especially TGF-beta, IL-1beta and LPS, (5) increased microglia reaction and/or activation, (6) increased indications of brain inflammatory reactions, such as, for example, increased positive staining for HLA-DR (which detects reactive microglia); increased positive staining for glial fibrillary acidic protein (GFAP; to detect reactive astrocytes); the extracellular accumulation of complement proteins, complement inhibitors, acute phase reactants, growth factors, heat shock proteins, proteoglycans, lipoproteins, cathepsins, cystatins, coagulation factors, proteases, protease inhibitors, integrin adhesion molecules, etc., and (7) increased conversion of p35 to p25

(8) changes in the levels and activities of protein kinases, for example, cyclin dependent protein kinase 5 (cdk5) and mitogen activated protein kinase (MAPK).

Additional characteristics useful as an indicator of a brain afflicted neurodegenerative diseases can include, e.g., an increased amount of lysosomes, the appearance of basophilic granules in the mossy fiber terminal zone, the presence of secondary lysosomes with lipofuscin, amyloid deposition, amyloid plaques, neuritic plaques, synaptic loss, neuritic degeneration, neuronal death, increased glial elements (astrocytes, microglia), fragmentation of the amyloid precursor protein, increases in the levels of Cathepsin D, etc.

The above characteristics, and others describe herein, are indicative of a decline of neuron functioning. Such decline may be the result of a direct effect of the characteristic or an indirect effect. Characteristics that are the result of a direct effect are those found in the neurons, for example, an increase in tau phosphorylation or tau proteolysis and fragmentation. Characteristics that are the result of an indirect effect are those that are found in brain cells other than neurons, for example, induction of glial activation.

The first, and most preferable characteristic of brain cells, or brain tissue containing the same, cultured under conditions that selectively increase cathepsin D, and/or that selectively decreases levels of cholesterol, according to the method of the invention is the formation of neurofibrillary tangles in the cells. The formation of neurofibrillary tangles refers to the appearance and/or accumulation of intraneuronal deposits that are composed mainly of paired helical filaments. Generally, such tangles can be seen with light microscopy. The method of the invention is especially characterized by its ability to induce the appearance of "early tangles" in the brain cells, or brain tissue containing the same. "Early tangles" refer to intraneuronal tangles typically found at an early stage of neurodegenerative disease, such as Alzheimer's disease. Under appropriate conditions as described herein, such "early tangles" are typically formed, or enhanced levels are detectable, within a few days of culture or treatment. Such early tangles may appear in the brain cells in any of day 1, 2, 3, 4, 5 or 6, or even beyond, after initiation of the appropriate condition in culture or after administration of the appropriate agent(s) in vivo. Preferably, such early tangles appear 2–6 days in culture embodiments. However, longer periods are acceptable, especially in the in vivo models, because in vivo models are not constrained by the same viability considerations as in vitro models. Morphologically, such tangles mimic early-stage tangles (i.e., intracellular tangles) found in the brain of Alzheimer's patients.

As described above, it was previously shown that neurofibrillary tangles may contribute to the cognitive decline associated with neurodegenerative diseases and may also trigger neuronal cell death in the brain. However, many currently available in vivo and in vitro models of neurodegenerative diseases lack this or other key features associated with brain cells from patients inflicted with these conditions. Thus, the present invention advantageously provides a model brain cell system, wherein the brain cells contain, or can be induced to contain, among other things, neurofibrillary tangles. The appearance and/or disappearance of such tangles, as a result of the presence or absence of various therapeutic candidates or culture conditions, can be monitored and used to assess the value of therapeutic candidates that might be useful for the treatment of such conditions or diseases.

A further characteristic of brain cells maintained according to the method of the invention so as to induce the formation of indicia of neurodegenerative disease is the accumulation of levels (amounts or concentrations) of phosphorylated tau that are greater than levels found in control cells or in the same cells at the beginning of the culture. Phosphorylated tau, and especially abnormally phosphorylated and/or hyperphosphorylated tau, can be assayed in the cells as a whole, or in subfractions, for example, in soluble and/or insoluble fractions thereof, including paired helical filaments.

A further characteristic of brain cells incubated according to the method of the invention so as to induce the formation of neurodegenerative disease indicia is the production or accumulation of greater amounts of proteolytic fragments of tau, and specifically, tau fragments having a molecular weight of 15–35 kDa fragments (tau fragments), when compared to control cells or to the same cells at the beginning of the culture, especially fragments having an apparent molecular weight of 33 or 29 kDa. The 29 kDa tau fragment results from cleavage at amino acids 200–257. Larger fragments may also be seen. For example, the appearance or accumulation of a fragment with an apparent molecular weight of 40 kDa is an indicia of neurodegenerative disease. Such proteolytic products of tau can be unphosphorylated and/or phosphorylated and can include hyperphosphorylated forms. As above, tau fragments can be measured in the cells as a whole, or in soluble and/or insoluble fractions thereof, including paired helical filaments.

A further characteristic of brain cells incubated according to the method of the invention so as to induce the formation of neurodegenerative disease indicia is the increased production and/or release and/or accumulation of brain-produced cytokines especially, TGFb (tumor growth factor-beta, or TGF-beta), IL-1b (interleukin 1 beta) and LPS (lipopolysaccharide), when compared to control cells or to the same cells at the beginning of the culture. As above, cytokines and LPS can be measured in the cells as a whole, or in soluble and/or insoluble fractions thereof, including the medium.

A further characteristic of brain cells incubated according to the method of the invention so as to induce the formation of neurodegenerative disease indicia is increased microglia reaction and/or activation. Microglial reaction and/or activation refers to the fact that when injury or disease affect nerve cells, microglia in the central nervous system become "active," causing inflammation in the brain, similar to the manner in which white blood cells act in the rest of the body. Microglia act like the monocyte phagocytic system. Microglia can be activated by numerous materials including complement proteins and beta amyloid protein. Activated microglia generate large quantities of superoxied anions, with hydroxyl radicals, singlet oxygen species and hydrogen peroxide being a downstream product, any of which can be assayed in the preparations utilized in such methods of the invention. Such microglial activation may be used with other indicia in the model of the invention in the embodiments in which brain architecture is retained to some degree, for example, when a brain slice is employed, or when brain cells are in vivo.

Reactive microglia and astrocytes are characterized by their cell bodies becoming larger, their processes becoming thicker, by an increase in the GFAP and ED-1 staining, by a proliferation and clustering of microglia and astrocytes, by infiltration of peripheral inflammatory cells, for example, white blood cells, and by formation of gliosis, etc., as compared to that found in the non-reactive state.

A further characteristic of brain cells incubated according to the method of the invention so as to induce the formation of neurodegenerative disease indicia is the appearance of increased indications of brain inflammatory reactions. Increased indications of brain inflammatory reactions can include indications such as, for example, increased positive staining for HLA-DR (which detects reactive microglia); increased positive staining for glial fibrillary acidic protein (GFAP; to detect reactive astrocytes); the extracellular accumulation of complement proteins, complement inhibitors, acute phase reactants, growth factors, heat shock proteins, proteoglycans, lipoproteins, cathepsins, cystatins, coagulation factors, proteases, protease inhibitors, integrin adhesion molecules, etc. Such indicia of brain inflammatory reactions may be used with other indicia in the model of the invention in the embodiments in which brain architecture is retained to some degree, for example, when a brain slice is employed, or when brain cells are in vivo.

A further characteristic of brain cells incubated according to the method of the invention so as to induce the formation of neurodegenerative disease indicia is a change in the levels and activities of protein kinases, for example, cyclin dependent protein kinase 5 (cdk5) and mitogen activated protein kinase (MAPK).

To be useful in the methods of the invention, it is not necessary that all of the brain cells in a sample or preparation exhibit at least one of the above characteristics. Rather, such preparations are useful even if only some of the brain cells contained therein exhibit such characteristics. Preparations of brain cells in accordance with embodiments of the invention preferably contain at least some cells that contain neurofibrillary tangles, but not all the cells in the preparation need to exhibit such tangles. In a preferred embodiment, such changes are found in the neurons that are in the brain cell preparations. In another preferred embodiment such changes are found in brain cells in vivo.

Not all the characteristics need to be induced by the same agent or at the same time or to the same degree in preparations intended to induce brain cells to exhibit the characteristics of neurodegenerative diseases. Preferably, upon treatment with the agent that induces lysosomal dysfunction so as to increase cathepsin D, or with the agent that decreases an effective concentration of cholesterol, the brain cell's biochemistry, physiology or morphology is changed to include at least one or more of:

(1) the formation of neurofibrillary tangles, (2) the hyperphosphorylation of tau, and/or (3) the fragmentation of tau, that is, tau proteolysis and especially, increased amounts of the 15–35 kDa forms of tau.

The rest of the characteristics:

(4) increased production and/or release of brain-produced pro-inflammatory cytokines especially TGF-beta, TGF-alpha, IL1, IL1-alpha, IL1-beta, IL6, IL10, TNF, TNF-alpha and LPS and most especially TGF-beta, IL-1beta and LPS, (5) increased microglia reaction and/or activation, (6) increased indications of brain inflammatory reactions, (7) increased conversion of p35 to p25

(8) changes in the levels and activities of protein kinases, for example, cyclin dependent protein kinase 5 (cdk5) or mitogen activated protein kinase (MAPK), are preferably not relied on solely but, if assayed, are assayed along with any of the formation of neurofibrillary tangles,
the hyperphosphorylation of tau, and/or
the fragmentation of tau, that is, tau proteolysis and especially, increased amounts of the 15–35 kDa forms of tau, as indicators of the appearance or disappearance of characteristics of neurodegenerative disease in the methods and cultures of the invention.

Pro-inflammatory cytokines including IL1-alpha, IL1-beta, IL6, and IL10, TNF, TFN-alpha and TGF (alpha or beta), and especially TGFbeta1 (also referred to as TGF1), and TNF-alpha, are useful as indicators of glial activation. Levels of these cytokines, including levels of their mRNAs, can be quantitated, for example, by RT-PCR, to assay for glial activation and lysosomal dysfunction. Assays for such factors are known in the art.

Activation of the MAP kinase pathways can be monitored as an indication of glial activation or as an indication of an increased brain inflammatory condition. The pathways can be summarized as follows. There are two IL1/TNF-activated kinase cascades, one of which involves the p38 homologues of MAP kinase and the other of which involves the p54 homologues of MAP kinase. IL1, TNF, TGF1beta, etc. activate both pathways. The activation of kinases or phosphatases of either or of both of these cascades can be assayed as an indicator of glial activation and/or the induction of a brain inflammatory reaction.

The activity of any of a variety of kinases can be assayed as indicators of glial activation or brain inflammatory reactions. Such kinases include, for example, GCK1 (Germinal center kinase), PAK kinase (for example, as identified in Manser, E., Leung, T., Salihuddin, H., Zhao, Z. S. and Lim, L. (1994) A brain serine/threonine protein kinase activated by Cdc42 and Rac1. *Nature* 367,40–46), MLK3 (mixed lineage kinase-3, also known as SPRK or PTK1), MLK1, MLK2, MLK4, DLK (also known as Muk), SEK1, SEK2, SAPK (stress activates protein kinases alpha/beta/gamma), MKK3, MKK6, p38 MAPK (alpha/beta/gamma/delta), MAPKAPK2, elk1, c-jun, ATF-2 and hsp27 (heat shock protein –25, also known as hsp25 and hsp28). Increased activity of the end targets of such cascades, for example, an increased activity of transcription factors CHOP/GADD 153 and MEF2C, can also be monitored as an indication of an induced inflammatory state of the brain cells. Conversely, decreased phosphorylation, or a decreased activity, is indicative of a lesser inflamed, or non-inflamed state of the brain cells. In a preferred embodiment, the activation or inactivation of cyclin dependent protein kinase 5 (cdk5) and mitogen activated protein kinase (MAPK) are assayed as an indication of an inflammatory or non-inflammatory state of the brain cells.

Thus, using the instant invention, agents that enhance or retard the formation of one or more of the characteristics of neurodegenerative disorders can be identified, including: neurofibrillary tangles, tau proteolytic fragments (and especially the formation of the 15–35 kDa forms of tau), or agents that enhance or retard the formation of tau hyperphosphorylation, and increased production and/or release of brain-produced cytokines especially TGF-beta, IL1-beta, TNF-alpha and LPS, an increased microglia reaction and/or activation, increased indications of brain inflammatory reactions, and changes, especially, increases in the levels and activities of protein kinases, for example, cyclin dependent protein kinase 5 (cdk5) and mitogen activated protein kinase (MAPK).

The above characteristics are also often seen in "brain aging" and are also useful as models thereof. Age-related neurodegenerative diseases and neurodegenerative diseases are characterized by many of the same properties including, e.g., an increased amount of neurofibrillary tangles and/or lysosomes, the appearance of basophilic granules in the mossy fiber terminal zone, the presence of secondary lysosomes with lipofuscin, amyloid deposition, amyloid plaques, neuritic plaques, synaptic loss, neuritic degeneration, neuronal death, increased glial elements (astrocytes, microglia), the fragmentation of the amyloid precursor protein, increased levels of Cathepsin D, inflammation, etc. Brain aging refers to a condition in which brain cells mimic the biochemistry or physiology of brain cells taken from a mature or elderly animal, especially human. Brain aging is manifested by significant changes in lysosomal functions and chemistry, e.g., the proliferation of secondary lysosomes filled with lipofuscin, decreases in cathepsin L activities and increases in the levels of cathepsin D. Additional characteristic features of human brain aging, as is found in neurodegenerative diseases, and especially Alzheimer's disease, include depletion of synaptic proteins, meganeurite formation, induction of early-stage tangles, and accompanying tau proteolysis.

II. Sources of Brain Cells

Any suitable source of brain cells can be used in embodiments of the invention. Typically, brain cells are derived from a mammal, such as a mouse, rat, guinea pig, rabbit, etc. Primary cell cultures, including human primary cell cultures, can also be used in the methods of the invention. Brain cells can be derived from a normal animal (e.g., comprising a wild-type apoE gene in the chromosome) or other suitable animals. For example, apoE-deficient brain cells or apoE4-containing brain cells can be used in embodiments of the invention. A preferred embodiment includes in vivo brain cells.

Among many types of brain cells suitable for embodiments of the invention, brain cells cultured from apoE-deficient brain cells or from apoE4-containing brain cells are especially preferred because they produce neurofibrillary tangles at significantly enhanced levels when compared to brain cells from control (normal) brains. The relatively high density with which such tangles form in apoE-deficient brain cells, or in apoE4-containing brain cells was not achievable by treatment with only a cathepsin D-increasing compound in normal brain cells even with a prolonged treatment with the same cathepsin D-increasing compound. However, a high density in normal brain cells was achievable by treating the cells under conditions in which cholesterol synthesis was inhibited or cholesterol levels were lowered.

The cultured brain cells, in particular apoE-deficient brain cells, even without the treatment with a cathepsin D-increasing compound, have some residual amount of neurofibrillary tangles. However, the initial density of neurofibrillary tangles in these untreated brain cells is too low to be regarded as an adequate model for neurodegenerative diseases, such as Alzheimer's disease.

If brain cells with a higher density of neurofibrillary tangles are desired, apoE-deficient brain cells or apoE4-containing brain cells can be preferably used in embodiments of the invention. Alternatively, such brain cells, and even normal brain cells, can be exposed to the cholesterol limiting embodiments of the invention as described below.

Preferably, when apoE-deficient brain cells are used, they are derived from a transgenic animal. For example, apoE-deficient brain cells useful in the method of the invention can be derived from a transgenic animal that carries an altered or ablated and/or expresses an altered endogenous apolipoprotein E gene (one or both alleles) that results in undetectable or significantly less amounts of apolipoprotein E proteins. These transgenic animals are sometimes referred to as apoE "knockout" animals. "Knock-out" transgenics can be transgenic animals having a heterozygous knock-out of the apoE gene or a homozygous knock-out of the apoE gene. For example, for use in the methods of the invention, the function and/or expression of the apoE protein in the apoE "knockout" animal is typically less than about 30%, preferably less than about 10%, more preferably less than about 5%, still more preferably less than about 1%, compared to a normal animal with the wild-type apoE genes. Most preferably, apoE-deficient brain cells are derived from apoE-knockout animals that have no apoE (i.e., null) gene expression.

Typically, apoE4-containing brain cells can be derived from a transgenic animal that comprises an exogenous apoE gene, e.g., a human apoE4 gene, polymorphic variants, interspecies homologs, or other conservatively modified variants thereof. Preferably, in these transgenic animals that comprise an exogenous apoE4 gene, their endogenous apoE gene is completely or partly knocked out.

Transgenic animals comprising apoE-deficient brain cells can be produced by recombinant methods known in the art. For example, the endogenous apoE gene function can be altered or ablated by, e.g., the deletion of all or part of the coding sequence, or insertion of a sequence, or substitution of a stop codon. In another example, the non-coding sequence of the apoE gene in the chromosome can be modified by, e.g., deleting the promoter region, the 3' regulatory sequences, enhancers and/or other regulatory sequences of the apoE gene in the chromosome. In yet another example, apoE-deficient transgenic animals can be produced by introducing an anti-sense construct that blocks the expression of the endogenous apoE gene products. In some cases, it may be desirable to produce conditional "knock-out" transgenic animals, wherein the alteration in the apoE gene can be induced by, e.g., exposure of the animal to a substance that promotes the apoE gene alteration postnatally. Preferably, both alleles of the apoE gene in the chromosome are altered in these transgenic animals.

The methods for producing transgenic animals are well known and described in, e.g., U.S. Pat. Nos. 5,464,764, and 5,627,059, the disclosures of which are incorporated herein by reference. In particular, the following references describe methods for producing apoE-deficient homozygous rodents: Plump et al., *Cell* 71:343–353 (1992); and Gordon et al., *Neuroscience Letters* 199:1–4 (1995), the disclosures of which are incorporated herein by reference. Moreover, some apoE-deficient transgenic animals are commercially available. For example, apoE-deficient homozygous mice, such as strain, are available from the Jackson laboratory, Bar Harbor, Me.

Moreover, apoE4-containing brain cells can be derived from a transgenic animal that comprises an exogenous apoE gene. For example, an exogenous apoE gene can be a human apoE4 gene, its interspecies homologs, polymorphic variants, or conservatively modified variants thereof. In human, three isoforms (apoE2, apoE3 and apoE4) express variants of apoE. Among these isoforms, apoE4 is known in the art to encode an apoE protein that is deficient in various functions. For example, compared to apoE3 that stimulates neurite extension, apoE4 was shown to inhibit neurite extension. Nathan et al., *Sco. Neurosci.* 20(Part 2):1033 (1994). It has also been suggested that, in vitro, tau interacts with apoE3, but not with apoE4. Stritmatter et al., *Exp. Neurol.* 125:163–171 (1994). Moreover, the human apoE4 isoform has been described as a risk factor of Alzheimer's disease (see, e.g., Peterson et al., *JAMA* 273:1274–1278 (1995)). Since brain cells comprising an apoE4 gene appear to lack many normal functions that other apoE isoforms possess, like the apoE-deficient brain cells, transgenic animals that comprise an apoE4 gene or its variants may also be used as a source of brain cells in embodiments of the invention.

Such transgenic animals can be produced using various apoE nucleotide sequences known in the art or conservatively modified variants thereof. For example, the human apoE4 gene has the Genbank accession number M10065. The mouse apoE gene has the Genbank accession number D00466. Other homologs or polymorphic variants of apoE genes can also be readily identified. For example, homologs or polymorphic variants of a known apoE gene can be isolated using nucleic acid probes by screening libraries under stringent hybridization conditions. Exemplary stringent hybridization conditions are as follows: a hybridization in a buffer containing 50% formamide, 5×SSC, and 1% SDS, at 42° C., or 5×SSC, 1% SDS, at 65° C., with wash in 0.2×SSC, and 0.1% SDS at 65° C. In some cases, moderately stringent conditions may be used to clone homologs or polymorphic variants of a known apoE gene. An example of a moderately stringent condition includes a hybridization in a buffer of 40% formamide, 1 M NaCl, 1% SDS at 37° C., and a wash in 1×SSC at 45° C. The source of homologs can be any species, e.g., rodents, primates, bovines, canines, human, etc.

Preferably, the exogenous apoE gene is operably linked with a mammalian apoE promoter, such as human apoE4 regulatory sequences. This construct can be introduced into an animal using methods known in the art. In these transgenic animals comprising an exogenous apoE gene (e.g., human apoE4 gene), preferably the endogenous apoE gene is partially or completely knocked out so that the endogenous apoE expression or function is insubstantial. Moreover, methods for producing transgenic animals comprising various human apoE isoforms are described in, e.g., U.S. Pat. Nos. 6,046,381 and 5,767,337, the disclosure of which are herein incorporated by reference.

Preferably, apoE4-containing brain cells are also derived from transgenic animals that are genetically modified. As above, for use in the methods of the invention, the function and/or expression of the apoE4 protein in the apoE4 animal is typically less than about 30%, preferably less than about 10%, more preferably less than about 5%, still more preferably less than about 1%, compared to a normal animal with the wild-type apoE genes.

In some embodiments, it may be desirable to use modified or mutated versions of apoE genes. For example, a modified version of a human apoE4 gene, when introduced into a transgenic animal, may be capable of producing a higher density of neurofibrillary tangles compared to the unmodified human apoE4 gene. Techniques for in vitro mutagenesis of cloned genes are well-known in the art and can be readily applied for making a modified or mutated apoE gene. See, e.g., Sambrook et al., *Molecular Cloning: A Laboratory Manual*, CSH Press (1989). The functional effect of a modified or mutated apoE gene can be further tested in vivo or in vitro. For example, a transgenic animal comprising a modified or mutated apoE gene can be produced using the methods known in the art. The change in the properties in apoE brain cells (e.g., the neurofibrillary tangle or phosphorylated tau fragment production) can be determined using the methods described below.

III Brain Cell Preparations

Brain cells and preparations containing the same can be prepared and processed in any suitable manner. For example, the brain can be processed in the form of tissue sections, such as brain slices. Alternatively, the brain tissues can be processed in the form of dissociated cells. Whether in the form of brain slices, dissociated cells, or other forms, they will be generically referred to as "brain cells" herein, unless otherwise indicated.

In one embodiment, an in vivo model is used. Such in vivo models have an advantage in that they retain the native brain architecture and environment. The effects that are brought about by the methods of the invention are presented against the background of a physiological environment that is more likely to mimic such conditions in humans. In vivo models are also more amenable to long term analysis than are primary cultures, or brain slice cultures. Another advantage is that multiple samples can be taken at the same time from the same animal and from different parts of the brain.

Preferably, the brain is processed in the form of brain slices so that neuronal circuitry or other biological functions are maintained, but environmental (culture) conditions can be closely monitored and normalized. A suitable thickness of the brain slice is readily determinable by those of skill in the art, and may be varied depending on the culture condition or subsequent analysis methods. For example, the brain can be sliced in the thickness of about 200 μm to about 800 μm, preferably about 350 μm to about 400 μm. The entire brain or portions of the brain can be processed into slices. For example, suitable brain slices may include a hippocampal slice, an entorhinal cortex slice, an entorhinohippocampal slice, a neocortex slice, a hypothalamic slice, or a cortex slice. Since neurofibrillary tangles tend to develop more prominently in the hippocampal region, a hippocampal slice is preferably used.

Alternatively, the brain can be processed into dissociated brain cells. The entire brain or selected regions of the brain (e.g., the hippocampal region) can be dissociated and maintained in a culture. Generally, the brain tissue is dissected, minced and digested in an enzyme (e.g., trypsin) for a suitable period of time. Then cells are centrifuged and plated at a low density in culture plates, and cultured. The methods for dissociating cells are well-known in the art. See, e.g., *Freshney, Culture of Animal Cells a Manual of Basic Technique*, 3rd ed., Wiley-Liss, New York (1994), incorporated herein by reference.

Brain cells in the form of slices or dissociated cells can be maintained in a culture. Suitable culture conditions for brain cells are well-known in the art. For example, brain cells can be placed onto culture plates, preferably on a support, such as a matrix or membrane, which allows cells to attach. Any suitable medium can be used in maintaining the culture of brain cells. Typically, the culture of brain cells is maintained in a medium that has all the essential nutrients. The culture medium generally has a neutral pH, e.g., between about pH 7.2 to about 7.8, and is maintained at a temperature between about 4° C. to about 40° C., typically at about 37° C. The culture of brain cells is typically maintained in an atmosphere that contains $CO_2$, preferably at 5% $CO_2$. In general, the culture can be maintained for at least about 60 days with a periodic replacement of culture medium.

IV. Assays for Neurofibrillary Tangles, Phosphorylated Tau and Tau Fragments

Determination of the neurofibrillary tangles, phosphorylated tau and/or tau fragments production can be qualitative or quantitative. In some applications, it may be sufficient to visually inspect the production of neurofibrillary tangles, phosphorylated tau and/or tau fragments. For example, it may be useful to visually observe the timing and the pattern of neurofibrillary tangle development at different regions of the brain. In other applications, it may be desirable to quantitate the neurofibrillary tangles, phosphorylated tau and/or tau fragments production. Quantitation would be particularly useful in a screening assay for agents that modulate the production of neurofibrillary tangles, phosphorylated tau and/or tau fragments.

Any suitable methods known in the art can be used to determine the production of neurofibrillary tangles, phosphorylated tau and/or tau fragments. For example, brain cells, in the form of brain slices, brain sections, dissociated cells, or other suitable forms, can be stained using conventional staining methods. For example, the brain cells can be fixed and stained with a silver stain (Bielschowsky) stain or toluidine blue. Then the stained neurofibrillary tangles can be visualized by microscopy.

To assess the appearance and density of tangles, light microscopic evaluation of tangles and tangle formation can be performed by scanning at 40×objective magnification. Immunoreactive elements can be plotted and images digitized and stored for any desired area. Especially, the following areas are preferentially examined: (1) the entorhinal cortical layers II/III; (2) CA1 str. pyramidale; (3) CA1 str. oriens; (4) subiculum str. oriens. Typically, five to seven serial sections are collected per brain slice. The bottom section (i.e., that on the Millipore filter side of the explant in the examples below) is generally neuron-poor and therefore not evaluated. Analysis preferably focuses on the dense paired helical filament (PHF) tau-immunoreactive elements that are greater than or equal to 2 μm in diameter. Comparisons from aligned serial sections can be used to identify structures that are present in more than one section so that individual elements are not double-counted. With this correction, the densely stained structures can be quantified and the result expressed per unit area for each field of analysis. In addition, the types of paired helical filament tau-positive structures can be catalogued as shown in FIG. 8. Differences in treatment regimens that affect the qualities as well as the number of tangles can thus be determined.

An absolute value of the density of tangles in the models of the invention is not required. Rather, a relative increase in the density of tangles, as compared to the density found in similar preparations but from wild-type or in controls, is indicative of the appearance of neurodegenerative disease changes in the cells of the method of the invention. In a preferred embodiment, the number of tangles per unit of space is 20–30% higher in the cells of the invention that have been exposed to a cathepsin D-increasing compound and/or a compound that decreases an effective concentration of cholesterol than it is in normal or control cells. In a preferred embodiment, such density is greater than 30% and may be even 100% or more higher than the wild-type or control cells (as such wild-type or control cells may lack tangles completely).

Morphologically, cells that contain an increased cathepsin D generally have lysosomes that are round in shape and that are distributed homogenously in the cell body. Changes in the shape, size and numbers of lysosomes and changes in the localization of enzyme activity from lysosomal localization to cytoplasmic localization can also be used as indexes by which to assess the degree of neurodegenerative disease characteristics that have been induced in the cells according to the invention.

In another example, the brain cells can be stained by immunostaining, and the neurofibrillary tangles, phosphorylated tau and/or tau fragments production can be visualized. In immunostaining, suitable capture reagents, such as antibodies that specifically bind to neurofibrillary tangles, phosphorylated tau and/or tau fragments, can be used. Preferably, antibodies preferentially bind to neurofibrillary tangles, phosphorylated tau and/or tau fragments and do not significantly cross-react with other proteins in the brain cells. For example, the antibodies that specifically bind to phosphorylated tau proteins and/or tau protein fragments have less than 50%, preferably less than 30%, more preferably less than 10% crossreactivity with native tau proteins that are not phosphorylated.

Examples of mouse monoclonal antibodies that preferentially bind phosphorylated tau and/or tau protein fragments over the tau found in normal adult brain include antibodies 8D8, RT97, 121.5, BF10 (Miller et al., *EMBO J.* 5:269–276 (1986)); AT8 (Bierat et al., *EMBO J.* 11:1593–1597 (1992)); SMI31, SMI34, SMI310 (Sternberger et al., *Proc. Natl. Acad. Sci. USA* 82:4274–4276 (1985); Sternberger & Sternberger, *Proc. Natl. Acad. Sci. USA* 80:6129–6130 (1983)); and ALZ-50 (Wolozin et al., *Science* 232:648–650 (1986)). Preferably, AT8 is used in embodiments of the invention to bind phosphorylated tau protein and/or tau protein fragments.

In immunostaining, an antibody against neurofibrillary tangles, phosphorylated tau and/or tau fragments is added to brain cells, and the brain cells are incubated for a sufficient time to allow binding between the antibody and neurofibrillary tangles, phosphorylated tau and/or tau fragments. The antibody may be labeled with a variety of labels that are detectable. Useful labels include magnetic beads (e.g., DYNABEADS), fluorescent dyes (e.g., fluorescein isothiocyanate, Texas red, rhodamine, and the like), radiolabels (e.g., $^{3}$H, $^{125}$I, $^{35}$S, $^{14}$C, or $^{32}$P), enzymes (e.g., horse radish peroxidase, alkaline phosphatase), and colorimetric labels such as colloidal gold or colored glass or plastic beads (e.g., polystyrene, polypropylene, latex, etc.). Alternatively, the antibody may be unlabeled, and a label may be coupled indirectly. For example, an unlabeled primary antibody can be added to the culture to bind neurofibrillary tangles, phosphorylated tau and/or tau fragments, and then a labeled secondary antibody can be used to amplify the signal for detection.

Means of detecting labels are well known to those of skill in the art. For example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Simple colorimetric labels may be detected simply by observing the color associated with the label.

Alternatively, the production of neurofibrillary tangles, phosphorylated tau and/or tau fragments can be determined using cell lysate in an immunoassay. An immunoassay can be performed in any of several formats. These formats include, for example, an enzyme immune assay (EIA) such as enzyme-linked immunosorbent assay (ELISA), a radioimmune assay (RIA), a Western blot assay, or a slot blot assay. For a review of the general immunoassays, see, e.g., *Methods in Cell Biology: Antibodies in Cell Biology*, volume 37 (Asai, ed. 1993); *Basic and Clinical Immunology* (Stites & Terr, eds., 7th ed. 1991). A general overview of applicable technology can also be found in *Harlow & Lane, Antibodies: A Laboratory Manual* (1988). See, also, U.S. Pat. Nos. 4,366,241; 4,376,110; 4,517,288; and 4,837,168.

In one embodiment, immunoblotting can be used to quantify the amount of neurofibrillary tangles, phosphorylated tau and/or tau fragments produced in brain cells treated with or without a cathepsin D-increasing compound and/or brain cells treated with or without (i.e., in the presence or absence of) a cysteine protease inhibitor. Generally, brain cells are disrupted in an electrophoresis sample buffer and are treated to obtain a fraction that contains proteins. The proteins are separated by gel electrophoresis and transferred to a membrane that binds the proteins nonspecifically. The location of neurofibrillary tangles, phosphorylated tau and/or tau fragments on the membrane is determined using, e.g., a labeled primary antibody or an unlabeled primary antibody, followed by a labeled secondary antibody. A detectable label may be, e.g., a radio-label or a fluorescent label or, an enzyme label. Then the membrane comprising a detectable label can be scanned, and digitized images can be quantitatively analyzed by densitometry.

In another embodiment, a sandwich assay can be performed by preparing a brain cell lysate sample, and placing the sample in contact with a solid support on which is immobilized a plurality of antibodies that bind neurofibrillary tangles, phosphorylated tau and/or tau fragments. The solid support is then contacted with detection reagents for neurofibrillary tangles, phosphorylated tau and/or tau fragments. After incubation of the detection reagents for a sufficient time to bind a substantial portion of the immobilized neurofibrillary tangles, phosphorylated tau and/or tau fragments, any unbound labeled reagents are removed. The detectable label associated with the detection reagents is then detected. For example, in the case of an enzyme used as a detectable label, a substrate for the enzyme that turns a visible color upon action of the enzyme is placed in contact with the bound detection reagent. A visible color will then be observed in proportion to the amount of the neurofibrillary tangles, phosphorylated tau and/or tau fragments in the sample.

According to the invention, the production of tau proteolytic fragments of a size from 15–35 kDa is increased. The size of tau proteolytic fragments can be determined using techniques known in the art, for example, gel electrophoresis, and especially SDS gel electrophoresis, or 2D gel electrophoresis.

The above described detection methods are merely exemplary, and other suitable detection methods will be apparent and can be readily substituted by one of skill in the art.

V. Treatment of Brain Cells with Cathepsin D-Increasing Compounds to Induce or Enhance the Characteristics of Neurodegenerative Diseases In a preferred embodiment, brain cells (e.g., normal brain cells, apoE-deficient brain cells, or apoE4-containing brain cells) are cultured in a medium that provides an effective concentration of cathepsin D as a result of an agent or compound that selectively increases the concentration or amount of cathepsin D in the brain cells. An effective concentration of cathepsin D can be induced, or increased, in a brain cell by either increasing the amount or concentration of cathepsin D or by stimulating the catalytic activity of cathepsin D. The "effective concentration" of cathepsin D is the concentration that will achieve the indicated result.

According to the invention, increasing the concentration of cathepsin D in the brain cells to an effective level results in the increased production of neurofibrillary tangles, the major component of which are abnormally phosphorylated tau proteins and tau protein fragments. Tau protein fragments are generally also hyperphosphorylated and are composed mainly of fragments containing the microtubule binding domains and flanks, and are generally of 27–35 kDa in size. In a preferred embodiment, the proteolysis of tau to fragments of a size of 15–35 kDa is examined. The inventors have discovered a phosphorylated tau fragment of 33 kDa that is thought to become a component of the tangles. Therefore, in an especially preferred embodiment, the amount or levels of the 33 kDa tau fragment are detected.

Preferably, such increase in the concentration of cathepsin D activity or levels is brought about or induced by contacting the brain cells with a cathepsin D-increasing compound throughout the entire period of culture during which it is desired to maintain such selectively increased concentrations or amounts of cathepsin D. Alternatively, the brain cells can be exposed in intermittent fashion of desired intervals, or, alternatively, only once at a desired point in the culture period.

A selective inhibitor of cathepsin B and L (i.e., ZPAD) can be used to selectively increase cathepsin D activity or levels relative to such activity or levels of cathepsin B and L. By changing the ratio of cathepsin B and/or L to cathepsin D, the cathepsin D concentration is increased to a concentration effective to induce the appearance or increase in the desired indicia of neurodegenerative disease. Selective inhibitors of cathepsin B and L have been reported to induce abnormally phosphorylated tau fragments in cultured hippocampal slices of normal rodents. Abnormally phosphorylated tau fragments assemble into structures having the appearance, size and epitopes of early-stage neurofibrillary tangles in human brain. See Bi et al., *Exp. Neurol.* 158:312–317 (1999). However, the density of neurofibrillary tangles produced in the normal rodent hippocampal slices was very sparse compared to the density of neurofibrillary tangles seen in the brain of Alzheimer's patients.

Surprisingly, when apoE-deficient or apoE4-containing brain cells are treated with a cathepsin D-increasing compound, levels of neurofibrillary tangles and phosphorylated tau proteins and fragments were elevated and greatly induced. In particular, when apoE-deficient brain cells were used, a dramatically increased production of neurofibrillary tangles, phosphorylated tau protein, and phosphorylated tau fragments was observed. Typically, the amount of neurofibrillary tangles or phosphorylated tau fragments seen in these treated apoE-deficient brain cells is at least twice, sometimes at least ten times greater than the amount of these materials seen in normal brain cells treated with the same compound. Also, the amount of neurofibrillary tangles or phosphorylated tau fragments seen in these treated apoE-deficient brain cells is at least ten times greater than the amount of these materials seen in apoE-deficient brain cells that are not treated with the compound. The density of neurofibrillary tangles in these apoE-deficient brain cells treated with a cathepsin D-increasing compound is sufficiently high that it mimics the density of neurofibrillary tangles typically found in the brain of Alzheimer's disease patients. Since apoE4-containing brain cells lack many normal function of apoE, like the apoE-deficient brain cells, apoE4-containing brain cells can also be used in embodiments of the invention.

Preferably, a cathepsin D-increasing compound increases the effective concentration of cathepsin D in brain cells by at least about 30%, preferably at least about 50%, more preferably at least about 80%, most preferably at least about 100%, compared to a control (e.g., brain cells untreated with the compound). As described previously, cathepsin D exists in three forms in the brain-the inactive proenzyme, the active single chain and the active heavy chain. Any compound that increases one or more of these cathepsin D forms can be used in embodiments of the invention.

Any suitable cathepsin D-increasing compound can be used in embodiments of the invention. Some of these compounds include inhibitors of cathepsin B and/or cathepsin L. Examples of these inhibitors include chloroquine, N-CBZ-L-phenylalanyl-L-alanine-diazomethylketone, N-CBZ-L-phenylalanyl-L-phenylalanine-diazomethylketone, beta-amyloid (amyloid beta protein), and mimetics thereof.

Other suitable cathepsin D-increasing compounds, and/or agents which mimic the activity of Cathepsin D (e.g., an inhibitor of cathepsin B and/or L or a modulator or an agonist of cathepsin D) are readily determinable by those skilled in the art. For example, a test compound can be contacted with brain cells. Then the activity or the amount of cathepsin D in brain cells can be measured using, e.g., an immunoassay using antibodies against cathepsin D. For example, antibodies such as Cathepsin D (Ab-2), Calbiochem can be used.

The activity or the amount of cathepsin D is then compared with a control amount (e.g., the amount of cathepsin D in brain cells that are not treated with the test compound). A test compound is referred to as a "cathepsin D-increasing compound" if it increases the activity or the amount of any one or more of cathepsin D forms (i.e., the inactive proenzyme, the active single chain or the active heavy chain) by, e.g., at least about 30%, preferably at least about 50%, more preferably at least about 80%, most preferably at least about 100%, compared to a control.

Brain cells can be contacted with a cathepsin D-increasing compound at any suitable time. For example, brain cells can be contacted with a cathepsin D-increasing compound when the culture is first established, or at a later time after maintaining the culture for a few days. Preferably, brain cells are contacted with a cathepsin D-increasing compound for a period of 1–18 days, preferably for a period of 4–8 days. To induce neurofibrillary tangles and phosphorylated tau fragments, a cathepsin D-increasing compound is typically added at a concentration of 0.1 $\mu$M to about 500 $\mu$M, more typically at a concentration of about 1 nM to about 100 $\mu$M.

Other modulatory compounds, in addition to a cathepsin D-increasing compound(s), can be, for example, added in the culture medium, or at least placed in contact with the brain cells or tissue containing such cells, to further facilitate the production of neurofibrillary tangles or other neurodegenerative characteristics or features in brain cells. Examples of modulatory compounds include oxidative free radicals ($Fe^{3+}$, $H_2O_2$, etc.), or inflammatory factors (TGFb, IL-1b, TNFalpha, LPS, etc.).

Typically, brain cells in a culture are treated with a cathepsin D-increasing compound under a condition such that the amount of neurofibrillary tangles, phosphorylated tau and/or tau fragments is increased by at least about 10%, or at least about 20%, or at least about 30%, or at least about 40%, or at least about 50%, or at least about 80%, or at least about 100%, or at least about 150%, or at least about 200%, compared to a control (e.g., brain cells that are cultured in substantially the same condition but without the cathepsin D-increasing compound). Also, brain cells that are treated with a cathepsin D-increasing compound generally produce neurofibrillary tangles, phosphorylated tau and/or tau fragments at a significantly higher level, typically at least two times, sometimes ten times, more than normal brain cells treated with the same compound. Preferably, the treatment conditions (e.g., concentration of a cathepsin D-increasing compound, a period of incubation, etc.) are selected so that the density of neurofibrillary tangles, phosphorylated tau and/or tau fragments produced in apoE-deficient brain cells or in apoE4-containing brain cells is similar to the density of these materials in aging brain or the brain of patients with Alzheimer's disease or other neurodegenerative diseases.

Brain cells produced in accordance with the present invention, under conditions in which cathepsin D levels or activity is increased, have a variety of applications. For example, the brain cells can be used as an in vitro assay system to screen libraries or identify agents that modulate the production of neurofibrillary tangles, phosphorylated tau and/or tau fragments in the brain, especially agents that decrease or prevent the accumulation of such characteristics. These agents can be further tested in other systems and/or in vivo to confirm their efficacy in modulating the production of neurofibrillary tangles in brain cells and possibly other conditions and/or pathologies associated with neurodegenerative diseases, such as the cognitive decline seen in persons afflicted with such disorders. In another example, the brain cells can be used to study the morphological pattern of neurofibrillary tangle formation in the brain. In another example, the brain cells can be used to study the effect of neurofibrillary tangle formation in normal aging. Such morphological studies would provide additional information regarding the pathological process of neurodegenerative diseases.

VI. Treatment of Brain Cells with a Cholesterol Decreasing Compound to Induce or Enhance the Characteristics of Neurodegenerative Diseases According to another embodiment of the invention, decreasing intracellular cholesterol levels in brain cells, for example, by inhibiting cholesterol synthesis, can be used to induce the characteristics of neurodegenerative diseases, and especially Alzheimer's disease, in that brain cell—even in cells from normal animals. In a preferred embodiment, the brain cell in which cholesterol is decreased is a neuron and the characteristics that are monitored are the formation of tangles and tau fragmentation. In another embodiment, the brain cells in which cholesterol is decreased are glia cells and the characteristics that are monitored are glia activations, glia reactions, and/or cytokine production and/or release.

Exposing the brain cell to such cholesterol-lowering agents or conditions mimics results found when using apoE-deficient brain cells, or brain cells that contain the apoE4 isotype. The advantage of the cholesterol-limiting treatment (i.e., inhibition of cholesterol synthesis and/or lowering of cholesterol levels) is that relatively high tangle densities can be obtained in normal cells by such treatment, densities that are otherwise only obtainable in cells in apoE-deficient brain cells, or in apoE4-containing brain cells. Accordingly, for the first time, high densities of neurofibrillary tangles and the appearance of other characteristics of neurodegenerative diseases can be induced in brain cells from normal animals in a relatively short period of time, and thus be useful as a model for studying such diseases and for identifying agents useful to treat or prevent the same. A combined inhibition of cholesterol synthesis and lysosomal dysfunction can be used to further dramatically enhance the neurodegenerative effects brought about by either manipulation alone.

Therefore, in another embodiment, the characteristics of neurodegenerative diseases, such as, for example
(1) neurofibrillary tangles,
(2) the hyperphosphorylation of tau,
(3) the fragmentation of tau, that is, tau proteolysis and especially, increased amounts of the 15–35 kDa forms of tau,
(4) increased production and/or release of brain-produced pro-inflammatory cytokines especially TGF-beta, TGF-alpha, IL1, IL1-alpha, IL1-beta, IL6, IL10, TNF, TNF-alpha and LPS and most especially TGF-beta, IL-1beta and LPS,
(5) increased microglia reaction and/or activation,
(6) increased indications of brain inflammatory reactions
(7) increased conversion of p35 to p25
(8) changes in the levels and activities of protein kinases, for example, cyclin dependent protein kinase 5 (cdk5) and mitogen activated protein kinase (MAPK), are induced by exposing brain cells to a condition that, or by contacting brain cells with a compound that, inhibits cholesterol synthesis or otherwise decreases the levels of cholesterol.

According to this embodiment, to increase the production of such characteristics, and especially neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases, brain cells are contacted with a compound capable of decreasing levels of cholesterol or inhibiting cholesterol synthesis or otherwise capable of decreasing the concentration of cholesterol ("cholesterol-lowering compound"). This compound can preferably decrease either the concentration of cholesterol or the synthesis of cholesterol in cells and thus decrease the availability of cholesterol within the cells.

In one aspect, the invention provides cultured brain cells, and methods for producing the brain cells, wherein the brain cells have been treated with a compound that increases cathepsin D to an effective concentration and with a compound that decreases cholesterol levels or inhibits cholesterol synthesis to an sufficient low concentration to result in or to produce increased amounts of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases compared to such indicia in a control (e.g., brain cells that are untreated with said compound(s)).

Embodiments of the invention include methods comprising: (a) culturing brain cells; and (b) contacting the brain cells with a compound that increases an effective concentration of cathepsin D and with a compound that decreases an effective concentration of cholesterol, thereby producing properties of a brain afflicted with neurodegenerative disease, wherein the properties include increased neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases and/or related biochemical changes.

In some embodiments, a method for increasing neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in brain cells comprises: (a) culturing the brain cells in a medium which selectively increases an effective concentration of cathepsin D and that decreases the concentration of cholesterol in the medium and cells; and (b) optionally, determining the production of and/or levels of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases.

Preferably, a cholesterol-lowering compound decreases the effective concentration of cholesterol in brain cells by at least about 30%, preferably at least about 50%, more preferably at least about 80%, most preferably at least about 100%, compared to a control (e.g., brain cells untreated with the compound). Any compound that lowers cholesterol levels (for example, by inhibiting cholesterol synthesis or stimulating cholesterol degradation or lowering the availability of cholesterol) can be used in embodiments of the invention. Examples which can be used in embodiments of the invention include compounds which decrease either the concentration of cholesterol, or the synthesis of cholesterol, or decreases the availability of cholesterol in cells.

Any suitable cholesterol-lowering compound can be used in embodiments of the invention. Some of these compounds include inhibitors of hydroxymethylglutaryl coenzyme A (HMG-CoA Reductase) inhibitors. Examples of these inhibitors include members of the statin class of compounds, such as, for example, mevastatin, simvastatin, atorvastatin, pravastatin, fluvastatin, lovastatin, cerivastatin, and mimetics thereof.

A further class of compounds includes agents which decrease the availability of cholesterol within cells. Examples of this class include agents which bind, immobilize, and/or otherwise separate cholesterol from other elements found within cells.

Other suitable cholesterol-lowering compounds, and/or agents which modulate the activity of cholesterol are readily determinable by those skilled in the art. For example, a test compound can be contacted with cells. Then the activity the amount of cholesterol in cells can be measured using, e.g., an immunoassay using antibodies against cholesterol. Alternatively, a test compound can be contacted with cells and the activity or amount of HMG-CoA reductase (an enzyme involved in cholesterol synthesis in cells) and/or other entities involved in cholesterol synthesis, degradation, storage, and/or transport can be measured using assays known to one skilled in the art.

The activity or the amount of cholesterol and/or the activity or amount of HMG-CoA reductase and/or other entities involved in cholesterol synthesis, degradation, storage, and/or transport is then compared with a control amount (e.g., the amount of cholesterol and/or the activity or amount of HMG-CoA reductase and/or other entities involved in cholesterol synthesis, degradation, storage, and/or transport in cells that are not treated with the test compound). A test compound is referred to as a "cholesterol-lowering compound" if it decreases the activity or the amount of cholesterol and/or the activity or amount of HMG-CoA reductase and/or modulates other entities involved in cholesterol synthesis, degradation, storage, and/or transport by, e.g., at least about 30%, preferably at least about 50%, more preferably at least about 80%, most preferably at least about 100%, compared to a control.

Brain cells can be contacted with a cholesterol-lowering compound at any suitable time. For example, brain cells can be contacted with a cholesterol-lowering compound when the culture is first established, or at a later time after maintaining the culture for a few days. Preferably, brain cells are contacted with a cholesterol-lowering compound for a period of 1, 2, 3, 4, 5, 10, 20, 30, 40, 50, 60, 90, 120, 150, or 240 days, or preferably, for in vitro experiments, for a period of 4, 5, 6, 7, 8 or 9 days, while in vivo experiments preferably have a duration of 30–120 days, or any appropriate period of time to achieve the desired effect. To induce the formation of neurofibrillary tangles, and/or phosphorylated tau, and/or tau fragments, and/or microglial reactions, and/or cytokine reactions, or any other of the indicia of neurodegenerative brain disease discussed above. For in vitro experiments a cholesterol-lowering compound is typically added at a concentration of 0.1 $\mu$M to about 500 $\mu$M, more typically at a concentration of about 1 nM, 10 nM or 100 nM to about 100 $\mu$M, and especially 20 $\mu$M, or any appropriate amount that achieves the desired effect. For in vivo experiments a cholesterol-lowering compound is typically added at a dose of 0.5 to about 50 mgs/kg body weight of the animal, more typically about 5–40 mgs/kg, and especially 10–20 mgs/kg, or any appropriate amount that achieves the desired effect. More than one cholesterol-lowering compound can be administered at the same time, or sequentially at different times, to the brain cell preparation or animal.

Other modulatory compounds, in addition to such cholesterol-lowering compound(s), can be added in the culture medium to further facilitate the production of neurofibrillary tangles or any of the other neurodegenerative features in brain cells, especially tau fragmentation. Examples of useful modulatory compounds in this regard include agents capable of modulating those kinases and/or phosphatases that are involved in cholesterol metabolism or that interact with cholesterol to affect cell function, amyloid beta peptide, oxidative free radicals ($Fe^{3+}$, $H_2O_2$, etc.), or inflammatory factors (TGF-beta, IL-1b, TNFalpha, LPS, etc.).

Typically, brain cells in a culture are treated with a cholesterol-lowering compound under a condition such that the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases is increased by at least about 10%, or at least about 20%, or at least about 30%, or at least about 40%, or at least about 50%, or at least about 80%, or at least about 100%, or at least about 150%, or at least about 200%, compared to a control (e.g., brain cells that are cultured in substantially the same condition but without the cholesterol-lowering compound). Also, brain cells that are treated with a cholesterol-lowering compound generally produce neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases at a significantly higher level, typically at least two times, sometimes ten times more than normal brain cells treated with the same compound. Preferably, the treatment conditions (e.g., concentration of a cholesterol-lowering compound, the period of contact with the brain cells, etc.) are selected so that the density of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases produced is similar to the density of these materials and/or reactions in aging brain or the brain of patients with Alzheimer's disease or other neurodegenerative diseases.

VII. Treatment of Brain Cells with a Cysteine Protease Inhibitor to Prevent or Reverse the Characteristics of Neurodegenerative Diseases According to a further model of the invention, the above indicia of neurodegenerative disease can be prevented or reversed by exposing brain cells to a cysteine protease inhibitor, and preferable a calpain inhibitor. Specifically such protease inhibitor, and especially calpain inhibitor, reverses the effects of the lysosomal dysfunction and/or cholesterol-lowering, and decreases, or prevents the formation of:

(1) neurofibrillary tangles,
(2) the hyperphosphorylation of tau,
(3) the fragmentation of tau, that is, tau proteolysis and especially, increased amounts of the 15–35 kDa forms of tau,
(4) increased production and/or release of brain-produced pro-inflammatory cytokines especially TGF-beta, TGF-alpha, IL1, IL1-alpha, IL1-beta, IL6, IL10, TNF, TNF-alpha and LPS and most especially TGF-beta, IL-1beta and LPS,
(5) increased microglia reaction and/or activation,
(6) increased indications of brain inflammatory reactions
(7) increased conversion of p35 to p25
(8) changes in the levels and activities of protein kinases, for example, cyclin dependent protein kinase 5 (cdk5) and mitogen activated protein kinase (MAPK).

Cysteine protease inhibitors, and specifically calpain inhibitors, are therefore useful to identify agents or compounds that might modulate the effects of the cysteine protease inhibitor, for example, induce or enhance the effects, or interfere with the same.

The term "calpain inhibitor" refers to a compound that inhibits the proteolytic action of calpain-I or calpain-II, or both, but preferably calpain-I. The term calpain inhibitors as used herein include those compounds having calpain inhibitory activity in addition to or independent of their other biological activities. A wide variety of compounds have been demonstrated to have activity in inhibiting the proteolytic action of calpains. Examples of calpain inhibitors that are useful in the practice of the invention include N-acetyl-leucyl-leucylmethional (ALLM or calpain inhibitor II), N-acetyl-leucyl-leucyl-norleucinal (ALLN or calpain inhibitor 1), calpain inhibitor III (carbobenzoxy-valyl-phenylalanal; Z-Val-Phe-CHO), calpain inhibitor IV (Z-LLY-FMK; Z-LLY-CH$_2$F where Z=benzyloxycarbonyl), calpain inhibitor V (Mu-Val-HPh-FMK where Mu is morphlinoureidyl and Hph is homophenylalanyl), calpeptin (benzyloxycarbonyldipeptidyl aldehyde; Z-Leu-Nle-CHO), calpain inhibitor peptide (Sigma No. C9181), calpastatin, acetyl-calpastatin (acetyl calpain inhibitor fragment, 184–210), leupeptin, mimetics thereof and combinations there, AK275, MDL28170 and E64. Additional calpain inhibitors are described in the following U.S. patents, incorporated herein by reference, U.S. Pat. Nos. 5,716,980; 5,714,471; 5,693,617; 5,691,368; 5,679,680; 5,663,294; 5,661,150; 5,658,906; 5,654,146; 5,639,783; 5,635,178; 5,629,165; 5,622,981; 5,622,967; 5,621,101; 5,554,767; 5,550,108; 5,541,290; 5,506,243; 5,498,728; 5,498,616; 5,461,146; 5,444,042; 5,424,325; 5,422,359; 5,416,117; 5,395,958; 5,340,922; 5,336,783; 5,328,909; 5,135,916.

Preferably the concentration of such inhibitor in the fluid, culture medium, milieu, or other environment contacting the brain cells of the invention is a concentration of 1 nM to 1 mM, and preferably 10 nM, 100 nM, 1 $\mu$M, 10 $\mu$M, 100 $\mu$M and especially 20 $\mu$M, or any appropriate amount that achieves the desired effect.

The cysteine protease inhibitor, and especially, the calpain inhibitor, can be added at the beginning of the culture of the brain cells, or intermittently during the culture, as desired. The inhibitor can be one that is active metabolically intracellularly, or that acts by binding to the outer membrane and inducing a cascade that ultimately results in an inhibition and/or reversal of the desired characteristic of neurodegenerative disease that is being measured in the culture. Two or more inhibitors can be simultaneously added, or sequentially added.

Accordingly, a target class of compounds for a screening method can be identified according to the invention by a method comprising: (a) contacting brain cells with a cathepsin D-increasing compound that increases cathepsin D to an effective concentration in the brain cells, and/or contacting brain cells with a cholesterol-lowering compound wherein the increased concentration of cathepsin D and/or the decreased concentration of cholesterol is effective to increase the amount of neurofibrillary tangles, phosphorylated tau and/or tau fragments in the brain cells; (b) contacting the brain cells with a cysteine protease inhibitor; and (c) determining whether the cysteine protease inhibitor modulates the amount of neurofibrillary tangles, phosphorylated tau and/or tau fragments in the brain cells treated with the cysteine protease inhibitor compared to the brain cells that are not treated with the cysteine protease inhibitor.

The present invention thus provides a novel target—inhibition of tau proteolysis by a cysteine protease inhibitor, and especially by a calpain inhibitor—for intervention and treatment of Alzheimer's disease, neurodegenerative diseases, and related disorders, such as senile dementias, progressive supranuclear palsy, corticobasal degeneration, frontotemporal dementias, Parkinsonism, Pick's disease, etc., and for diminishing the occurrence of neurofibrillary tangles and/or tau fragmentation events capable of resulting in the formation of neurofibrillary tangles and/or tau-related pathologies.

That cysteine protease inhibition, and especially calpain inhibition can reverse the characteristics of neurodegenerative diseases, and especially tangle formation, is especially surprising because the art has taught that hyperphosphorylated tau in the paired helical filaments is resistant to degradation by calpain. As much as five times the levels of calpain are needed to completely degrade paired helical filament tau as compared to "normal" tau (Mercken, M. et al., FEBS Lett 38:10–14 (1995); Yang, L.-S. and Ksiezak-Reding, H., Eur. J. Biochem. 233:9–17 (1995))

In a preferred embodiment of this aspect of the invention, the present invention provides a cysteine protease inhibitor, and particularly an inhibitor of the class of cysteine proteases known as calpains, that affects the central nervous system in a manner that alleviates the symptomologies of Alzheimer's disease, senile dementia, and related disorders, such as Pick's disease. Further, the present invention provides the advantage of alleviating the symptomologies of Alzheimer's disease by inhibiting the formation of neurofibrillary tangles and related tau fragmentation events characteristic of such diseases, of which there is a need in the art.

In a preferred embodiment, the present invention provides novel methods for ameliorating certain conditions associated with neurodegenerative disease and/or neurodegenerative diseases, such as Alzheimer's disease, Pick's disease, senile dementia, etc. In accordance with embodiments of the invention, a host afflicted with a neurodegenerative disease, such as Alzheimer's disease, Pick's disease, etc., is treated with a cysteine protease inhibitor, e.g., by administering a pharmaceutically effective amount of an agent capable of inhibiting the activity of a member of the calpain class of proteases.

In another embodiment of the invention brain cells (e.g., normal brain cells, apoE-deficient brain cells, apoE4-containing brain cells, and/or other transgenically altered brain cells) are treated with a cysteine protease inhibitor, e.g., by contacting the brain cells with an agent capable of inhibiting the activity of a member of the calpain class of proteases. The administration of the agent to the host, and/or the contacting of the agent with the brain cells, then results in a decreased amount of tau fragmentation events which can lead to the formation of neurofibrillary tangles, and the decreased formation of neurofibrillary tangles, or the degradation of tangles that have already been formed.

While some features of neurodegenerative disease or neurodegenerative diseases have been partially remedied by other classes of therapeutics, a key feature such as the reduction of tau fragmentation and/or a reduction in the density of neurofibrillary tangles in the brain was missing in these treatment modalities. The present invention advantageously provides a therapeutic treatment for a host and/or a treatment for brain cells, wherein the host and/or the brain cells comprise, among other things, reduced levels of tau fragmentation and reduced levels of neurofibrillary tangles.

In the present invention, any suitable host or brain cells can be treated. Preferably, hosts are human, and are believed to be afflicted with a neurodegenerative disease, such as Alzheimer's disease, Pick's disease, or a related disorder such as senile dementia, etc. Preferably, brain cells are from a mammal, such as rat, mouse, guinea pig, rabbit, etc. In some embodiments, apoE-deficient brain cells or apoE4-containing brain cells, or other brain cells from a transgenic animal, can be treated.

In one aspect, the invention provides compounds, and methods for using such compounds to decrease the formation of neurofibrillary tangles and/or tau fragments compared to a control (e.g., a host not given said compound(s) and/or brain cells that are untreated with said compound(s)). Embodiments of the invention include methods comprising:

(a) identifying a host thought to be afflicted with a disorder or disease believed to comprise abnormal tau fragmentation events and/or increased levels of neurofibrillary tangles; and (b) administering to such host a compound that inhibits a member of the calpain class of cysteine proteases, wherein, as a result of the administration of the compound, the characteristics of neurodegenerative disease are lessened or decreased, and preferably, there are decreased levels of neurofibrillary tangles, and/or there are decreased levels of tau fragments and/or decreases in related tau-mediated pathologies.

In other embodiments, a method is provided for decreasing neurofibrillary tangles and/or tau fragmentation in brain cells, the method comprising contacting brain cells with a medium under conditions which, or in the presence of sufficient amounts of a compound that, inhibit one or more members of the calpain class of cysteine proteases, and preferably calpain I.

In another embodiment, the invention provides a target class of compounds for a screening method comprising:

(a) contacting brain cells with a cathepsin D-increasing compound and/or a cholesterol-decreasing compound that increases cathepsin D and/or decreases cholesterol in the brain cells to levels effective to increase the amount of neurofibrillary tangles, phosphorylated tau and/or tau fragments in the brain cells;

(b) contacting the brain cells with a cysteine protease inhibitor, and preferably an inhibitor of calpain; and (c) determining whether the cysteine protease inhibitor modulates the amount of neurofibrillary tangles, phosphorylated tau and/or tau fragments in the brain cells treated with the cysteine protease inhibitor compared to the brain cells that are not treated with the cysteine protease inhibitor.

VIII. Screening Assays

Screening assays can be performed in vitro or in vivo. To produce brain cells comprising neurofibrillary tangles, phosphorylated tau and/or tau fragments, etc., the methods described above can be used.

The advantage of using brain cells in the form of slices or in vivo animal testing for the screening assays is that since the neuronal circuitry and other biological functions are more intact in brain slices and in vivo, compared to dissociated brain cells, the experimental conditions better mimic the physiological condition of the brain.

Preferably, the concentration of cathepsin D, and/or the synthesis (and/or levels) of cholesterol, and other culture conditions are adjusted so that the density of neurofibrillary tangles, phosphorylated tau and/or tau fragments in the brain cells (prior to contacting with an agent) is similar to the density of these materials found in neurodegenerative diseases, such as Alzheimer's disease. ApoE-deficient brain cells or apoE4-containing brain cells can be used.

To screen agents that modulate the production of neurofibrillary tangles, phosphorylated tau and/or tau fragments, brain cells are contacted with a test agent. An "agent" refers to any molecule, including, e.g., a chemical compound (organic or inorganic), or a biological entity, such as a protein, sugar, nucleic acid or lipid, that modulates the amount of neurofibrillary tangles, phosphorylated tau and/or tau fragments in brain cells. Generally, a test agent is added to the culture medium in the range from 0.1 nM to 10 mM, and/or an animal is administered a dose of 0.5 to 50 mgs/kg.

Agents can be obtained from a wide variety of sources, including libraries of synthetic or natural compounds. For example, libraries of natural compounds in the form of bacterial, fungal, plant and animal extracts can be tested. Known pharmacological agents may be subjected to directed or random chemical modifications, e.g., alkylation, esterification, amidification, etc. to produce a library of structural analogs. Alternatively, a library of randomly or directed synthesized organic compounds or biomolecules (e.g., oligonucleotides and oligopeptides) can be used as a source of agents. Preparation and screening of combinatorial libraries are well known to those of skill in the art. See, e.g., U.S. Pat. No. 5,010,175, PCT Publication No. WO 93/20242, PCT Publication No. WO 92/00091, Chen et al., *J. Amer. Chem. Soc.* 116:2661 (1994), U.S. Pat. No. 5,539, 083.

Since the production of neurofibrillary tangles, phosphorylated tau and/or tau fragments is correlated with the increased concentration of cathepsin D in brain cells, an inhibitor of cathepsin D may be effective in reducing the production of neurofibrillary tangles or other neuropathological lesions. Accordingly, a library of putative cathepsin D inhibitors can be used as a source of agents in a screening assay. Methods for producing a library of potential cathepsin D inhibitors are known. For example, a combinatorial library of agents against the active site of cathepsin D was previously synthesized by others based on the crystal structure of cathepsin D. See Kick et al., *Chem. Biol.* 4:297–307 (1997). The library of these agents can be screened by methods in accordance with embodiments of the invention.

An agent can be contacted with brain cells at any suitable time. For example, an agent can be contacted with brain cells prior to contacting the brain cells with a cathepsin D-increasing compound, and/or a compound that lowers the cholesterol to an effective concentration in the cells. In another example, the brain cells can be contacted with the agent after the brain cells are contacted with a cathepsin D-increasing compound and/or a compound that lowers cholesterol to an effective concentration in the cells. Preferably, the brain cells can be contacted simultaneously with the agent and the cathepsin D-increasing compound and/or a compound that lowers cholesterol to an effective concentration in the cells. Generally, brain cells are contacted with an agent for a period of time sufficient to allow the agent to penetrate the cells and to take an effect. Typically, the brain cells and an agent are contacted for a period of between about 1 minute to about 30 days, preferably between about 30 minutes to about 6 days. Typically, during this time, the culture of brain cells is maintained at a temperature between about 4° C. to about 40° C., preferably at 37° C., at atmosphere containing about 0 to 10% $CO_2$. Other suitable experimental conditions are readily determinable by those skilled in the art.

A number of assays known in the art can be used to determine the effect of candidate agents on the production of neurofibrillary tangles, phosphorylated tau and/or tau fragments in brain cells. For example, various staining or immunoassays described above can be used, and the details of these assay techniques will not be repeated in this section. Other suitable assays will be readily determinable by those of skill in the art, and can be applied in detecting the production of neurofibrillary tangles, phosphorylated tau and/or tau fragments.

In determining whether an agent modulates the cathepsin D and/or cholesterol-induced production of neurofibrillary tangles, phosphorylated tau and/or tau fragments in brain cells, experiments are typically carried out with a control. A control can be, e.g., adding no agent or adding a different amount or type of agent and extrapolating and determining the zero amount. A statistically significant difference in a test amount (e.g., brain cells treated with a test agent) and a control amount (e.g., brain cells untreated with a test agent) of neurofibrillary tangles, phosphorylated tau and/or tau fragments indicates that the test agent modulates the production of neurofibrillary tangles of phosphorylated tau fragments. For example, inhibition of neurofibrillary tangles, phosphorylated tau and/or tau fragment production is achieved when the test amount of neurofibrillary tangles or phosphorylated tau or tau fragments relative to the control amount is about 90% (e.g., 10% less than the control), optionally 80% or less, 70% or less, 60% or less, 50% or less, 40% or less, or 25–0%.

Brain cells in accordance with embodiments of the invention provide a model for the development of the biochemical characteristics of neurodegenerative diseases, such as Alzheimer's disease. In regular rats, mevastatin produces similar types and amounts of pathologies as observed in ApoE-knockout mice, and mevastatin plus ZPAD in regular rats produces results similar to those found in apoE-knockout mice treated with ZPAD. However, just as useful are normal rats treated with an agent that can lower the concentration of cholesterol since neurofibrillary tangles and phosphorylated tau protein/tau fragments are induced at a higher density, mimicking early-stage tangles found in Alzheimer's disease and other neurodegenerative diseases.

ApoE-deficient brain cells and apoE4-containing brain cells provide a cost and time efficient in vitro model to study such diseases. For example, apoE-deficient brain cells or apoE4-containing brain cells produced in accordance with embodiments of the invention can be used to screen agents that may modulate the production of neurofibrillary tangles, phosphorylated tau and/or tau fragments in the brain cells. Efficacious agents that are identified by in vitro screening methods described herein can be further tested to determine their efficacy in vivo. Some of these agents can potentially be useful as therapeutic compounds for neurodegenerative diseases, including Alzheimer's disease.

In another aspect, the invention provides screening assays to identify cysteine protease inhibitors that modulate the amount of tau fragments. Additionally, such inhibitors may be assayed for their ability to inhibit the formation of tau fragments in the aforementioned assay system. For example, such screening methods would comprise:

(a) contacting brain cells with an agent capable of modulating the activity or levels of a cysteine protease;

(b) determining whether the agent modulates the amount of neurofibrillary tangles, tau fragmentation and/or the production of phosphorylated tau in the brain cells treated with the agent compared to the brain cells that are not treated with the agent.

Thus, the inhibition of tau proteolysis can be used as an assay for a new calpain inhibitor, especially a calpain inhibitor that has therapeutic utility in the treatment or prevention of neurological disorders, and, especially, Alzheimer's disease and/or Pick's disease.

In another aspect, the invention provides screening assays that identify MAP kinase inhibitors that modulate the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases. Additionally, such inhibitors may be assayed for their ability to inhibit the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in the aforementioned assay system. For example, such screening methods can include:

(A) contacting brain cells with an agent that modulates the activity or levels of a MAP kinase; and (B) determining whether the agent modulates the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in the brain cells treated with the agent as compared to the brain cells that are not treated with the agent, and (C) identifying those agents that decrease or that increase one or more of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases in the brain cells treated with the agent as compared to the brain cells that are not treated with the agent.

In a further embodiment, such agents are used in brain cells treated with such agent to increase or decrease, respectively, one or more of such neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases that such agent increased or decreased in the screening assay of the invention.

MAP kinase inhibitors that would be useful in this regard are known in the art. PD98059 (2-2(Amino-3-methoxyphenyl)-4H-1-benzopyran-4-one) is a specific inhibitor of mitogen-activated protein kinase kinase (MAPKK). SB209580 (4-[5-(4-Fluorophenyl)-2-[4-(methylsulphonyl)phenyl]-1H-imidzaol-4yl]pyridine) is a highly selective inhibitor of p38 mitogen-activated protein kinase (p38 MAPK) and also inhibits cycoloxygenase-1 and -2, and thromboxane synthase. PD98059 and SB203580 are especially useful at concentrations of 5–100 $\mu$M range. U0126 (1,4-Diamino-2,3-dicyano-1,4-bis[2-aminophenylthio]butadiene; Promega) is a selective inhibitor of MAP kinase kinase. U0126 is more potent and inhibits MEK-1 and MEK-2 with an $IC_{50}$ value of 0.07 and 0.06 $\mu$M, respectively. Preferred concentrations of U0126 are 5–20 $\mu$M.

The compounds can be employed in a free base form or in a salt form (e.g., as pharmaceutically acceptable salts). Examples of suitable pharmaceutically acceptable salts include inorganic acid addition salts such as hydrochloride, hydrobronide, sulfate, phosphate, and nitrate; organic acid addition salts such as acetate, galactarate, propionate, succinate, lactate, glycolate, malate, tartrate, citrate, maleate, fumarate, methanesulfonate, salicylate, p-toluenesulfonate, and ascorbate; salts with acidic amino acids such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N-dibenzylethylenediamine salt; and salts with basic amino acids such as the lysine salt and arginine salts. The salts may be in some cases be hydrates or ethanol solvates.

The manner in which the compounds are administered in vivo can vary. The compounds can be administered by inhalation (e.g., in the form of an aerosol either nasally or using delivery articles of the type set forth in U.S. Pat. No. 4,922,901 to Brooks et al., the disclosure of which is incorporated herein by reference in its entirety); topically (e.g., in lotion form); orally (e.g., in liquid form within a solvent such as an aqueous or non-aqueous liquid, or within a solid carrier); intravenously (e.g., within a dextrose or saline solution); as an infusion or injection (e.g., as a suspension or as an emulsion in a pharmaceutically acceptable liquid or mixture of liquids); intrathecally; intracerebroventricularly; or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Novartis and Alza Corporation. The administration of the pharmaceutical compositions of the present invention can be intermittent, or at a gradual, continuous, constant or controlled rate to a warm-blooded animal, (e.g., a mammal such as a mouse, rat, cat, rabbit, dog, pig, cow, monkey or human). In addition, the time of day and the number of times per day that the pharmaceutical formulation is administered can vary. Administration preferably is such that the active ingredients of the pharmaceutical formulation interact with receptor sites within the body of the subject that effect the functioning of the central nervous system. More specifically, in treating a neurodegenerative disease, administration preferably is such so as to optimize the effect upon those relevant protease and/or kinase subtypes (e.g., those which have an effect upon the functioning of the central nervous system), while minimizing the effects upon protease and/or kinase subtypes in muscle and ganglia. Other suitable methods for administering the compounds of the present invention are described in U.S. Pat. No. 5,604,231 to Smith et al., the disclosure of which is incorporated herein by reference in its entirety The following examples are offered by way of illustration, not by way of limitation.

EXAMPLES

Example 1

I. Materials and Methods a. Preparation of Mouse Hippocampal Slice Cultures

Hippocampal slices were prepared from 10 to 13 day old C57BL/6J (wild-type) and C57BL/6J-ApoE$^{m1Unc}$ (ApoE-knockout) mice obtained from the Jackson laboratory, Bar Harbor, Me. Pups were placed under light bromo-chloro-trifluoroethane anesthesia (Sigma, St. Louis, Mo.), and killed by decapitation. After removing the brains, the hippocampus was dissected and subsequently placed on a McIlwain tissue chopper where slices (400 $\mu$m thick) were obtained and placed in a solution of cutting medium consisting of Minimum Essential Medium (MEM) with Earle's salts (Gibco, Grand Island, N.Y.), 25 mM HEPES buffer, 10 mM Tris base, 10 mM glucose, and 3 mM $MgCl_2$, pH 7.20. Hippocampal slices were then placed onto the membranes of Millicell-CM culture inserts (Millipore Corp., Bedford, Mass.) in 6 well culture cluster plates and 1 ml of media per well using the methods described by Stoppini et al., *J. Neurosci. Methods* 37(2):173–82 (1991). The culture medium was described previously by Bednarski et al., *J. Neurosci.* 17(11):4006–21 (1997). The cultures were incubated in a 37° C. atmosphere containing 5% $CO_2$ and the culture medium was replaced every other day until the initiation of experiments. Each culture cluster plate contained hippocampal slices from either two wild-type or two apoE-knockout mice and individual wells were used for matched control and experimental treatment groups.

After maintaining the slices with normal culture medium (Bednarski et al., *J. Neurosci.* 17(11):4006–21 (1997)) in vitro for 12–14 days, slices were incubated with culture medium containing either 20 $\mu$M N-CBZ-L-phenylalanyl-L-alanine-diazomethyl-ketone (ZPAD; BACHEM Bioscience, Inc., Torrance, Calif.), an inhibitor of cathepsins B and L (Shaw & Dean, *Biochem. J.* 186:385–390 (1980); Green & Shaw, *J Biol Chem.* 256:1923–1928 (1981); Richardson et al.,*J. Cell Biol.* 107: 2097–2107 (1988)) or vehicle (dimethylsulfoxide; DMSO, 0.01%–0.04%) for six days. This treatment media was exchanged every other day.

Cysteine protease inhibitors (calpain inhibitor I, III, calpeptin; Calbiochem, San Diego, Calif.) were added at 10–100 mM alone or in combination with ZPAD.

b. Histology

To prepare semithin sections, control and treated slices from both wild-type and apoE-deficient mice were fixed in a solution of 0.1M phosphate buffer ("PB"; pH 7.2), containing 1.5% paraformaldehyde and 1.5% glutaraldehyde. After a period of two to three hours, the solution was removed and the slices were rinsed three times in phosphate buffered saline ("PBS"; 50 mM phosphate buffer, 0.9% NaCl, pH 7.3). At this time, slices were postfixed in 2% osmium tetroxide in PB for one hour, dehydrated in a series of alcohols and embedded in Polybed-812. Semithin (1 μm thick) sections were cut on a Sorvall Porter-Blum ultramicrotome and stained with a solution of 0.1% toluidine blue. Digitized images were imported using a Sony DKC-5000 camera attached to a Zeiss microscope and processed using Adobe Photoshop™.

c. Immunoblotting

Control and ZPAD-treated slices were collected in ice-cold 10 mM Tris-HCl harvest buffer consisting of 0.32 M sucrose, 2 mM EDTA, 2 mM EGTA, and 0.1 mM leupeptin, pH 7.4, and centrifuged at 12,000×g for 5 minutes at 4° C. At this point, the pellets were resuspended in lysis buffer (8 mM HEPES, 1 mM EDTA, 0.3 mM EGTA, pH 8.0) and sonicated. The Bradford analysis was performed (Bradford, M, *Anal. Biochem* 72:248–254 (1976)) and 100–120 μg of protein from each sample was denatured by boiling for 5 min with 2.5% (wt/vol) sodium dodecyl sulfate (SDS) and 3% 2-mercaptoethanol and then subjected to SDS-PAGE on 10% linear gradient gels. See Laemmli et al., *J. Mol. Biol.* 47:69–85 (1970). Resolved proteins were then transferred to nitrocellulose membranes as described by Towbin et al., *Biotech.* 24:145–9 (1992), incubated in 3% gelatin in Tris-buffered saline ("TBS"; NaCl 8 g, KCl 0.2 g, Tris base 3 g in 1 liter distilled water, pH 7.4) for 1 hour at RT followed by incubation with 1% gelatin in TBS with 0.5% Tween 20 ("TTBS") containing an antibody that recognized tau-1 (1:100; Boehringer Mannheim, Indianapolis, Ind.) at RT overnight. Antibodies were localized by using the anti-IgG-alkaline phosphatase conjugates and the 5-bromo-4-chloro-3-indolyl-phosphate and nitro blue tetrazolium substrate system. Relative optical densities and areas of immunobands were quantified using the NIH image analysis system.

d. Immunohistochemical Procedures

For immunocytochemical staining, control and ZPAD-treated slices from both wild-type and apoE-deficient mice were fixed in 4% paraformaldehyde in 0.1 M phosphate buffer ("PB") at 4° C. overnight, rinsed once in a solution of phosphate buffered saline PBS (PB: phosphate buffer: 0.1M $Na_2HPO_4$ and $NaH_2PO_4$; PBS: phosphate buffered saline: NaCl 8 g, KCl 0.2 g, $Na_2HPO_4$ 1.44 g, $KH_2PO_4$ 0.24 g, dissolved in 1 liter distilled water, pH 7.4) cryoprotected in 20% sucrose in 0.1 M PB, sectioned on a freezing microtome at 25 μm parallel to the broad upper surface of the explant and mounted onto sterile Fisher Superfrost/Plus slides. After slides were preincubated with 10% normal goat serum (NGS) with 0.3% Triton X-100 for 1 hour at room temperature ("RT"), sections were incubated with monoclonal anti-PHF, AT8 (1:1000; Innogenetics, Belgium), in 5% NGS, at 4° C. overnight. The following day, the sections were rinsed in PBS and then incubated in biotinylated anti-mouse IgG (1:200, Vector) for 2–3 hours at RT, followed by avidin-biotin conjugate ("ABC") (1:100, Vector) diluted in PBS for 1 hour. The binding of the antibody was localized by using the avidin-biotin system (1:100, Vector) with kit reagents and diaminobenzidine as chromagen. As a control, tissue was processed through all incubations as described above except the primary antisera was omitted from the initial incubation.

e. Postembedding Immunocytochemistry

Lowicryl resin-embedded ultrathin sections (of 70–80 nm thickness) were picked up on either pioloform-coated nickel slot grids or pioloform-coated 400 mesh nickel grids. The grids were incubated on drops of blocking solution, followed by incubation on drops of primary antibodies (AT8 or PHF-1). After the incubation with primary antibodies, the sections were washed in TBS (three times for 10 min each) and in 50 mM Tris-HCl, pH 7.4, containing 0.9% NaCl ("TBS*"; once for 10 min; TBS* has 50 mM Tris-HCl and 0.9% NaCl without KCl, while TBS has 25 mM Tris-HCl and KCl) ) and incubated on drops of goat anti-mouse IgG coupled to 10 nm gold particles (British BioCell Int.). The secondary antibodies were diluted 1:100 in TBS* containing 0.05% polyethylene glycol 20000 (BDH; Merck) and 1% gelatin for 2 hr at 28° C. After additional washing in TBS* (three times for 10 min each) and PBS (once for 10 min), the sections were post-fixed in 2% glutaraldehyde in PBS for 2 min at room temperature and then washed in bidistilled water (three times for 10 min each). Finally, the sections were contrasted with saturated aqueous uranyl acetate followed by staining with lead citrate.

f. Electron Microscopic Analysis

For electron microscopic immunogold labeling, cultures were subjected to freeze substitution techniques as previously described (Schwarz et al., *Scann. Microsc.* 3 (Suppl.) :57–63 (1989); Van Lookem et al., *J. Histochem. Cytochem.* 39:1267–1279 (1991)). In brief, the specimens were cryoprotected by immersion in graded concentrations of glycerol (10, 20, and 30%) in phosphate buffer and plunged into liquid propane (−170° C.) in a cryofixation unit (KF 80; Reichert, Wien, Austria). The samples were then immersed in 0.5% uranyl acetate dissolved in anhydrous methanol (−90° C.) in a cryosubstitution unit (AFS; Reichert). The temperature was raised in steps of 4° C./h to −45° C. Samples were washed with anhydrous methanol and infiltrated with Lowicryl HM20 resin at −45° C. with a progressive increase in the ratio of resin to methanol. Polymerization was carried out with UV light (360 nm) for 48 h.

Ultrathin sections were cut with a Reichert ultramicrotome, mounted on nickel grids and processed for immunogold cytochemistry (Ottersen, *Anat. Embryol.* 180:1–15 (1989)). In brief, the sections were treated with a saturated solution of NaOH in absolute ethanol (2–3s), rinsed in phosphate buffer and incubated sequentially in the following solutions (at room temperature): (i) 0.1% sodium borohydride and 50 mM glycine in Tris buffer (5 mM) containing 0.01% Triton X-100 and 0.3% NaCl ("TBNT"; 10 min); (ii) 0.5% powdered milk in TBNT (10 min); (iii) primary antibody (AT8, 1:100; 2 h); (iv) same solution as in (ii) (10 min); and (v) gold-conjugated secondary antibodies (10 or 20 nm particles) diluted 1:20 in TBNT containing powdered milk and polyethylene glycol (5 mg/ml, 2 h). Finally, the sections were counterstained and electron micrographs obtained by a Philips CM10 transmission electron microscope.

II. Results

Morphological Studies

1. Morphology of Cultured Hippocampal Slices

Both wild-type and apoE-knockout mice hippocampal slices that were maintained in vitro for 12–14 days had morphologies similar to the morphologies of the hippocampus in vivo. The lamination of the hippocampus was clearly distinguishable even though the pyramidal neurons were slightly less compacted, in particular those of CA1 subfield. Neurons showed large centrally located nuclei and well differentiated prominent apical and basal dendrites. Within the cytoplasm, few basophilic organelles were found. No obvious morphological differences were observed between cultures from wild-type and knockout mice at the light microscopy level, although lack of efficient sprouting following culturing has been reported for apoE-deficient hippocampal cultures (Teter et al., *Neuros.* 91:1009–6 (1999)).

2. Morphological Changes Induced by Suppression of Cathepsins B and L

Incubation with 20 $\mu$M ZPAD for six days resulted in an increase in the number of basophilic granules in both wild-type and apoE-deficient hippocampal slices. Based on their size and distribution and their similar appearance to those found in earlier studies of ZPAD-treated rat cortical, hippocampal, hypothalamic, and entorhino-hippocampal slices (Bednarski et al., *J. Neurosci.* 17:4006–21 (1997); Bi et al., *Exp. Neurol.* 158:312–327 (1999); Yong et al., (1999); *Exp. Neurol.* 157:150–160 (1999)), these granules represent lysosomes. While densely stained organelles were evident in all subfields of hippocampus, a clear accumulation was found in CA3 subfield along fiber like structures that laminated the cell bodies on their apical dendrite side. From their location, these lysosomes appeared to be mostly contained in mossy fibers that project from granule cells to CA3 pyramidal neurons. The increase in the number of lysosomes and the appearance of clusters of basophilic granules in the mossy fiber terminal zone were observed in cultures from both wild-type and apoE-deficient mice. However, quantitative analyses of digitized images revealed that both phenomena were substantially enhanced in apoE-deficient hippocampal slice cultures. Additional pathologies were also found in the knockout cultures but were rare in wild-type ones. First, numerous large dark granules were found in the regions where apical dendrites end, in both CA1 and CA3 subfields. These granules are probably debris from degenerated cells. Second, neuropil in the molecular layers surrounding the hippocampal fissure thinned out and became more transparent, which also indicates neuritic degeneration. Finally, large neurons contained inclusions of different sizes and eccentrically localized nuclei were also frequently observed.

Enhanced Upregulation of Cathepsin D in apoE-deficient Hippocampal Slices

Figure 5A:
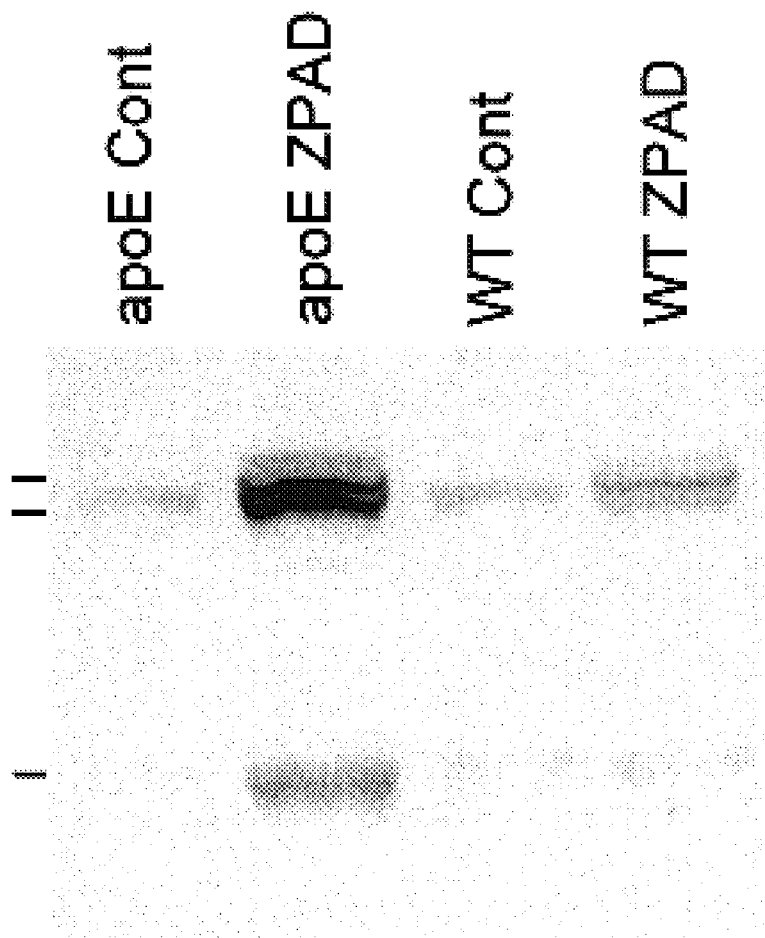

Immunoblotting was used to compare the concentrations of cathepsin D in slices from wild-type versus knockout mice. Cultured hippocampal slices had three major bands with apparent molecular weights of ~55 kDa, ~50 kDa, and ~38 kDa, corresponding to the inactive proenzyme, the active single chain, and the active heavy chain of cathepsin D, respectively (FIG. 5A). ZPAD treatment for six days reliably increased the first two isoforms in cultured wild-type slices. The proenzyme increased by 65±29% (mean±s.e.m.) relative to that in yoked controls that were not infused with ZPAD ($p<0.0001$, paired t-test, n=9, FIG. 5A). A smaller increase was obtained for the single chain form 42±22% ($p<0.0001$) but there were no evident effects on the heavy chain (3.0±5.7%, $p>0.5$). The differential effect of ZPAD across the isoforms was highly significant ($p<0.0001$, F=37.3, ANOVA), as were the differences in the increases between subunits ($p<.01$).

Figure 5B:
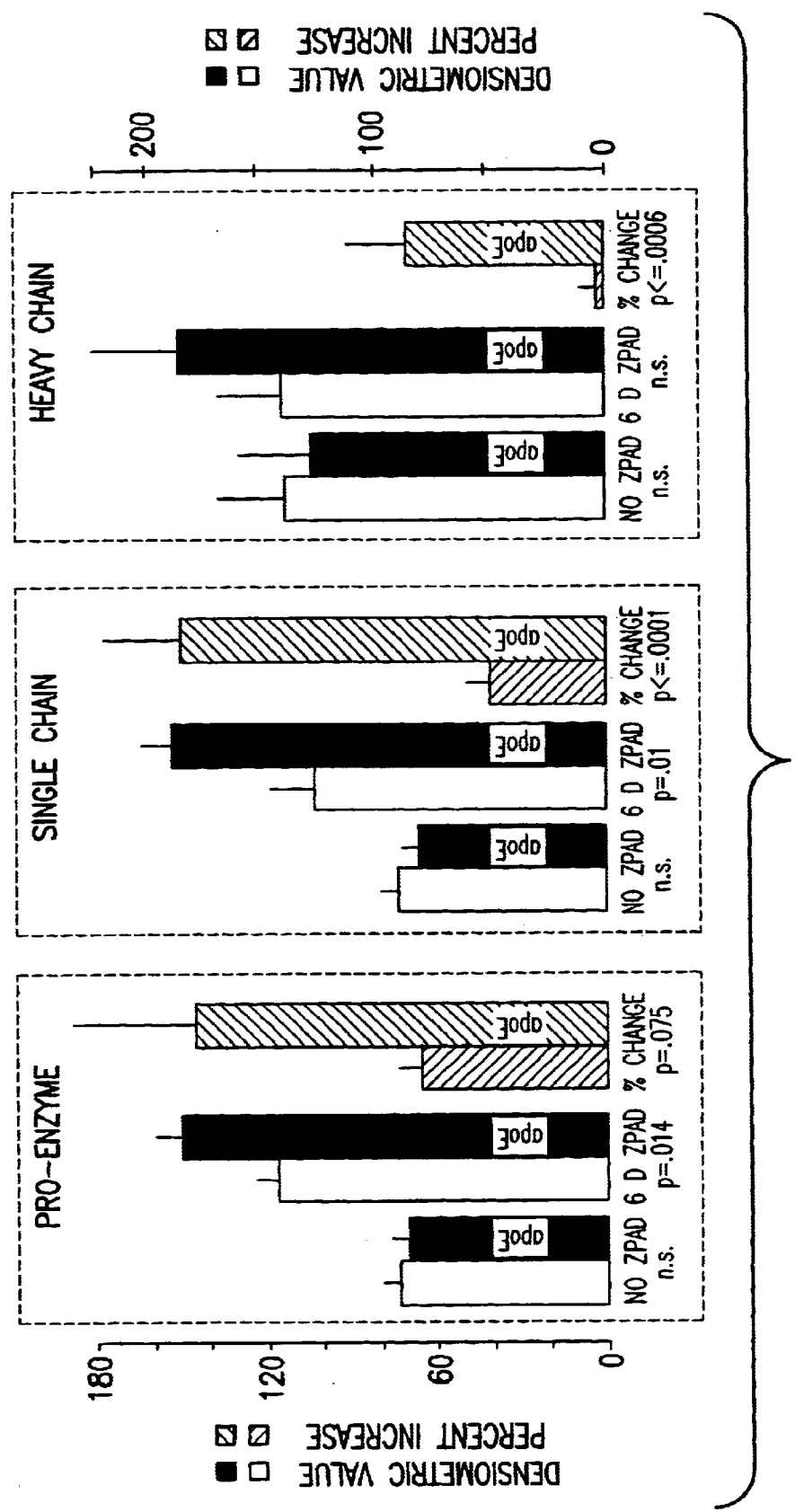

ZPAD produced more striking increases in the concentration of all isoforms of cathepsin D in apoE-knockout slices (FIG. 5A). Relative to yoked knockout controls, the inhibitor increased the proenzyme by 145±43% and the single chain by 150±29%. In contrast to the results obtained for the wild-type slices, ZPAD also caused a marked increase in the cathepsin D heavy chain relative to control values (84±26%, p=0.0006). It is noteworthy that the differential increase in the pro-enzyme versus single chain found for the wild-type slices did not occur in the slices from apoE-knockouts. The differences between wild-type and apoE-knockout slices with regard to ZPAD induced increases in cathepsin D isoforms were statistically significant (FIG. 5B).

In all, upregulation of cathepsin D in response to lysosomal dysfunction was substantially greater in apoE-deficient mice than in wild-type controls.

Enhanced Induction of Tangle-like Structures in Cultured Slices Prepared from ApoE-Knockout Rodents 1. Immunocytochemical Studies Immunocytochemical staining was carried out using monoclonal antibody "AT8" that recognizes full sized tau protein and tau protein fragments phosphorylated at residues Ser-202 and Thr-205.

Hippocampal slices from wild-type were treated with ZPAD. After six days of treatment with ZPAD, thick filaments that were densely stained by antibodies against hyper-phosphorylated tau were occasionally found within neurons in superficial layers of entorhinal cortex. The intracellular location and appearance of these structures corresponded to published descriptions of early-stage tangles. More mature tangle-like profiles were found at a number of sites after 12-day incubations. Immunoblots indicated that essentially all phosphorylated tau labeling in the slices involved proteins approximately 15–35-kDa in size, confirming that the immunostained filamentous structures were composed of tau fragments. While these results established that early-stage tangles follow from lysosomal dysfunction in cultured slices, the number of such profiles per unit area was far below that found in Alzheimer's disease brains.

Hippocampal slices from the apoE-knockout mice were treated with ZPAD as described above. Typical results are summarized in FIG. 2. Shown are sections through the CA1/subicular transition zone from a control slice (FIG. 2A) and from a slice incubated with ZPAD for six days, followed by six days washout (FIG. 2B). The material has been immunostained with antibodies developed against human tangles and that recognize phosphorylated tau and its 15–35 kDa fragment. These survey micrographs demonstrate that immunopositive structures are present in large numbers in the experimental slice, something that was not achieved with wild-type slices even after prolonged incubations. The dense structures were also absent from the control slices. The results shown in FIG. 2 are typical of effects obtained with different litters tested over a period of several months.

Closer examination revealed a number of types of "AT8" immunopositive structures. These different structures possibly represent cells at various stages of tangle formation, depicting a progression from early-stage tangles to cell death. Higher power micrographs of typical immunopositive structures are shown in FIG. 1. The cell marked as #1 has a dense structure at one pole of its soma and a thin, lightly labeled process. Other cells (e.g., #2c) have stained twisted processes emerging from the soma and ending in fragments. Another version of this can be seen in cell #3. In this instance the cell body is connected to a bulbous structure by a filament. The cell adjacent to #3 has a similar profile as well as a nearby sphere filled with well-stained filaments. It should be noted that the somata in most of these cases are anatomically distorted. The panel on the right side shows examples in which the cell appears to have ruptured and the immunostained fibrils have extruded into the extracellular space (#4 and #5). The selected cells (1–5) may represent stages of a progression from the intracellular buildup of tau fragments, to the development of intracellular tangles and abnormal processes, to cell death with persistence of the tangles.

Slices from wild-type mice without ZPAD treatment showed slight neuropil AT8-immunoreactivity and without evident cell body staining. In contrast, some of the untreated slices from apoE-deficient mice had low to moderate numbers of densely AT8-immunoreactive (AT8-ir) structures that were limited to the subiculum and hippocampal field CA1a (Sub/CA1a) and mainly located in stratum oriens. The number of these structures was significantly increased by application of ZPAD for six days and the affected areas expanded from Sub/CA1a to Sub/CA1a–c (FIG. 2B). Quite often AT8-ir neurons with larger cell bodies were also encountered in stratum lacunosum-molecular of field CA1. Occasionally AT8-ir cells were found in stratum oriens of field CA3. In contrast, hippocampal cultures from wild-type mice treated with ZPAD exhibited far fewer AT8-ir structures and the territory containing these structures was also much smaller. Unlike the case of ZPAD-treated apoE tissues where large numbers of AT8-ir structures were found in almost every single section, the incidence in ZPAD-treated wild-type sections was also lower.

To study the ultrastructure of tangle-like formations, electron microscopic immunogold technique was used. Numerous intracellular inclusions were found in cells that had been treated with ZPAD for 6 days. Shown in FIG. 3A is a dendritic branch with accumulated organelles resembling smooth ER (arrowheads), rough ER (asterisks), or mitochondria (M). Distorted microtubules were found passing through the abnormal inclusions. Despite these obvious pathologies, plasma membranes and synaptic apparatus were still distinguishable. Secondary lysosomes with variable sizes were also frequently encountered in ZPAD-treated tissues (FIG. 3B). Immunogold analysis showed that AT8-ir was found mainly over structures composed of distorted microtubules located throughout dendrites and cell bodies. Enlarged images showed that microtubules were often paired and twisted with axial periodicity (FIGS. 4A and B). Distorted microtubules were found running across each other or waving around, characteristics similar to early-stage neurofibrillary tangles in Alzheimer's disease (FIG. 4C).

2. Immunoblotting Studies

Immunoblots carried out using the antinonphosphorylated tau protein antibody, tau-1, detected a few moderately to densely immunopositive bands at ~50–55 kDa that corresponded to the different isoforms of native tau proteins in untreated hippocampal slice cultures from both apoE-knockout and wild-type mice. Occasionally, other stained bands were observed migrating at apparent molecular weights of 15–35 kDa, and were assumed to be breakdown products of tau. Tau isoforms and the breakdown product did not differ significantly between the two groups. Six days of ZPAD treatment resulted in a reduction in the native tau proteins in hippocampal slices from both apoE-knockout mice and wild-type mice. A statistic analysis showed that ZPAD-induced reduction was significantly greater in the knockout group than in wild-type group: 35±1.1% versus 22±2.6% (n=6, p<0.001). In parallel to the reduction of native tau, ZPAD treatment also increased the levels of the 15–35 kDa fragments in both groups. While the increase appeared to be larger in apoE-knockout mice than in wild-type mice, 277±20% vs 240±19%, the difference did not reach statistic significance.

Discussion

The above results provide, among other things, the following. 1) Tangle-like structures can be induced in culture slices in a medium which triggers lysosomal dysfunction and/or selectively increases cathepsin D. 2) Incubating cultured hippocampal slices from apoE-deficient mice with an inhibitor of cathepsins B and L for 6 days resulted in the formation of tangle-like structures in the subiculum and hippocampal field CA1 that was far more numerous than in wild-type mice. 3) Electron microscopic immunogold analysis revealed that the tangle-like structures were composed of distorted microtubules that had paired-helical like features. 4) Degradation of tau proteins was significantly greater in apoE-knockout than in wild-type mice.

Thus, the present invention provides a first instance in which tangle-like profiles have been induced in culture slices. Moreover, the present invention provides clear evidence, for the first time, for the relationship between a predisposing condition of Alzheimer's disease, apoE, and the formation of neurofibrillary tangles, one of the major pathologies in Alzheimer's disease. The location of tangle-like structures corresponds to that in tissues from Alzheimer's disease patient. The tangle-like structures are composed mainly of tau fragments that are similar in size as discovered in neurofibrillary tangles in Alzheimer's disease.

Neurofibrillary tangles have long been recognized as the hallmarks of Alzheimer's disease and the existence of a close correlation between the presence and distribution of neurofibrillary tangles and the degree of cognitive impairment in Alzheimer's disease further emphasizes the critical role of tau pathology in the development of the disease. Hyperphosphorylated tau proteins tend to dissociate from microtubule and assemble into paired helical filaments. Other factors proposed to facilitate the aggregation of tau include oxidation, polyanions, and nucleation. In vitro tests have demonstrated that all tau isoforms are able to aggregate, however, tau fragments containing the repeat domain exhibit faster kinetics in in vitro assembly tests. Thus, not wishing to be bound by a theory, fragmentation of tau could be a significant factor that enhances the aggregation of tau and causes the generation of tangle like structures.

Incubation of hippocampal slice cultures from mice with an inhibitor of cathepsins B and L resulted in 15–35 kDa tau fragments and AT8-ir structures that resembled early-stage tangles. However, generation of large numbers of tangle-like structures was only observed in apoE-knockout mice. Hyperphosphorylated tau immunopositive neurons were also found in field subiculum and CA1 areas in some untreated apoE-knockout slices, even though the numbers were much smaller than in ZPAD-treated apoE slices. Further statistic analysis showed that the incidence of the spontaneous AT8-ir neurons found in apoE-knockout mice was also lower than that in ZPAD-treated wild-type tissue. Not wishing to be bound by a theory, these results suggest that while apoE deficiency and lysosomal dysfunction are both facilitating factors for the formation of tangle-like structures, lysosomal dysfunction seems more potent. The effects of these two factors are not simply additive because the number of tangle-like structures in ZPAD-treated apoE tissues was more than double that in apoE-untreated or ZPAD-treated wild-type slices. Thus, lack of apoE gene makes the tissue extremely susceptible to pathologies associated with lysosomal dysfunction.

ApoE is a major risk factor for late onset sporadic Alzheimer's disease: apoE is co-localized with the neurofibrillary tangles and senile plaques, and the burden of both A-beta-containing plaques and neurofibrillary tangles is increased in a dose-dependent manner in Alzheimer's disease patients with apoE4. In vitro experiments showed that apoE2 and apoE3 were able to bind to microtubules and form stable complexes with the microtubule-associated proteins tau and MAP2c while apoE4 lacks this ability (Strittmatter et al. (1994), supra). Not wishing to be bound by a theory, apoE3, by binding to tau, protects tau from being hyperphosphorylated and thus prevents the generation of intracellular neurofibrillary tangles. On the other hand, the formation of apoE-tau complex has been shown to be dependent on the phosphorylation state of tau; phosphorylation of Ser262 within the microtubule binding domain of tau has been shown to prevent binding of apoE (Huang et al., *Neurosci Lett.* 192:209–12 (1995)). Therefore, the phosphorylation state of tau proteins, altered by missing the stabilization effect from apoE (that is more like apoE3), could be one of the reasons that more tangle-like structures were formed in knockout mice.

Among other things, the present invention provides that tangle-like structures can be induced in brain cells by contacting the brain cells with a medium that triggers lysosomal dysfunction and/or increases cathepsin D. Moreover, the present results demonstrated that the absence of apoE significantly enhanced the susceptibility of the tissue to insults that caused lysosomal dysfunction, and the induction of neurofibrillary tangles.

Example 2

Increases in Cathepsin D Associated with Lysosomal Dysfunction are Enhanced in Apolipoprotein E-Knockout Mice As apoE is currently the only confirmed risk factor for late-onset Alzheimer's disease, tests were undertaken to determine whether upregulation of cathepsin D, a sign of Alzheimer's disease pathology, is more pronounced in slices from apoE-deficient than in wild-type mice. Immunoblotting stained with anti-cathepsin D showed that homogenates of cultured hippocampal slices exhibited three major bands with apparent molecular weights of ~55 kDa, ~50 kDa, and ~38 kDa, corresponding to the inactive proenzyme, the active single chain, and the active heavy chain of cathepsin D, respectively (FIG. 5A). ZPAD treatment for six days reliably increased the first two isoforms in cultured slices from wild-type mice. The proenzyme increased by 65±29% (mean±s.e.m.) relative to that in controls that were not infused with ZPAD ($p<0.0001$, paired t-test, n=9, FIG. 5B). A smaller increase was obtained for the single chain form (42±22%; $p<0.0001$), but there were no evident effects on the heavy chain (3.0 ±5.7%, $p>0.5$). The differential effect of ZPAD across the isoforms was highly significant ($p<0.0001$, F=37.3, ANOVA) as were the differences in increases between subunits ($p<0.01$).

ZPAD produced more striking increases in the concentration of all isoforms of cathepsin D in apoE-knockout slices (FIG. 5A). The proenzyme was increased by 145±43% and the single chain by 150±29%. In evident contrast to the results obtained for the slices from wild-type mice, ZPAD also caused a marked increase in the cathepsin D heavy chain (84±26%, $p<0.01$). It is noteworthy that the differential increase in pro-enzyme versus single chain found in slices from wild-type mice did not occur in slices from apoE-knockouts. The differences between wild-type and apoE-knockout with regard to ZPAD-induced increases in cathepsin D isoforms were statistically significant (FIG. 5B).

In all, the results demonstrate that upregulation of cathepsin D in response to lysosomal dysfunction is substantially greater in apoE-deficient mice than in wild-type controls.

Example 3

Regional Induction of Intraneuronal Neurofibrillary Tangles in Cultured Slices Prepared from ApoE-Knockout Mice Cultured hippocampal slices prepared from apoE-deficient mice were exposed to an inhibitor of cathepsins B and L and then processed for immunocytochemistry using antibodies against human paired helical filaments.

Dense, immunopositive deposits were found in the subiculum, stratum oriens of field CA1, and the hilus of the dentate gyrus. This distribution agrees with that described for tangles in AD. The appearance of the labeled structures fell into categories that correspond to previously proposed stages in the progression of intraneuronal neurofibrillary tangles in human hippocampus. Electron microscopic analyses confirmed that microtubule disruption and twisted filaments were present in neurons in the affected areas. These results support the hypothesis that partial lysosomal dysfunction is a contributor to Alzheimer's disease and suggest a simple model for studying an important component of the disease.

Cultured hippocampal slices were prepared from 10–12 day old C57BL/6J-apoE$^{tm1Unc}$ (apoE-knockout or apoE –/–) or C57BL/6J (wild-type) mice and kept in vitro for 12–14 days before being exposed to medium containing ZPAD, a selective inhibitor of cathepsins B and L (Bahr, B. A., et al., *Exp. Neurol.* 129:1–14 (1994); Heinonen, O., et al., *Neuroscience* 64:375–384 (1995); Heffernan, J. M., et al., *Exp. Neurol.* 150:235–239 (1998) ) or vehicle (DMSO, 0.04%) for 6 days. Immunocytochemical staining was carried out using monoclonal antibody "AT8" which recognizes the full-length human tau protein (and tau fragments) phosphorylated at residues Ser-202 and Thr-205. The results described here involved detailed analysis of multiple sections from 30 apoE –/– and 30 wild-type slices treated with ZPAD. A smaller number of vehicle alone slices in each group were also examined. Double labeling to confirm the identification of cells as neurons was carried out in four apoE –/– slices using an antibody against neuronal nuclear protein.

Slices from knockout mice were comparable in size and appearance to their wild-type counterparts. Some, but not all, untreated apoE –/– slices had labeled cells in the outgrowth zone that develops in the first week after explantation. However, immunopositive neurons were only rarely found within the dendritic and cell body layers of hippocampus itself (FIG. 6, right panel).

Numerous, densely stained neurons were present within hippocampus and retrohippocampal cortex in nearly all of 30 apoE –/– slices treated with ZPAD for 6 days. These were numerous in the subiculum and field CA1 and relatively uncommon in dentate gyrus and field CA3. Within CA1 the profiles were usually much more frequent in the stratum oriens than in the pyramidal cell layer or stratum radiatum. This can be seen clearly in the higher power micrograph presented in FIG. 8. This figure also illustrates the extent to which most neurons and their processes were unstained by the PHF antibody, even in apoE –/– slices treated with ZPAD. Note, for example, that the densely packed cell bodies in stratum pyramidale, as well as the profusion of apical dendritic branches in stratum radiatum, are barely detectable in the micrograph. The pattern seen in FIGS. 6 and 8 held for most slices; a common variation involved the presence of significant numbers of labeled cells in the s. pyramidale and s. radiatum of field CA1 and in the hilus of the dentate gyrus.

Effects of the type just described were not seen after much longer treatments in prior studies using cultured slices from rat hippocampus (Jicha, G. A., et al., *J Neurosci* 19:7486–7494 (1999) ). Wild-type mice were intermediate between rats and apoE –/– mice. Slices with clear anatomical landmarks in the CA1 /subiculum boundary region were selected for estimating the magnitude of the difference between the two mouse groups. Counting was done in a 0.3 mm$^2$ box centered over the stratum oriens/pyramidal layer at the CA1/subicular border. The number of AT8 immunopositive profiles in the knockouts was 193.8±15 (mean±s.e.m., n=5) and 112.6±13 (n=5) in the wild-types, a difference that was highly significant (p=0.005, two-tail t-test). These results confirm that the apoE mutation contributes to the formation of intraneuronal neurofibrillary tangles.

While ZPAD had robust and reliable effects across apoE –/– slices, the immunopositive cells within a given slice were not homogeneous in appearance. Most of the labeled neurons were shrunken and had 'polar caps'; i.e. dense deposits located eccentrically within the somata. Examples of these are marked as '1' in FIG. 7. The degree of cell shrinkage can be appreciated by comparing the immunopositive elements to the unlabeled neuron outlined within the stratum pyramidale. In many cases the cells had immunopositive processes extending away from the somata for considerable distances. Neurons with labeled, pathological dendrites ('2' in FIG. 7) as well as 'caps' of labeled material unconnected to cell bodies ('3' in FIG. 7) were also commonplace throughout the stratum oriens and subiculum. The isolated 'caps' may be remnants of neurons. Double labeling experiments (not shown) confirmed that the shrunken profiles were neurons.

The variety of densely stained elements found in the ZPAD-treated apoE –/– slices is not unlike the diversity of intraneuronal NFTs found in hippocampus during early-stage Alzheimer's disease and/or other related disorders. This point is illustrated in FIG. 8. The upper panels, from an apoE slice, are higher power micrographs organized according to a progression along the lines proposed for NFT development in Alzheimer's disease (Chin, J. Y., et al., *J Neuropathol Exp Neurol* 59:966–971 (2000); Auer, I. A., et al., *Acta Neuropathol* (Berl) 90:547–551 (1995)). The steps are as follows: Panel A. Essentially intact neurons with immunopositive cell bodies and dendrites; Panels B & C. Dense, localized deposits within the cell body accompanied by evident dendritic abnormalities such as clubbing (arrow); Panels D & E. Expansion of initial dendritic segments; Panel F. Loss of dendritic organization, sometimes accompanied by the growth of large filament filled structures resembling growth cones (arrows); Panels G & H. Disappearance of the neuron leaving a cap of labeled material.

The bottom panels of FIG. 8 are from field CA1 of an early-stage human Alzheimer's disease brain. Immunostaining was carried out with the same procedures and antibody used for the sections from the apoE slices. Panel A shows a typical neuron with labeled dendrite and cell body 'cap' (arrow). Panels B, C, & D illustrate the dendritic abnormalities that are commonplace at this stage of the disease. Note the apparent clubbing and fragmentation (arrows) at sites removed from the cell body. Panel E shows a swelling proximal to the soma; examples of neuronal remnants are found in panels F & G.

Electron microscopic analyses of zones with labeled neurons confirmed that the pathological changes detected with PHF antibodies were accompanied by the development of aberrant filaments. The proximal apical dendrite was often nearly filled with a dense plexus of filamentous material, as shown in the micrograph in FIG. 9A. Closer examination of the filaments from this (FIG. 9B) and other (e.g., FIG. 9C) neurons shows them to be long twisting structures that frequently cross each other (arrows). Figures of this type were unique to ZPAD-treated slices.

Several lines of evidence indicate that NFTs assemble from mixtures of tau and tau fragments (von Bergen, et al., *Proc Natl Acad Sci USA* 97:5129–5134 (2000); Pei, J.-J., et al., *J Neuropathol Exp Neuro* 58:1010–1019 (1999) ), and it is likely that tau proteolysis is an essential step in tangle formation. Accordingly, immunoblots were used to test if accelerated breakdown of tau might account for the enhanced build-up of intraneuronal NFTs in the apoE –/– slices. The antibody 'tau-1' detected a set of tau isoforms (50–55 kDa) in untreated hippocampal slice cultures from both apoE –/– and wild-type mice. Six days of ZPAD treatment caused a 22±2.6% (mean±s.e.m.) reduction in native tau in slices from wild-type animals and a 35±1.1% reduction in apoE-knockout slices (n=6, p<0.001, t-test).

Example 4

Induction of Early-Stage Neurofibrillary Tangles is Triggered by Cholesterol-Lowering Agents; These Effects are Enhanced by Lysosomal Dysfunction and Include Glial Reactions and the Upregulation of Cytokines The inhibition of cholesterol synthesis induced tangle-like structures in cultured rat hippocampal slices and this effect was markedly enhanced in the presence of ZPAD.

To test the effect of manipulating intracellular lipid levels on lysosomal dysfunction-induced tangle formation, cultured rat hippocampal slices were incubated with ZPAD in the presence of the lipid metabolism inhibitor, mevastatin. Incubation of rat hippocampal slices with ZPAD results in only a small number of anti-phosphorylated tau (AT8) immunoreactive (ir) structures. However, in the presence of a cholesterol-lowering agent (mevastatin), ZPAD treatment caused robust induction of tangle-like structures. As shown in FIG. 10, and FIG. 11, these AT8-ir cells exhibited similar morphological characteristics as those found in cultured slices from apoE-deficient mice. Moreover, the regional distribution of AT8-ir in the ZPAD plus mevastatin treated slices were mainly observed in the subiculum and field CA1, areas showing AT8-ir neurons in apoE-deficient cultures. AT8 immunostaining is moderately increased in ZPAD or mevastatin-treated tissue, and a further increase is present in the mevastatin plus ZPAD treatment groups. Similar results were observed in six different experiments.

These results suggest that cholesterol-lowering agents, and specifically inhibitors of lipid metabolism, and more specifically inhibitors of cholesterol synthesis, may produce significant neurodegenerative-like pathologies. It is noteworthy that incubation of cultured slices with mevastatin alone resulted in tangle-like structures and that knockout animals were not used.

Immunoblotting results showed that the combined application of mevastatin and ZPAD induced a novel tau breakdown product with an apparent molecular weight of ~33 kDa when probed with tau-1 antibody that reacts with the non-phosphorylated protein. Western blots probed with AT8 antibody that recognized the phosphorylated forms, showed that the 33 kDa breakdown products were markedly enhanced in samples from mevastatin/ZPAD AND mevastatin only (FIG. 12). These results suggest that the 33 kDa breakdown products exist in both phosphorylated and non-phosphorylated form, and the ZPAD plus mevastatin treatment increases the former more than the latter.

Immunoblotting was carried out by using anti-non phosphorylated tau antibody, tau-1 or anti-phosphorylated tau antibody, AT8. Densitometric analysis of blots stained with tau-1 antibody showed that while ZPAD treatment induced decreases in the native tau proteins and increases in fragments at apparent molecular weights of 40, 33, and 29 kDa, combined application of ZPAD and mevastatin enhanced the increase in levels of p33 fragments (FIG. 12, upper panel). The lower panel of FIG. 12 shows levels of p33 tau phosphorylated at residues 199 and 202 (detected with AT8 antibody.) *, p<0.05, ** p<0.01.

Several protein kinases have been shown to be involved in the phosphorylation of tau proteins. Among these are cyclin dependent protein kinase 5 (cdk5) and mitogen activated protein kinase (MAPK). FIG. 13 shows that treatment of cultured hippocampal slices with mevastatin induced significant decreases in the levels of p35, the regulatory component of cdk5.

FIGS. 14A and 14B illustrate the dose response and time course of p35 following mevastatin or mevastatin plus ZPAD treatment. Hippocampal slices were cultured from 12 day-old rat pups and kept in vitro for 12 days before exposure to mevastatin. For the dose curve experiments, slices were subjected to mevastatin for 6 days at 0 $\mu$M, 1 $\mu$M, 5 $\mu$M 10 $\mu$M, and 100 $\mu$M concentrations. For the time course experiment, hippocampal cultures were incubated with 10 $\mu$M mevastatin for 0, 2, 4, and 6 days. In the mevastatin plus ZPAD treatment, ZPAD was used at 20 $\mu$M. Hippocampal slices were collected, homogenized, and subjected to SDS-PAGE electrophoresis. Immunoblots were then probed with anti-p35 sera that were raised against the C-terminal domain of p35.

Down regulation of p35 by mevastatin is blocked by the application of mevalonate (FIG. 15). Hippocampal slices were prepared from apoE-knockout mice at postnatal day 13, cultured in vitro for 12 days, and then incubated with vehicle alone (control), mevastatin, mevastatin plus ZPAD, EA1, cholesterol, or mevalonate, a product of HMG-CoA reductase. Down regulation of p35 induced by mevastatin is completely blocked by mevolonate.

Increasing evidence has indicated that inflammation is an important component of AD-related pathology (Akiyama, H., et al., *Neurobiol. Aging* 21:383–421 (2000); Rogers, J., et al., *Neurobiol. Aging* 17:681–686 (1996); Eikelenboom, P., et al., *Exp. Neurol.* 154:89–98 (1998) ). For instance, classic features of immune reactions have been found in Alzheimer's disease brains, including increases in proinflammatory cytokines, activation of microglia and astrocytes, and the existence of complement proteins in neuritic plaques. Epidemiological studies have shown that the use of non-steroidal anti-inflammatory drugs reduces the risk and slows the progression of the disease.

To determine whether experimentally-induced tangle-like structures were also associated with inflammatory reactions, mRNA levels for several cytokines were analyzed by the RT-PCR technique. Additionally, the activation of mitogen-activated protein kinase (MAPK) has been implicated in the activation of microglia, thus tests were undertaken to determine the effects of an inhibitor of MAPK kinase (PD98059), and to assess if MAPK is involved in neurofibrillary tangle formation. mRNA levels for certain cytokines were decreased by PD98059 treatment (FIG. 16). Treatment of cultured hippocampal slices with mevastatin or ZPAD-triggered increases in cytokines TGF and IL-10. The combination of mevastatin and ZPAD (Mev/ZPAD) markedly increased the levels of both TGF and IL-10 mRNA. PD98 and PD98/ZPAD are groups treated with PD98059 (a mitogen-activated protein kinase inhibitor) or PD98059 plus ZPAD respectively. Upregulation of cytokine mRNAs is specific to the disruption of lipid metabolism.

RT-PCR and Northern Blot Analyses of Cytokines

Increases in pro-inflammatory cytokines including IL1-alpha, IL1, IL6, and IL10, TNF-alpha, and TGF have been reported in Alzheimer's disease brains. To characterize glial reaction following ZPAD and mevastatin treatment, the levels of mRNA for these cytokines were analyzed by RT-PCR.

Levels of mRNA for the cytokines were quantified by RT-PCR and northern blot analysis, following protocols outlined in the RT-PCR kit (Ambion Inc.). The results demonstrated that experimentally-induced lysosomal dysfunction and/or application of mevastatin (20 $\mu$M) increased mRNA levels of TGF-beta and IL-10.

Treatment of cultured hippocampal slices with mevastatin triggered increases cytokine TNF-alpha. (FIG. 17). Note, only the inhibitor of cholesterol metabolism, mevastatin, appeared to markedly increase the level of TNF-alpha.

Immunocytochemical Studies of Microglial Activation

Immunocytochemical studies using the monoclonal antibody ED-1 that recognizes reactive microglia were used at 1:1000 dilution following standard immunohistochemical procedures. Microglial activation was determined by measuring cell numbers, optical density, and size of cell bodies using the program NIH Image.

Brain tissue was cultured for 12 days and treated with ZPAD (20 $\mu$M) in the presence or absence of PD98059 (50 $\mu$M) for 6 days (FIG. 18). Cultured explants were then sliced and stained by using monoclonal antibody ED-1 which recognizes reactive microglia, a classical marker of inflammation. Note that incubation with ZPAD triggered significant reaction of microglia, and this reaction was completely blocked by co-application of PD98059. Inhibition of MAPK by itself did not induce evident changes in microglia.

Rat brain tissues were cultured for 10 days and incubated with vehicle (Cont), ZPAD (20 $\mu$M), mevastatin (Mev, 20 $\mu$M), or mevastatin plus ZPAD (Mev/ZPAD) for 6 days (FIG. 19). Cultured brain explants were then sliced and stained by using monoclonal antibody ED-1, a classical marker for reactive microglia and macrophages. Note that treatment with ZPAD triggered significant reaction of microglia that became larger and their cell bodies were filled with ED1 immunopositive granules. Treatment with mevastatin induced dramatic morphologic changes of microglia; these cells became round and lost their characteristic thin processes. However, ED1-stained granules that resemble phagosomes were evident in most cells, suggesting the transformed cells maintained their phagocytic character.

FIG. 20 is an immunoblot using anti-active MAPK (Sigma, 1:10,000). FIG. 20 demonstrates that MAPK (ERK1/2) was activated by ZPAD and mevastatin treatment in the hippocampal slices. Not only did application of mevastatin and ZPAD activate MAPK, but also this effect was blocked by MAPKK inhibitor PD98059.

FIGS. 21A and 21B show the response and time course of MAPK following mevastatin treatment. Cultured hippocampal slices were treated with mevastatin or mevastatin plus ZPAD. For the dose curve experiments, slices were subjected to mevastatin for 6 days at 0 $\mu$M, 1 $\mu$M, 5 $\mu$M, 10 $\mu$M, and 100 $\mu$M concentrations. For the time course experiment, hippocampal cultures were incubated with 10 $\mu$M mevastatin for 0, 2, 4, and 6 days. In the mevastatin plus ZPAD treatment, ZPAD was used at 20 $\mu$M. Immunoblots were probed with the monoclonal anti-MAPK/ERK antibody that recognizes the diphosphorylated (activated) isoforms of MAPK.

Summary

These results demonstrate that: a) compounds that inhibit cathepsin D block the formation of tau fragments; b) upregulation of cathepsin D in response to lysosomal impairment is greater in brain tissue from ApoE-knockout mice than in brain tissue from wild-type controls or from rats; c) neurofibrillary tangles are far more frequent and develop more quickly after the onset of lysosomal dysfunction in brain tissue from apoE-knockout mice than in brain tissue from wild-type controls or from rats; d) disturbance of cholesterol synthesis and/or availability and/or levels of cholesterol induces neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases, and these effects are further enhanced by lysosomal dysfunction; e) the increases in neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases triggered by lysosomal dysfunctions and/or increases in Cathepsin D and/or decreases in cholesterol levels are blocked by inhibitors of mitogen-activated kinases, f) inflammation co-exists with early-stage neurofibrillary tangles. The instant invention reproduces cardinal features of neuropathology including: hyperphosphorylation of tau, fragmentation of tau, formation of neurofibrillary tangles, increased production and/or release of cytokines, increased microglia reaction and/or activation, increased inflammation, and/or increased conversion of p35 to p25 changes in the levels and activities of protein kinases, and/or other characteristics of neurodegeneration, including Alzheimer's disease.

Example 5

Tau Fragmentation and the Formation of Neurofibrillary Tangles is Blocked by Inhibition of the Cysteine Protease Calpain Cultures of hippocampal slices were prepared from 10–12 days old rats. Slices were kept in vitro for 12–14 days before being exposed to a medium containing ZPAD (a selective inhibitor of cathepsins B and L) and/or vehicle (DMSO, 0.04%) for 6 days and/or a cysteine protease inhibitor (calpain inhibitor I).

A. Lysosomal Dysfunction Induced Conversion of p35 to p25 was Blocked by Calpain Inhibitors.

Immunoblotting carried out using antisera that recognizes the C-terminal domain of p35 showed that the CDK5 binding protein p35 was present in cultured hippocampal slices. Trace amount of p25, the truncated form of p35 that lacks the N-terminal domain, was also detected. A six day treatment of the brain cells with ZPAD (a selective inhibitor of lysosomal hydrolases cathepsin B and L) resulted in a significant decrease in the amount of p35 polypeptide and a paralleled increase in the truncated form p25. Such conversions of p35 to p25 were significantly inhibited in the presence of calpain inhibitor I (see FIG. 22).

B. Tau Fragmentation Events Triggered by Experimentally Induced Lysosomal Dysfunction were Blocked by Calpain Inhibitors.

Immunoblots stained with the anti-non-phosphorylated antibody (tau 1), revealed that 6-day ZPAD treatment induced a truncation of native tau proteins and the generation of tau fragments that migrated at about 40 kDa, 29 kDa (tau 29), and 15–35 kDa. Previous studies have shown that cathepsin D is a protease whose activation leads to the cleavage of tau. Incubation with cathepsin D inhibitors remarkably reduced the production of tau 15–35 induced by ZPAD treatment, but the cathepsin D inhibitors failed to block the increase in the 40 kDa fragments. Such results suggested that another protease may be activated by the ZPAD treatment. A previous study had suggested that calpain was able to cleave tau and generate tau fragments of different lengths. See Mercken et al., FEBS letters, 368 (1995). To test whether calpain is involved in ZPAD-induced tau cleavage, levels of tau fragmentation were compared between slices incubated with and without calpain inhibitors. Results obtained from 2 separate experiments showed that ZPAD-induced tau 15–35 and tau 40 were almost completely blocked by calpain inhibitor I (See FIG. 23).

C. ZPAD-induced Tangles were Blocked by Calpain Inhibitors.

Incubation of hippocampal slices with ZPAD for 6 days induced numerous tangles, in particular, in the border of subiculum and CA1 region. However, when ZPAD was applied in the presence of calpain inhibitor I, the number of tangles was significantly reduced (See FIG. 24).

The above results provide, among other things, the following. 1)-The formation of tangle-like structures can be inhibited by contacting brain cells with a cysteine protease inhibitor. 2) The formation of tangle-like structures, induced in brain cells by contacting such cells with a medium which selectively increases cathepsin D, can be inhibited by contacting the cells with a cysteine protease inhibitor. 3) Degradation of tau proteins was significantly inhibited by contacting the brain cells with a cysteine protease inhibitor.

Thus, the present invention provides a first instance in which tau proteolysis capable of triggering the formation of neurofibrillary tangles has been inhibited by a cysteine protease inhibitor. Moreover, the present invention provides clear evidence, for the first time, for the relationship between cysteine proteases, tau proteolysis, and the formation of neurofibrillary tangles—one of the major pathologies in Alzheimer's disease. The location of tau proteolysis and tangle-like structures inhibited in brain cells by such protease inhibitors corresponds to that in tissues from Alzheimer's disease patient. Such tangle-like structures are composed mainly of tau fragments that are similar in size as discovered in neurofibrillary tangles in Alzheimer's disease.

Neurofibrillary tangles have long been recognized as the hallmarks of Alzheimer's disease and the existence of a close correlation between the presence and distributions of neurofibrillary tangles and the degree of cognitive impairment in Alzheimer's disease further emphasizes the critical role of tau pathology in the development of the disease.

Hyperphosphorylation and fragmentation of tau have both been previously proposed to be key steps involved in the aggregation of tau into paired-helical filaments and thus key steps in the production of neurofibrillary tangles. Therefore, one way that calpain could facilitate tangle formation is through indirectly increasing the phosphorylation of tau. Calpain could trigger such phosphorylation by cleaving p35 to p25 (p25 is known to be more active than p35 with regard to the phosphorylation of tau).

In vitro tests have demonstrated that all tau isoforms are able to aggregate, however, tau fragments containing the repeat domain exhibit faster kinetics in in vitro assembly tests. Thus, not wishing to be bound by a theory, fragmentation of tau could be the key factor that enhances the aggregation of tau and causes the generation of neurofibrillary tangles, and therefore the inhibition of such fragmentation of tau by the application of a cysteine protease inhibitor may be a viable therapeutic option for diseases and disorders comprising pathologies related to tau fragmentation. These results significantly extend the range of neurodegenerative disease features that can be induced and/or inhibited in brain cells.

Example 6

Induction of Tangle-like Structures by ZPAD Treatment was Blocked by Mitogen-Activated Kinase Inhibitors Incubation of hippocampal slices with ZPAD for 6 days induced numerous tangles, in particular, in the border of subiculum and CA1 region. However, when ZPAD was applied in the presence of a mitogen-activated kinase inhibitor, the number of tangles was significantly reduced (FIG. 25).

Example 7

Modulation of Biological Processing of Amyloid Precursor Protein by Mevastatin Treatment is Blocked by Mevalonate Hippocampal slices were prepared from apoE-knockout mice at postnatal day 13, cultured in vitro for 12 days, and then incubated with vehicle alone (control), mevastatin, mevastatin plus ZPAD, EA1, cholesterol, or mevalonate, a product of HMG-CoA reductase (FIG. 26). Tissues were processed for immunoblotting and assessed by monoclonal antibody 22C11, which recognizes the N-terminal domain of amyloid precursor protein (APP). Mevastatin treatment markedly increased the levels of full length APP and induced a novel band with molecular weight slightly lower than the native APP. Whether this new product is due to proteolysis or changes in protein maturation is under investigation. When mevastatin was applied in the presence of mevalonate, its effects on APP were completely blocked.

Example 8

Effects of Mevastatin on APP were Partially Blocked by MAPKK Inhibitor PD98059, but not by Inhibitor SB203580 of MAPK p38

Hippocampal slices were incubated with vehicle alone/control, mevastatin, mevastatin plus ZPAD, mevastatin plus PD98059, mevastatin plus EA1, mevastatin plus cholesterol, mevastatin plus mevalonate, mevastatin plus SB203580, or mevastatin plus y-secretase inhibitor (FIG. 27). These results showed that treatment of hippocampal slices with mevastatin rapidly and markedly decreased levels of p35, increased activated forms of MAPK, and increased levels and proteolytically processed APP. The observation that both decrease in p35 and increase in APP were completely blocked in the presence of mevalonate, the product of HMG-CoA reductase, strongly indicates that the effects of mevastatin are due to disruptions in cholesterol biosynthesis. The effects of mevastatin on APP bioprocesses were partially blocked by MAPKK inhibitor PD98059 but not inhibitor of MAP kinase p38 SB203580, suggesting MAPK/Erk1/2 is involved in mevastatin induced changes in APP metabolisms.

Example 9

Lysosomal Dysfunction Induces Increased Activity of Caspase 3

Hippocampal slices were cultured for 12 days and incubated with vehicle alone, ZPAD, or chloroquine (CQN; a lysosomal inhibitor) for 6 days (FIG. 28). Cultures were then homogenized, and subjected to an ELISA assay to detect the activity of caspase 3, an apoptotic protease. ZPAD treatment caused a marked increase in the activity of caspase3.

Example 10

Pravastatin, Simvastatin, and Mevastatin Produce Neurodegeneration—In Vitro and In Vivo Pravastatin treatment induces the formation of tangle-like structures (FIG. 29). Cultured rat hippocampal slices of 12 days in vitro were treated with 20 $\mu$M pravastatin for 6 days and processed from immunohistological studies with the monoclonal antibody AT8. The subiculum, CA1 field, and CA3 field of the hippocampus were examined by photomicroscopy.

Microglial reactions are induced by mevastatin and simvastatin treatments (FIG. 30). Male Sprague-Dawley rats age 2½ months were injected daily (i.p.) with vehicle (n=3), mevastatin (10 mg/kg, n=3), or simvasatin (10 mg/kg, n=4) for 39 days, and killed by with overdose of sodium pentobarbital (200 mg/kg, i.p.) and perfused intracardially with phosphate buffered saline (PBS, pH 7.4) followed by 4% paraformaldehyde in 0.1 M phosphate buffer (PB, pH 7.4). Brains were then removed, postfixed in perfusate for 5–6 hors, and cryoprotected in 15% sucrose/PB followed by 30% sucrose/PB (12–24 hours each) at 4° C. Coronal sections were cut at 20–30 $\mu$m by using a freezing microtome and collected into PBS. Immunostaining was performed as described for the in vitro experiments using monoclonal antibody CD11b that reacts with both active and non-active microglia.

Shown are images of hippocampal areas from one control animal and an animal treated with simvastatin. CD11b immunostaining is moderate to dense in control tissue, while it is generally dense in simvasatin treated hippocampus. Higher magnification images show that the density of microglia is higher in simvasatin treated tissue than that in the control tissue.

Discussion

The present invention provides novel materials, such as brain cells (e.g., normal, apoE-deficient, apoE4-containing) as models of neurodegenerative diseases, and methods for inducing and/or preventing the induction of characteristics of such diseases in brain cells so that such cells can be used as a model of neurodegenerative diseases, including Alzheimer's disease.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted. By their citation of various references in this document, applicants do not admit any particular reference is "prior art" to their invention.

What is claimed is:

1. An in vitro method of determining the effect of a substance on characteristics that are indicative of Alzheimer's Disease in rodent brain cells, said method comprising:
   (A) exposing said brain cells to a cathepsin D-increasing agent or compound under conditions that increase the concentration or amount of cathepsin D in said cells to an effective concentration,
   (B) maintaining said cells for a time that is sufficient to induce, relative to the levels present in the absence of said substance, one or more characteristics indicative of Alzheinier's Disease in said cells as a result of said increase in said cathepsin D,
   (C) adding said substance before, during and/or after said exposing or said maintaining; and
   (D) determining whether the presence of said substance has an effect on the induction of said one or more characteristics, wherein said characteristics are selected from the group consisting of:
      (1) the formation of neurofibrillary tangles,
      (2) the hyperphosphorylation of tau,
      (3) the fragmentation of tau,
      (4) the production and/or release of brain-produced cytokines TGF-beta, IL-1b, or TNF,
      (5) a microglia reaction or microglial activation,
      (6) indications of brain inflammatory reactions,
      (7) conversion of p35 to p25,
      (8) changes in the level and/or activity of cyclin dependent protein kinase 5 (cdk5), and
      (9) changes in the level and/or activity of mitogen activated protein kinases (MAPK), wherein said effect on said induction of any or all of said characteristics in D(1)–D(9) is indicative of the appearance or disappearance, respectively, of said characteristics of Alzheimer's Disease.

2. The method of claim 1, wherein said characteristic is said formation of neurofibrillary tangles.

3. The method of claim 1, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

4. The method of claim 3, wherein said compound is N-CBZ-L-phenylalanyl-L-alanine-diazomethylketone.

5. The method of claim 2, wherein said brain cells are in the form of dissociated cells.

6. The method of claim 2, wherein said brain cells are in the form of a brain slice.

7. The method of claim 6, wherein said brain slice is selected from the group consisting of a hippocampal slice, an entorhinal cortex slice, an entorhinohippocampal slice, a neocortex slice, a hypothalamic slice, and a cortex slice.

8. The method of any one of claims 2–7, wherein said rodent brain cells are apolipoprotein E-deficient rodent brain cells.

9. The method of claim 8, wherein said rodent is a mouse.

10. The method of claim 8, wherein said rodent is a rat.

11. The method of any one of claims 2–7, wherein said rodent brain cells are apolipoprotein E-containing rodent brain cells.

12. The method of claim 11, wherein said rodent is a mouse.

13. The method of claim 11, wherein said rodent is a rat.

14. The method of claim 1, wherein said characteristic is said hyperphosphorylation of tau.

15. The method of claim 14, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

16. The method of claim 15, wherein said compound is N-CBZ-L-phenylalanyl-L-alanine-diazomethylketone.

17. The method of claim 14, where said brain cells are in the form of dissociated cells.

18. The method of claim 14, wherein said brain cells are in the form of a brain slice.

19. The method of claim 18, wherein said brain slice is selected from the group consisting of a hippocampal slice, an entorhinal cortex slice, an entorhinohippocanipal slice, a neocortex slice, a hypothalamic slice, and a cortex slice.

20. The method of any one of claims 14–19, wherein said rodent brain cells are apolipoprotein E-deficient rodent brain cells.

21. The method of claim 20, wherein said rodent is a mouse.

22. The method of claim 20, wherein said rodent is a rat.

23. The method of any one of claims 14–19, wherein said rodent brain cells are apolipoprotein E-containing rodent brain cells.

24. The method of claim 23, wherein said rodent is a mouse.

25. The method of claim 23, wherein said rodent is a rat.

26. The method of claim 1, wherein said characteristic is said fragmentation of tau.

27. The method of claim 26, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

28. The method of claim 27, wherein said compound is N-CBZ-L-phenylalanyl-L-alanine-diazomethylketone.

29. The method of claim 26, where said brain cells are in the form of dissociated cells.

30. The method of claim 26, wherein said brain cells are in the form of a brain slice.

31. The method of claim 30, wherein said brain slice is selected from the group consisting of a hippocampal slice, an entorhinal cortex slice, an entorhinohippocampal slice, a neocortex slice, a hypothalamic slice, and a cortex slice.

32. The method of any one of claims 26–31, wherein said rodent brain cells are apolipoprotein E-deficient rodent brain cells.

33. The method of claim 32, wherein said rodent is a mouse.

34. The method of claim 32, wherein said rodent is a rat.

35. The method of any one of claims 26–31, wherein said rodent brain cells are apolipoprotein E-containing rodent brain cells.

36. The method of claim 35, wherein said rodent is a mouse.

37. The method of claim 35, wherein said rodent is a rat.

38. The method of claim 1, wherein said characteristic is said production and/or release of brain-produced cytokines TGF-beta, IL-1b, or TNF.

39. The method of claim 38, wherein said compound is selected from the group consisting of chloroquine, N-CBZ-L-phenylalanyl-L-alanine-diazomethylketofle, N-CBZ-L-phenylalanyl-L-phenylalanine-diazomethylketone, and beta-amyloid.

40. The method of claim 39, wherein said compound is N-CBZ-L-phenylalanyl-L-alanine-diazomethylketone.

41. The method of claim 38, where said brain cells are in the form of dissociated cells.

42. The method of claim 38, wherein said brain cells are in the form of a brain slice.

43. The method of claim 42, wherein said brain slice is selected from the group consisting of a hippocampal slice, an entorhinal cortex slice, an entorhinohippocampal slice, a neocortex slice, a hypothalamic slice, and a cortex slice.

44. The method of any one of claims 38–43, wherein said rodent brain cells are apolipoprotein E-deficient rodent brain cells.

45. The method of claim 44, wherein said rodent is a mouse.

46. The method of claim 45, wherein said rodent is a rat.

47. The method of any one of claims 38–43, wherein said rodent brain cells are apolipoprotein E-containing rodent brain cells.

48. The method of claim 47, wherein said rodent is a mouse.

49. The method of claim 47, wherein said rodent is a rat.

50. The method of claim 1, wherein said characteristic is said microglia reaction or microglial activation.

51. The method of claim 50, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

52. The method of claim 51, wherein said compound is N-CBZ-L-phenylalanyl-L-alanine-diazomethylketone.

53. The method of claim 50, where said brain cells are in the form of dissociated cells.

54. The method of claim 50, wherein said brain cells are in the form of a brain slice.

55. The method of claim 54, wherein said brain slice is selected from the group consisting of a hippocampal slice, an entorhinial cortex slice, an entorhinohippocampal slice, a neocortex slice, a hypothalamic slice, and a cortex slice.

56. The method of any one of claims 50–55, wherein said rodent brain cells are apolipoprotein E-deficient rodent brain cells.

57. The method of claim 56, wherein said rodent is a mouse.

58. The method of claim 56, wherein said rodent is a rat.

59. The method of any one of claims 50–55, wherein said roden brain cells are apolipoprotein E-containing rodent brain cells.

60. The method of claim 59, wherein said rodent is a mouse.

61. The method of claim 59, wherein said rodent is a rat.

62. The method of claim 1, wherein said characteristic is said indications of brain inflammatory reactions.

63. The method of claim 62, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

64. The method of claim 63, wherein said compound is N-CBZ-L-phenylalanyl-L-alanine-diazomethylketone.

65. The method of claim 64, where said brain cells are in the form of dissociated cells.

66. The method of claim 62, wherein said brain cells are in the form of a brain slice.

67. The method of claim 66, wherein said brain slice is selected from the group consisting of a hippocampal slice, an entorhinal cortex slice, an entorhinohippocampal slice, a neocortex slice, a hypothalamic slice, and a cortex slice.

68. The method of any one of claims 62–67, wherein said rodent brain cells are apolipoprotein E-deficient rodent brain cells.

69. The method of claim 68, wherein said rodent is a mouse.

70. The method of claim 68, wherein said rodent is a rat.

71. The method of any one of claims 62–67, wherein said rodent brain cells are apolipoprotein E-containing rodent brain cells.

72. The method of claim 71, wherein said rodent is a mouse.

73. The method of claim 71, wherein said rodent is a rat.

74. The method of claim 1, wherein said characteristic is said conversion of p35 to p25.

75. The method of claim 74, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

76. The method of claim 75, wherein said compound is N-CBZ-L-phenylalanyl-L-alanine-diazomethylketone.

77. The method of claim 74, where said brain cells are in the form of dissociated cells.

78. The method of claim 74, wherein said brain cells are in the form of a brain slice.

79. The method of claim 78, wherein said brain slice is selected from the group consisting of a hippocampal slice, an entorhinal cortex slice, an entorhinohippocampal slice, a neocortex slice, a hypothalamic slice, and a cortex slice.

80. The method of any one of claims 74–79, wherein said rodent brain cells are apolipoprotein E-deficient rodent brain cells.

81. The method of claim 80, wherein said rodent is a mouse.

82. The method of claim 80, wherein said rodent is a rat.

83. The method of any one of claims 74–79, wherein said rodent brain cells are apolipoprotein E-containing rodent brain cells.

84. The method of claim 83, wherein said rodent is a mouse.

85. The method of claim 84, wherein said rodent is a rat.

86. The method of claim 1, wherein said characteristic is said changes in the level and/or activity of cyclin dependent protein kinase 5 (cdk5).

87. The method of claim 86, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

88. The method of claim 87, wherein said compound is N-CBZ-L-phenylalanyl-L-alanine-diazomethylketone.

89. The method of claim 86, where said brain cells are in the form of dissociated cells.

90. The method of claim 86, wherein said brain cells are in the form of a brain slice.

91. The method of claim 90, wherein said brain slice is selected from the group consisting of a hippocampal slice, an entorhinal cortex slice, an entorhinohippocampal slice, a neocortex slice, a hypothalamic slice, and a cortex slice.

92. The method of any one of claims 86–91, wherein said rodent brain cells are apolipoprotein E-deficient rodent brain cells.

93. The method of claim 92, wherein said rodent is a mouse.

94. The method of claim 92, wherein said rodent is a rat.

95. The method of any one of claims 86–91, wherein said rodent brain cells are apolipoprotein E-containing rodent brain cells.

96. The method of claim 95, wherein said rodent is a mouse.

97. The method of claim 95, wherein said rodent is a rat.

98. The method of claim 1, wherein said characteristic is said changes in the level and/or activity of mitogen activated protein kinases.

99. The method of claim 98, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

100. The method of claim 99, wherein said compound is N-CBZ-L-phenylalanyl-L-alanine-diazomethylketone.

101. The method of claim 98, where said brain cells are in the form of dissociated cells.

102. The method of claim 98, wherein said brain cells are in the form of a brain slice.

103. The method of claim 102, wherein said brain slice is selected from the group consisting of a hippocampal slice, an entorhinal cortex slice, an entorhinohippocampal slice, a neocortex slice, a hypothalamic slice, and a cortex slice.

104. The method of any one of claims 98–103, wherein said rodent brain cells are apolipoprotein E-deficient rodent brain cells.

105. The method of claim 104, wherein said rodent is a mouse.

106. The method of claim 104, wherein said rodent is a rat.

107. The method of any one of claims 98–103, wherein said rodent brain cells are apolipoprotein E-containing rodent brain cells.

108. The method of claim 107, wherein said rodent is a mouse.

109. The method of claim 107, wherein said rodent is a rat.

110. An in vitro method of determining the effect of a substance on characteristics that are indicative of Alzheimer's Disease in rodent brain cells, said method comprising:

(A) exposing said brain cells to a condition that disrupts lysosomal activity in said cells, wherein said condition comprises contacting said cells with a compound that disrupts lysosomal activity, (B) maintaining said cells for a time that is sufficient to induce, relative to the levels present in the absence of said substance, one or more characteristics indicative of said Alzheimer's Disease in said cells as a result of said disruption of said lysosomal activity, (C) adding said substance before, during and/or after said exposing or said maintaining; and (D) determining whether the presence of said substance has an effect on the induction of said one or more characteristics, wherein said characteristics are selected from the group consisting of:

(1) the formation of neurofibrillary tangles,
(2) the hyperphosphoiylat ion of tau,
(3) the fragmentation of tau,
(4) the production and/or release of brain-produced cytokines TGF-beta, IL-1b, or TNF,
(5) a microgha reaction or microglial activation,
(6) indications of brain inflammatory reactions, conversion of p35 to p25,
(8) changes in the level and/or activity of cyclin dependent protein kinase 5 (cdk5), and
(9) changes in the level and/or activity of mitogen activated protein kinases (MAPK), wherein said effect on said induction of any or all of said characteristics in D(1)–D(9) is indicative of the appearance or disappearance, respectively, of said characteristics of said Alzheimer's Disease.

111. The method of claim 110, wherein said characteristic is said formation of neurofibrillary tangles.

112. The method of claim 111, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

113. The method of claim 112, wherein said compound is N-CBZ-L-phenylalanyl-L-alanine-diazomethylketone.

114. The method of claim 111, where said brain cells are in the form of dissociated cells.

115. The method of claim 111, wherein said brain cells are in the form of a brain slice.

116. The method of claim 115, wherein said brain slice is selected from the group consisting of a hippocampal slice, an entorhinal cortex slice, an entorhinohippocampal slice, a neocortex slice, a hypothalamic slice, and a cortex slice.

117. The method of any one of claims 111–116, wherein said rodent brain cells are apolipoprotein E-deficient rodent brain cells.

118. The method of claim 117, wherein said rodent is a mouse.

119. The method of claim 118, wherein said rodent is a rat.

120. The method of any one of claims 111–116, wherein said rodent brain cells are apolipoprotein E-containing rodent brain cells.

121. The method of claim 120, wherein said rodent is a mouse.

122. The method of claim 120, wherein said rodent is a rat.

123. The method of claim 110, wherein said characteristic is hyperphosphorylation of tau.

124. The method of claim 123, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

125. The method of claim 124, wherein said compound is N-CBZ-L-phenylalanyl-L-alanine-diazomethylketone.

126. The method of claim 123, where said brain cells are in the form of dissociated cells.

127. The method of claim 123, wherein said brain cells are in the form of a brain slice.

128. The method of claim 127, wherein said brain slice is selected from the group consisting of a hippocampal slice, an entorhinal cortex slice, an entorhinohippocampal slice, a neocortex slice, a hypothalamic slice, and a cortex slice.

129. The method of any one of claims 123–128, wherein said rodent brain cells are apolipoprotein E-deficient rodent brain cells.

130. The method of claim 129, wherein said rodent is a mouse.

131. The method of claim 129, wherein said rodent is a rat.

132. The method of any one of claims 123–128, wherein said rodent brain cells are apolipoprotein E-containing rodent brain cells.

133. The method of claim 132, wherein said rodent is a mouse.

134. The method of claim 132, wherein said rodent is a rat.

135. The method of claim 110, wherein said characteristic is said fragmentation of tau.

136. The method of claim 135, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

137. The method of claim 136, wherein said compound is N-CBZ-L-phenylalanyl-L-alanine-diazomethylketone.

138. The method of claim 135, where said brain cells are in the form of dissociated cells.

139. The method of claim 135, wherein said brain cells are in the form of a brain slice.

140. The method of claim 139, wherein said brain slice is selected from the group consisting of a hippocampal slice, an entorhinal cortex slice, an entorhinohippocampal slice, a neocortex slice, a hypothalamic slice, and a cortex slice.

141. The method of any one of claims 135–140, wherein said rodent brain cells are apolipoprotein E-deficient rodent brain cells.

142. The method of claim 141, wherein said rodent is a mouse.

143. The method of claim 141, wherein said rodent is a rat.

144. The method of any one of claims 135–140, wherein said rodent brain cells are apolipoprotein E-containing rodent brain cells.

145. The method of claim 144, wherein said rodent is a mouse.

146. The method of claim 144, wherein said rodent is a rat.

147. The method of claim 110, wherein said characteristic is said production and/or release of brain-produced cytokines TGF-beta, IL-1b, or TNF.

148. The method of claim 135, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

149. The method of claim 148, wherein said compound is N-CBZ-L-phenylalanyl-L-alanine-diazomethylketone.

150. The method of claim 148, where said brain cells are in the form of dissociated cells.

151. The method of claim 147, wherein said brain cells are in the form of a brain slice.

152. The method of claim 151, wherein said brain slice is selected from the group consisting of a hippocampal slice, an entorhinal cortex slice, an entorhinohippocampal slice, a neocortex slice, a hypothalamic slice, and a cortex slice.

153. The method of any one of claims 147–152, wherein said rodent brain cells are apolipoprotein E-deficient rodent brain cells.

154. The method of claim 153, wherein said rodent is a mouse.

155. The method of claim 153, wherein said rodent is a rat.

156. The method of any one of claims 147–152, wherein said rodent brain cells are apolipoprotein E-containing rodent brain cells.

157. The method of claim 156, wherein said rodent is a mouse.

158. The method of claim 156, wherein said rodent is a rat.

159. The method of claim 110, wherein said characteristic is said microglia reaction or microglial activation.

160. The method of claim 159, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

161. The method of claim 160, wherein said compound is N-CBZ-L-phenylalanyl-L-alanine-diazomethylketone.

162. The method of claim 159, wherein said brain cells are in the form of dissociated cells.

163. The method of claim 159, wherein said brain cells are in the form of a brain slice.

164. The method of claim 163, wherein said brain slice is selected from the group consisting of a hippocampal slice, an entorhinal cortex slice, an entorhinohippocampal slice, a neocortex slice, a hypothalamic slice, and a cortex slice.

165. The method of any one of claims 157–164, wherein said rodent brain cells are apolipoprotein E-deficient rodent brain cells.

166. The method of claim 165, wherein said rodent is a mouse.

167. The method of claim 165, wherein said rodent is a rat.

168. The method of any one of claims 159–164, wherein said rodent brain cells are apolipoprotein E-containing rodent brain cells.

169. The method of claim 168, wherein said rodent is a mouse.

170. The method of claim 168, wherein said rodent is a rat.

171. The method of claim 110, wherein said characteristic is said indications of brain inflammatory reactions.

172. The method of claim 171, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

173. The method of claim 172, wherein said compound is N-CBZ-L-phenylalanyl-L-alanine-diazomethylketone.

174. The method of claim 171, where said brain cells are in the form of dissociated cells.

175. The method of claim 171, wherein said brain cells are in the form of a brain slice.

176. The method of claim 175, wherein said brain slice is selected from the group consisting of a hippocampal slice, an entorhinal cortex slice, an entorhinohippocampal slice, a neocortex slice, a hypothalamic slice, and a cortex slice.

177. The method of any one of claims 171–176, wherein said rodent brain cells are apolipoprotein E-deficient rodent brain cells.

178. The method of claim 177, wherein said rodent is a mouse.

179. The method of claim 177, wherein said rodent is a rat.

180. The method of any one of claims 171–176, wherein said rodent brain cells are apolipoprotein E-containing rodent brain cells.

181. The method of claim 180, wherein said rodent is a mouse.

182. The method of claim 180, wherein said rodent is a rat.

183. The method of claim 110, wherein said characteristic is said conversion of p35 to p25.

184. The method of claim 83, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

185. The method of claim 184, wherein said compound is N-CBZ-L-phenylalanyl-L-alanine-diazomethylketone.

186. The method of claim 183, where said brain cells are in the form of dissociated cells.

187. The method of claim 185, wherein said brain cells are in the form of a brain slice.

188. The method of claim 187, wherein said brain slice is selected from the group consisting of a hippocampal slice, an entorhinal cortex slice, an entorhinohippocampal slice, a neocortex slice, a hypothalamic slice, and a cortex slice.

189. The method of any one of claims 183–188, wherein said rodent brain cells are apolipoprotein E-deficient rodent brain cells.

190. The method of claim 181, wherein said rodent is a mouse.

191. The method of claim 189, wherein said rodent is a rat.

192. The method of any one of claims 183–188, wherein said rodent brain cells are apolipoprotein E-containing rodent brain cells.

193. The method of claim 192, wherein said rodent is a mouse.

194. The method of claim 192, wherein said rodent is a rat.

195. The method of claim 110, wherein said characteristic is said changes in the level and/or activity of cyclin dependent protein kinase 5 (cdc5).

196. The method of claim 195, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

197. The method of claim 196, wherein said compound is N-CBZ-L-phenylalanyl-alanine-diazomethylketone.

198. The method of claim 195, where said brain cells are in the form of dissociated cells.

199. The method of claim 195, wherein said brain cells are in the form of a brain slice.

200. The method of claim 199, wherein said brain slice is selected from the group consisting of a hippocampal slice, an entorhinal cortex slice, an entorhinohippocampal slice, a neocortex slice, a hypothalamic slice, and a cortex slice.

201. The method of any one of claims 195–200, wherein said rodent brain cells are apolipoprotein E-deticient rodent brain cells.

202. The method of claim 201, wherein said rodent is a mouse.

203. The method of claim 201, wherein said rodent is a rat.

204. The method of any one of claims 195–200, wherein said rodent brain cells are apolipoprotein E-containing rodent brain cells.

205. The method of claim 204, wherein said rodent is a mouse.

206. The method of claim 204, wherein said rodent is a rat.

207. The method of claim 110, wherein said characteristic is said changes in the level and/or activity of mitogen activated protein kinases.

208. The method of claim 207, wherein said compound is selected from the group consisting of chloroquine, N-CBZ-L-phenylalanyl-L-alanine-diazomethylketone, N-CBZ-L-phenylalanyl-L-phenylalanine-diazomethylketone, and beta-amyloid.

209. The method of claim 208, wherein said compound is N-CBZ-L-phenylalanyl-L-alanine-diazomethylketone.

210. The method of claim 207, where said brain cells are in the form of dissociated cells.

211. The method of claim 207, wherein said brain cells are in the form of a brain slice.

212. The method of claim 211, wherein said brain slice is selected from the group consisting of a hippocampal slice, an entorhinal cortex slice, an entorhinohippocampal slice, a neocortex slice, a hypothalamic slice, and a cortex slice.

213. The method of any one of claims 207–212, wherein said rodent brain cells are apolipoprotein E-deficient rodent brain cells.

214. The method of claim 213, wherein said rodent is a mouse.

215. The method of claim 213, wherein said rodent is a rat.

216. The method of any one of claims 207–212, wherein said rodent brain cells are apolipoprotein E-containing rodent brain cells.

217. The method of claim 216, wherein said rodent is a mouse.

218. The method of claim 216, wherein said rodent is a rat.

* * * * *